United States Patent
Yue et al.

(10) Patent No.: US 6,872,560 B1
(45) Date of Patent: Mar. 29, 2005

(54) HUMAN HYDROLYTIC ENZYMES

(75) Inventors: Henry Yue, Sunnyvale, CA (US); Jennifer L. Hillman, Mountain View, CA (US); Y. Tom Tang, San Jose, CA (US); Mariah R. Baughn, San Leandro, CA (US); Dyung Aina M. Lu, San Jose, CA (US); Yalda Azimazai, Castro Valley, CA (US)

(73) Assignee: Incyte Corporation, Wilmington, DE (US)

( * ) Notice: Subject to any disclaimer, the term of this patent is extended or adjusted under 35 U.S.C. 154(b) by 292 days.

(21) Appl. No.: 10/070,634

(22) PCT Filed: Aug. 31, 2000

(86) PCT No.: PCT/US00/24107

§ 371 (c)(1),
(2), (4) Date: Mar. 1, 2002

(87) PCT Pub. No.: WO01/16334

PCT Pub. Date: Mar. 8, 2001

Related U.S. Application Data

(60) Provisional application No. 60/151,819, filed on Sep. 1, 1999.

(51) Int. Cl.$^7$ .............................. C12N 9/64; C12N 15/57
(52) U.S. Cl. ........................ 435/226; 435/252.9; 435/6; 536/23.2
(58) Field of Search ..................... 435/252.3, 6, 226; 536/23.2

(56) References Cited

PUBLICATIONS

Evans, G.A., et al. (1997) Acc. No. AF015416.*
Mori, N, et al. (1979) Chem. Pharm. Bull. 27(2), 571–572.*
Lee, M.R., et al. (1968) Nature 217, 758–759.*
James J.–D. Hsieh et al., Taspase 1: A Threonine Aspartase Required for Cleavage of MLL and Proper HOX Gene Expression, Cell, vol. 115, 293–303, Oct. 31, 2003, Cell Press.
NCBI Database, Accession AAC13614 (GI 3047103), Nov. 12, 1999.
NCBI Database, Accession CAB91238 (GI 7800880), Oct. 22, 2001.

* cited by examiner

Primary Examiner—Charles L. Patterson, Jr.
(74) Attorney, Agent, or Firm—Foley & Lardner LLP

(57) ABSTRACT

The invention provides human hydrolytic enzymes (HYENZ) and polynucleotides which identify and encode HYENZ. The invention also provide expression vectors, host cells, antibodies, agonists, and antagonists. The invention also provides methods for diagnosing, treating, or preventing disorders associated with expression of HYENZ.

13 Claims, No Drawings

HUMAN HYDROLYTIC ENZYMES

This application is a national stage application filed under 35 U.S.C. § 371 of International Application No. PCT/US00/24107, filed Aug. 31, 2000 and published in English as WO 60/151,819, on March 8, 2001, which claims the benefit of U.S. Provisional Application No. 60/151,189, filed Sep. 1, 1999

TECHNICAL FIELD

This invention relates to nucleic acid and amino acid sequences of hydrolytic enzymes and to the use of these sequences in the diagnosis, treatment, and prevention of neurological disorders, immune system disorders, genetic disorders, and cell proliferation disorders, including cancer.

BACKGROUND OF THE INVENTION

Hydrolysis is the breaking of a covalent bond in a substrate by introduction of a water molecule. The reaction involves a nucleophilic attack by the water molecule's oxygen atom on a target bond in the substrate. The water molecule is split across the target bond, breaking the bond and generating two product molecules. Hydrolytic enzymes participate in reactions essential to functions such as cell signaling, cell proliferation, inflammation, apoptosis, secretion and excretion. Hydrolytic enzymes are involved in key steps in disease processes involving these functions. Hydrolytic enzymes, or hydrolases, may be grouped by substrate specificity into classes including aminohydrolases, phospholipases, carboxyl-esterases, phosphodiesterases, lysozymes, glycosidases, glyoxalases, sulfatases, phosphohydrolases, and serine hydrolases.

NG, NG-dimethylarginine dimethylaminohydrolase (DDAH) is an enzyme that hydrolyzes the endogenous nitric oxide synthase (NOS) inhibitors. NG-monomethyl-arginine and NG, NG-dimethyl-L-arginine to L-citrulline. Inhibiting DDAH can cause increased intracellular concentration of NOS inhibitors to levels sufficient to inhibit NOS. Therefore, DDAH inhibition may provide a method of NOS inhibition and changes in the activity of DDAH could play a role in pathophysiological alterations in nitric oxide generation (MacAllister, R. J., et al. (1996) Br. J. Pharmacol. 119: 1533–1540). DDAH was found in neurons displaying cytoskeletal abnormalities and oxidative stress in Alzheimer's disease. In age-matched control cases, DDAH was not found in neurons. This suggests that oxidative stress- and nitric oxide-mediated events play a role in the pathogenesis of Alzheimer's disease (Smith, M. A., et al. (1998) Free Radic. Biol. Med. 25: 898–902).

Dipeptidyl peptidase III is an enzyme that catalyzes the release of an N-terminal dipeptide from a peptide of four or more residues. It is localized to the cytosol and is active at neutral pH. It is inactive oh Glu(4), Gly(4), and bonds involving proline. (See ExPasy—ENZYME, EC 3.4.14.4.)

Peptide deformylase hydrolyzes the formyl group at the N-terminus of newly synthesized polypeptides in prokaryotes. Deletion of the gene encoding peptide deformylase is lethal in E. coli. This lethality makes peptide deformylase a target for the design of new antibiotics (Becker, A. et al. (1998) J. Biol. Chem. 273:11413–11416 and Rajagopalan, P. T. R. and Pei, D. (1998) J. Biol. Chem. 273:22305–22310).

Trehalase is an enzyme that hydrolyzes trehalose, a protein that is thought to play a role in thermotolerance and dessication tolerance in yeast. Neutral trehalase is localized in the cytosol, while acid trehalase is localized in the vacuole. There is strong evidence that it is the neutral trehalase that hydrolyzes trehalose in intact cells. Evidence also suggests that the enhanced thermotolerance due to increased levels of trehalase is not due to the accumulation of trehalose. Trehalase may interact with heat shock protein 70 (Nwaka, S., et al. (1995) J. Biol. Chem. 270:10193–10198).

Phosphodiesterases catalyze the hydrolysis of one of the two ester bonds in a phosphodiester compound. Phosphodiesterases are, therefore, crucial to a variety of cellular processes. Phosphodiesterases include DNA and RNA endo- and exo-nucleases, which are essential to cell growth and replication as well as protein synthesis.

Pancreatic lipase and colipase form a complex that plays a key role in dietary fat digestion by converting insoluble long chain triacylgycerols into more polar molecules able to cross the brush border of intestinal cells. Colipase hinds to the C-terminal domain of lipase. In solution, this interaction involves the formation of an ion pair between a glutamic acid residue of colipase and a lysine residue of lipase. These residues are strictly conserved among species (Ayvazian, L., et. al. (1998) J. Biol. Chem. 273(50): 33604–33609). Colipase appears to overcome the inhibitory effects of bile salts on pancreatic lipase (Online Mendelian Inheritance in Man (OMIM) 246600). Diacyglycerol lipase hydrolyzes triacylglycerol, diacylglycerol and other low-density lipoproteins (ExPASy—ENZYME, EC 3.1.1.34).

Carboxylesterases are proteins that hydrolyze carboxylic esters and are classified into three categories—A, B, and C. Most type-B carboxylesterases are evolutionarily related and are considered to comprise a family of proteins. The type-B carboxylesterase family of proteins includes vertebrate acetylcholinesterase, mammalian liver microsomal carboxylesterase, mammalian bile-salt-activated lipase, and duck fatty acyl-CoA hydrolase. Some members of this protein family are not catalytically active but contain a domain related evolutionarily to other type-B carboxylesterases, such as thyroglobulin and *Drosophila* protein neuractin. The active site of carboxylesterases involves three residues: a serine, a glutamate or aspartate, and a histidine. The sequence surrounding this catalytic site is well conserved and can be used as a signature pattern (PROSITE: PDOC00112).

Lysozyme c superfamily consists of conventional lysozymes c, calcium-binding lysozymes c, and α-lactalbumin (Prager, E. M. and Jolles, P. (1996) EXS 75:9–31). The proteins in this superfamily have 35–40% sequence homology and share a common three dimensional fold, but can have different functions. Lysozymes bind and cleave the glycosidic bond linkage in sugars (Iyer, L. K. and Qasba, P. K. (1999) Protein Eng. 12:129–139). Lysozymes c are ubiquitous in a variety of tissues and secretions and can lyse the cell walls of ceratin bacteria (McKenzie, H. A. (1996) EXS 75: 365–409). Alpha-lactalbumin is a metalloprotein that binds calcium and participates in the synthesis of lactose (Iyer, L. K and Qasba, P. K. (1999) Protein Eng. 12: 129–139). Alpha-lactalbumin occurs in mammalian milk and colostrum (McKenzie, supra.).

The glyoxylase system consists of glyoxalase I, which catalyzes the formation of S-D-lactoylglutathione from methyglyoxal, a side product of triose-phosphate energy metabolism, and glyoxylase II, which hydrolyzes S-D-lactoylglutathione to D-lactic acid and reduced glutathione. Methyglyoxal levels are elevated during hyperglycemia, likely due to increased triose-phosphate energy metabolism. Elevated levels of glyoxylase II activity have been found in human and in a rat model of non-insulin-dependent diabetes mellitus. The glyoxylase system has been implicated in the detoxification of bacterial toxins, and in the control of cell proliferation and microtubule assembly. Elevated levels of S-D-lactoylglutathione, the substrate of glyoxylase II, induced growth arrest and toxicity in HL60 cells. Thus, the glyoxylase system, and glyoxylase II in particular, may be associated with cell proliferation and autoimmune system disorders such as diabetes.

Sulfatases are members of a highly conserved gene family that share extensive sequence homology and a high degree of structural similarity. Sulfatases catalyze the cleavage of sulfate esters. To perform this function, sulfatases undergo a unique posttranslational modification in the endoplasmic reticulum that involves the oxidation of a conserved cysteine residue. A human disorder called multiple sulfatase deficiency is due to a defect in this posttranslational modification step, leading to inactive sulfatases (Recksiek, M., et al. (1998) J. Biol. Chem. 273: 6096–6103).

Phosphohydrolases are enzymes that catalyze the hydrolysis of phosphate esters. Some phosphohydrolases contain a mutT domain signature sequence. MutT is a protein involved in the GO system responsible for removing an oxidatively damaged form of guanine from DNA. A region of about 40 amino acid residues, found in the N-terminus of mutT, is also found in other proteins, including some phosphohydrolases (PROSITE: PDOC00695).

Phosphatidic acid phosphohydrolases (PAPs) catalyze the de phophorylation of phosphatidic acid to form diacylglycerol. The hydrolysis of phosphatidic acid by PAP terminates the signaling functions of phophatidic acid and, by generating diacylglycerol, activates $Ca^{2+}$- and phospholipid-dependent protein kinase C enzymes. PAP-2 is localized to the plasma membrane and is independent of $Mg^{2+}$. It may play a role in modulating the signaling functions of phosphatidic acid, lysophosphatidic acid, and sphingomyelin derived lipid phosphomonoesters. Three isozymes of PAP have been found in humans to date: PAP-2a, PAP-2b, and PAP-2c. (See, Roberts, R. et al. (1998) J. Biol. Chem. 273:22059–22067.)

Glycosidases catalyze the cleavage of hemiacetyl bonds of glycosides, which are compounds that contain one or more sugar. Mammalian beta-galactosidase removes the terminal galactose from gangliosides, glycoproteins, and glycosaminoglycans. Beta-galactosidases belong to family 35 in the classification of glycosyl hydrolases. Deficiency of this enzyme is associated with the genetic disease GM1-gangliosidosis known as Morquio disease type B (PROSITE: PDOC00910).

Serine hydrolases are a functional class of hydrolytic enzymes that contain a serine residue in their active site. This class of enzymes contains proteinases, esterases, and lipases which hydrolyze a variety of substrates and, therefore, have different biological roles. Proteins in this superfamily can be further grouped into subfamilies based on substrate specificity or amino acid similarities (Puente, X. S. and Lopez-Ont, C. (1995) J. Biol. Chem. 270: 12926–12932).

The discovery of new hydrolytic enzymes and the polynucleotides encoding them satisfies a need in the art by providing new compositions which are useful in the diagnosis, prevention, and treatment of neurological disorders, immune system disorders, genetic disorders, and cell proliferation disorders, including cancer.

SUMMARY OF THE INVENTION

The invention features purified polypeptides, hydrolytic enzymes, referred to collectively as "HYENZ" and individually as "HYENZ-1," "HYENZ-2," "HYENZ-3," "HYENZ-4," "HYENZ-5," "HYENZ-6," "HYENZ-7," "HYENZ-8," "HYENZ-9," "HYENZ-10," "HYENZ-11," "HYENZ-12," "HYENZ-13," and "HYENZ-14." In one aspect, the invention provides an isolated polypeptide comprising an amino acid sequence selected from the group consisting of a) an amino acid sequence selected from the group consisting of SEQ ID NO:1–14, b) a naturally occurring amino acid sequence having at least 90% sequence identity to an amino acid sequence selected from the group consisting of SEQ ID NO:1–14, c) a biologically active fragment of an amino acid sequence selected from the group consisting of SEQ ID NO:1–14, and d) an immunogenic fragment of an amino acid sequence selected from the group consisting of SEQ ID NO:1–14. In one alternative, the invention provides an isolated polypeptide comprising the amino acid sequence of SEQ ID NO:1–14.

The invention further provides an isolated polynucleotide encoding a polypeptide comprising an amino acid sequence selected from the group consisting of a) an amino acid sequence selected from the group consisting of SEQ ID NO:1–14, b) a naturally occurring amino acid sequence having at least 90% sequence identity to an amino acid sequence selected from the group consisting of SEQ ID NO:1–14, c) a biologically active fragment of an amino acid sequence selected from the group consisting of SEQ ID NO:1–14, and d) an immunogenic fragment of an amino acid sequence selected from the group consisting of SEQ ID NO:1–14. In one alternative, the polynucleotide encodes a polypeptide selected from the group consisting of SEQ ID NO:1–14. In another alternative, the polynucleotide is selected from the group consisting of SEQ ID NO:15–28.

Additionally, the invention provides a recombinant polynucleotide comprising a promoter sequence operably linked to a polynucleotide encoding a polypeptide comprising an amino acid sequence selected from the group consisting of a) an amino acid sequence selected from the group consisting of SEQ ID NO:1–14, b) a naturally occurring amino acid sequence having at least 90% sequence identity to an amino acid sequence selected from the group consisting of SEQ ID NO:1–14, c) a biologically active fragment of an amino acid sequence selected from the group consisting of SEQ ID NO:1–14, and d) an immunogenic fragment of an amino acid sequence selected from the group consisting of SEQ ID NO:1–14. In one alternative, the invention provides a cell transformed with the recombinant polynucleotide. In another alternative, the invention provides a transgenic organism comprising the recombinant polynucleotide.

The invention also provides a method for producing a polypeptide comprising an amino acid sequence selected from the group consisting of a) an amino acid sequence selected from the group consisting of SEQ ID NO:1–14, b) a naturally occurring amino acid sequence having at least 90% sequence identity to an amino acid sequence selected from the group consisting of SEQ ID NO:1–14, c) a biologically active fragment of an amino acid sequence selected from the group consisting of SEQ ID NO:1–14, and d) an immunogenic fragment of an amino acid sequence selected from the group consisting of SEQ ID NO:1–14. The method comprises a) culturing a cell under conditions suitable for expression of the polypeptide, wherein said cell is transformed with a recombinant polynucleotide comprising a promoter sequence operably linked to a polynucleotide encoding the polypeptide, and b) recovering the polypeptide so expressed.

Additionally, the invention provides an isolated antibody which specifically binds to a polypeptide comprising an amino acid sequence selected from the group consisting of a) an amino acid sequence selected from the group consisting of SEQ ID NO:1–14, b) a naturally occurring amino acid sequence having at least 90% sequence identity to an amino acid sequence selected from the group consisting of SEQ ID NO:1–14, c) a biologically active fragment of an amino acid sequence selected from the group consisting of SEQ ID NO:1–14, and d) an immunogenic fragment of an amino acid sequence selected from the group consisting of SEQ ID NO:1–14.

The invention further provides an isolated polynucleotide comprising a polynucleotide sequence selected from the group consisting of a) a polynucleotide sequence selected from the group consisting of SEQ ID NO:15–28, b) a naturally occurring polynucleotide sequence having at least 70% sequence identity to a polynucleotide sequence selected from the group consisting of SEQ ID NO:15–28, c) a polynucleotide sequence complementary to a), d) a polynucleotide sequence complementary to b), and e) an RNA equivalent of a)–d). In one alternative, the polynucleotide comprises at least 60 contiguous nucleotides.

Additionally, the invention provides a method for detecting a target polynucleotide in a sample, said target polynucleotide having a sequence of a polynucleotide comprising a polynucleotide sequence selected from the group consisting of a) a polynucleotide sequence selected from the group consisting of SEQ ID NO:15–28, b) a naturally occurring polynucleotide sequence having at least 70% sequence identity to a polynucleotide sequence selected from the group consisting of SEQ ID NO:15–28, c) a polynucleotide sequence complementary to a), d) a polynucleotide sequence complementary to b), and e) an RNA equivalent of a)–d). The method comprises a) hybridizing the sample with a probe comprising at least 20 contiguous nucleotides comprising a sequence complementary to said target polynucleotide in the sample, and which probe specifically hybridizes to said target polynucleotide, under conditions whereby a hybridization complex is formed between said probe and said target polynucleotide or fragments thereof, and b) detecting the presence or absence of said hybridization complex, and optionally, if present, the amount thereof. In one alternative, the probe comprises at least 60 contiguous nucleotides.

The invention further provides a method for detecting a target polynucleotide in a sample, said target polynucleotide having a sequence of a polynucleotide comprising a polynucleotide sequence selected from the group consisting of a) a polynucleotide sequence selected from the group consisting of SEQ ID NO:15–28, b) a naturally occurring polynucleotide sequence having at least 70% sequence identity to a polynucleotide sequence selected from the group consisting of SEQ ID NO:15–28, c) a polynucleotide sequence complementary to a), d) a polynucleotide sequence complementary to b), and e) an RNA equivalent of a)–d). The method comprises a) amplifying said target polynucleotide or fragment thereof using polymerase chain reaction amplification, and b) detecting the presence or absence of said amplified target polynucleotide or fragment thereof, and, optionally, if present, the amount thereof.

The invention further provides a composition comprising an effective amount of a polypeptide comprising an amino acid sequence selected from the group consisting of a) an amino acid sequence selected from the group consisting of SEQ ID NO:1–14, b) a naturally occurring amino acid sequence having at least 90% sequence identity to an amino acid sequence selected from the group consisting of SEQ ID NO:1–14, c) a biologically active fragment of an amino acid sequence selected from the group consisting of SEQ ID NO:1–14, and d) an immunogenic fragment of an amino acid sequence selected from the group consisting of SEQ ID NO:1–14, and a pharmaceutically acceptable excipient. In one embodiment, the composition comprises an amino acid sequence selected from the group consisting of SEQ ID NO:1–14. The invention additionally provides a method of treating a disease or condition associated with decreased expression of functional HYENZ, comprising administering to a patient in need of such treatment the composition.

The invention also provides a method for screening a compound for effectiveness as an agonist of a polypeptide comprising an amino acid sequence selected from the group consisting of a) an amino acid sequence selected from the group consisting of SEQ ID NO:1–14, b) a naturally occurring amino acid sequence having at least 90% sequence identity to an amino acid sequence selected from the group consisting of SEQ ID NO:1–14, c) a biologically active fragment of an amino acid sequence selected from the group consisting of SEQ ID NO:1–14, and d) an immunogenic fragment of an amino acid sequence selected from the group consisting of SEQ ID NO:1–14. The method comprises a) exposing a sample comprising the polypeptide to a compound, and b) detecting agonist activity in the sample. In one alternative, the invention provides a composition comprising an agonist compound identified by the method and a pharmaceutically acceptable excipient. In another alternative, the invention provides a method of treating a disease or condition associated with decreased expression of functional HYENZ, comprising administering to a patient in need of such treatment the composition.

Additionally, the invention provides a method for screening a compound for effectiveness as an antagonist of a polypeptide comprising an amino acid sequence selected from the group consisting of a) an amino acid sequence selected from the group consisting of SEQ ID NO:1–14, b) a naturally occurring amino acid sequence having at least 90% sequence identity to an amino acid sequence selected from the group consisting of SEQ ID NO:1–14, c) a biologically active fragment of an amino acid sequence selected from the group consisting of SEQ ID NO:1–14, and d) an immunogenic fragment of an amino acid sequence selected from the group consisting of SEQ ID NO:1–14. The method comprises a) exposing a sample comprising the polypeptide to a compound, and b) detecting antagonist activity in the sample. In one alternative, the invention provides a composition comprising an antagonist compound identified by the method and a pharmaceutically acceptable excipient. In another alternative, the invention provides a method of treating a disease or condition associated with overexpression of functional HYENZ, comprising administering to a patient in need of such treatment the composition.

The invention fun provides a method of screening for a compound that specifically binds to a polypeptide comprising an amino acid sequence selected from the group consisting of a) an amino acid sequence selected from the group consisting of SEQ ID NO:1–14, b) a naturally occurring amino acid sequence having at least 90% sequence identity to an amino acid sequence selected from the group consisting of SEQ ID NO:1–14, c) a biologically active fragment of an amino acid sequence selected from the group consisting of SEQ ID NO:1–14, and d) an immunogenic fragment of an amino acid sequence selected from the group consisting of SEQ ID NO:1–14. The method comprises a) combining the polypeptide with at least one test compound under suitable conditions, and b) detecting binding of the polypeptide to the test compound, thereby identifying a compound that specifically binds to the polypeptide.

The invention further provides a method of screening for a compound that modulates the activity of a polypeptide comprising an amino acid sequence selected from the group consisting of a) an amino acid sequence selected from the group consisting of SEQ ID NO:1–14, b) a naturally occurring amino acid sequence having at least 90% sequence identity to an amino acid sequence selected from the group consisting of SEQ ID NO:1–4, c) a biologically active fragment of an amino acid sequence selected from the group consisting of SEQ ID NO:1–4, and d) an immunogenic fragment of an amino acid sequence selected from the group consisting of SEQ ID NO:1–14. The method comprises a) combining the polypeptide with at least one test compound under conditions permissive for the activity of the polypeptide, b) assessing the activity of the polypeptide in the presence of the test compound, and c) comparing the activity of the polypeptide in the presence of the test compound with the activity of the polypeptide in the absence of the test compound, wherein a change in the activity of the polypeptide in the presence of the test compound is indicative of a compound that modulates the activity of the polypeptide.

The invention further provides a method for screening a compound for effectiveness in altering expression of a target polynucleotide, wherein said target polynucleotide comprises a sequence selected from the group consisting of SEQ ID NO:15–28, the method comprising a) exposing a sample comprising the target polynucleotide to a compound, and b) detecting altered expression of the target polynucleotide.

The invention further provides a method for assessing toxicity of a test compound, said method comprising a) treating a biological sample containing nucleic acids with the test compound; b) hybridizing the nucleic acids of the treated biological sample with a probe comprising at least 20 contiguous nucleotides of a polynucleotide comprising a polynucleotide sequence selected from the group consisting of i) a polynucleotide sequence selected from the group consisting of SEQ ID NO:15–28, ii) a naturally occurring polynucleotide sequence having at least 70% sequence identity to a polynucleotide sequence selected from the group consisting of SEQ ID NO:15–28, iii) a polynucleotide sequence complementary to i), iv) a polynucleotide sequence complementary to ii), and v) an RNA equivalent of i)-iv). Hybridization occurs under conditions whereby a specific hybridization complex is formed between said probe and a target polynucleotide in the biological sample, said target polynucleotide comprising a polynucleotide sequence selected from the group consisting of i) a polynucleotide sequence selected from the group consisting of SEQ ID NO:15–28, ii) a naturally occurring polynucleotide sequence having at least 70% sequence identity to a polynucleotide sequence selected from the group consisting of SEQ ID NO:15–28, iii) a polynucleotide sequence complementary to i), iv) a polynucleotide sequence complementary to ii), and v) an RNA equivalent of i)–iv). Alternatively, the target polynucleotide comprises a fragment of a polynucleotide sequence selected from the group consisting of i)–v) above; c) quantifying the amount of hybridization complex; and d) comparing the amount of hybridization complex in the treated biological sample with the amount of hybridization complex in an untreated biological sample, wherein a difference in the amount of hybridization complex in the treated biological sample is indicative of toxicity of the test compound.

BRIEF DESCRIPTION OF THE TABLES

Table 1 shows polypeptide and nucleotide sequence identification numbers (SEQ ID NOs), clone identification numbers (clone IDs), cDNA libraries, and cDNA fragments used to assemble full-length sequences encoding HYENZ.

Table 2 shows features of each polypeptide sequence, including potential motifs, homologous sequences, and methods, algorithms, and searchable databases used for analysis of HYENZ.

Table 3 shows selected fragments of each nucleic acid sequence; the tissue-specific expression patterns of each nucleic acid sequence as determined by northern analysis; diseases, disorders, or conditions associated with these tissues; and the vector into which each cDNA was cloned.

Table 4 describes the tissues used to construct the cDNA libraries from which cDNA clones encoding HYENZ were isolated.

Table 5 shows the tools, programs, and algorithms used to analyze the polynucleotides and polypeptides of the invention, along with applicable descriptions, references, and threshold parameters.

DESCRIPTION OF THE INVENTION

Before the present proteins, nucleotide sequences, and methods are described, it is understood that this invention is not limited to the particular machines, materials and methods described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any machines, materials, and methods similar or equivalent to those described herein can be used to practice or test the present invention, the preferred machines, materials and methods are now described. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

Definitions

"HYENZ" refers to the amino acid sequences of substantially purified HYENZ obtained from any species, particularly a mammalian species, including bovine, ovine, porcine, murine, equine, and human, and from any source, whether natural, synthetic, semi-synthetic, or recombinant.

The term "agonist" refers to a molecule which intensifies or mimics the biological activity of HYENZ. Agonists may include proteins, nucleic acids, carbohydrates, small molecules, or any other compound or composition which modulates the activity of HYENZ either by directly interacting with HYENZ or by acting on components of the biological pathway in which HYENZ participates.

An "allelic variant" is an alternative form of the gene encoding HYENZ. Allelic variants may result from at least one mutation in the nucleic acid sequence and may result in altered mRNAs or in polypeptides whose structure or function may or may not be altered. A gene may have none, one, or many allelic variants of its naturally occurring form. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding HYENZ include those sequences with deletions, insertions, or substitutions of different nucleotides, resulting in a polypeptide the same as HYENZ or a polypeptide with at least one functional characteristic of HYENZ. Included within this definition are polymorphisms which may or may not be readily detectable using a particular oligonucleotide probe of the polynucleotide encoding HYENZ, and improper or unexpected hybridization to allelic variants, with a locus other than the normal chromosomal locus for the polynucleotide sequence encoding HYENZ. The encoded protein may also be "altered," and may contain deletions, insertions, or substitutions of amino acid residues which produce a silent change and result in a functionally equivalent HYENZ. Deliberate amino acid substitutions may be made on the basis of similarity in polarity, charge, solubility, hydrophobicity, hydrophilicity, and/or the amphipathic nature of the residues, as long as the biological or immunological activity of HYENZ is retained. For example, negatively charged amino acids may include aspartic acid and glutamic acid, and positively charged amino acids may include lysine and arginine. Amino acids with uncharged polar side chains having similar hydrophilicity values may include: asparagine and glutamine; and serine and threonine. Amino acids with uncharged side chains having similar hydrophilicity values may include: leucine, isoleucine, and valine; glycine and alanine; and phenylalanine and tyrosine.

The terms "amino acid" and "amino acid sequence" refer to an oligopeptide, peptide, polypeptide, or protein sequence, or a fragment of any of these, and to naturally occurring or synthetic molecules. Where "amino acid sequence" is recited to refer to a sequence of a naturally occurring protein molecule, "amino acid sequence" and like terms are not meant to limit the amino acid sequence to the complete native amino acid sequence associated with the recited protein molecule.

"Amplification" relates to the production of additional copies of a nucleic acid sequence. Amplification is generally carried out using polymerase chain reaction (PCR) technologies well known in the art.

The term "antagonist" refers to a molecule which inhibits or attenuates the biological activity of HYENZ. Antagonists may include proteins such as antibodies, nucleic acids, carbohydrates, small molecules, or any other compound or composition which modulates the activity of HYENZ either by directly interacting with HYENZ or by acting on components of the biological pathway in which HYENZ participates.

The term "antibody" refers to intact immunoglobulin molecules as well as to fragments thereof, such as Fab, $F(ab')_2$, and Fv fragments, which are capable of binding an epitopic determinant. Antibodies that bind HYENZ polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant" refers to that region of a molecule (i.e., an epitope) that makes contact with a particular antibody. When a protein or a fragment of a protein is used to immunize a host animal, numerous regions of the protein may induce the production of antibodies which bind specifically to antigenic determinants (particular regions or three-dimensional structures on the protein). An antigenic determinant may compete with the intact antigen (i.e., the immunogen used to elicit the immune response) for binding to an antibody.

The term "antisense" refers to any composition capable of base-pairing with the "sense" (coding) strand of a specific nucleic acid sequence. Antisense compositions may include DNA; RNA; peptide nucleic acid (PNA); oligonucleotides having modified backbone linkages such as phosphorothioates, methylphosphonates, or benzylphosphonates; oligonucleotides having modified sugar groups such as 2'-methoxyethyl sugars or 2'-methoxyethoxy sugars; or oligonucleotides having modified bases such as 5-methyl cytosine, 2'-deoxyuracil, or 7-deaza-2'-deoxyguanosine Antisense molecules may be produced by any method including chemical synthesis or transcription. Once introduced into a cell, the complementary antisense molecule base-pairs with a naturally occurring nucleic acid sequence produced by the cell to form duplexes which block either transcription or translation. The designation "negative" or "minus" can refer to the antisense strand, and the designation "positive" or "plus" can refer to the sense strand of a reference DNA molecule.

The term "biologically active" refers to a protein having structural, regulatory, or biochemical functions of a naturally occurring molecule. Likewise, "immunologically active" or "immunogenic" refers to the capability of the natural, recombinant, or synthetic HYENZ, or of any oligopeptide thereof, to induce a specific immune response in appropriate animals or cells and to bind with specific antibodies.

"Complementary" describes the relationship between two single-stranded nucleic acid sequences that anneal by base-pairing. For example, 5'-AGT-3' pairs with its complement, 3'-TCA-5'.

A "composition comprising a given polynucleotide sequence" and a "composition comprising a given amino acid sequence" refer broadly to any composition containing the given polynucleotide or amino acid sequence. The composition may comprise a dry formulation or an aqueous solution. Compositions comprising polynucleotide sequences encoding HYENZ or fragments of HYENZ may be employed as hybridization probes. The probes may be stored in freeze-dried form and may be associated with a stabilizing agent such as a carbohydrate. In hybridizations, the probe may be deployed in an aqueous solution containing salts (e g., NaCl), detergents (e.g., sodium dodecyl sulfate; SDS), and other components (e.g., Denhardt's solution, dry milk, salmon sperm DNA, etc.).

"Consensus sequence" refers to a nucleic acid sequence which has been subjected to repeated DNA sequence analysis to resolve uncalled bases, extended using the XL-PCR kit (PE Biosystems, Foster City Calif.) in the 5' and/or the 3' direction, and resequenced, or which has been assembled from one or more overlapping cDNA, EST, or genomic DNA fragments using a computer program for fragment assembly, such as the GELVIEW fragment assembly system (GCG, Madison Wis.) or Phrap University of Washington, Seattle Wash.). Some sequences have been both extended and assembled to produce the consensus sequence.

"Conservative amino acid substitutions" are those substitutions that are predicted to least interfere with the properties of the original protein, i.e., the structure and especially the function of the protein is conserved and not significantly changed by such substitutions. The table below shows amino acids which may be substituted for an original amino acid in a protein and which are regarded as conservative amino acid substitutions.

| Original Residue | Conservative Substitution |
|---|---|
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and or (c) the bulk of the side chain.

A "deletion" refers to a change in the amino acid or nucleotide sequence that results in the absence of one or more amino acid residues or nucleotides.

The term "derivative" refers to a chemically modified polynucleotide or polypeptide. Chemical modifications of a polynucleotide sequence can include, for example, replacement of hydrogen by an alkyl, acyl, hydroxyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

A "detectable label" refers to a reporter molecule or enzyme that is capable of generating a measurable signal and is covalently or noncovalently joined to a polynucleotide or polypeptide.

A "fragment" is a unique portion of HYENZ or the polynucleotide encoding HYENZ which is identical in sequence to but shorter in length than the parent sequence. A fragment may comprise up to the entire length of the defined sequence, minus one nucleotide/amino acid residue. For example, a fragment may comprise from 5 to 1000 contiguous nucleotides or amino acid residues. A fragment used as a probe, primer, antigen, therapeutic molecule, or for other purposes, may be at least 5, 10, 15, 16, 20, 25, 30, 40, 50, 60, 75, 100, 150, 250 or at least 500 contiguous nucleotides or amino acid residues in length. Fragments may be preferentially selected from certain regions of a molecule. For example, a polypeptide fragment may comprise a certain length of contiguous amino acids selected from the first 250 or 500 amino acids (or first 25% or 50% of a polypeptide) as shown in a certain defined sequence. Clearly these lengths are exemplary, and any length that is supported by the specification, including the Sequence Listing, tables, and figures, may be encompassed by the present embodiments.

A fragment of SEQ ID NO:15–28 comprises a region of unique polynucleotide sequence that specifically identities SEQ ID NO:15–28, for example, as distinct from any other sequence in the genome from which the fragment was obtained. A fragment of SEQ ID NO:15–28 is useful, for example, in hybridization and amplification technologies and in analogous methods that distinguish SEQ ID NO:15–28 from related polynucleotide sequences. The precise length of a fragment of SEQ ID NO:15–28 and the region of SEQ ID NO:15–28 to which the fragment corresponds are routinely determinable by one of ordinary skill in the art based on the intended purpose for the fragment.

A fragment of SEQ ID NO:1–14 is encoded by a fragment of SEQ ID NO:15–28. A fragment of SEQ ID NO:1–14 comprises a region of unique amino acid sequence that specifically identifies SEQ ID NO:1–14. For example, a fragment of SEQ ID NO:1–14 is useful as an immunogenic peptide for the development of antibodies that specifically recognize SEQ ID NO:1–14. The precise length of a fragment of SEQ ID NO:1–14 and the region of SEQ ID NO:1–14 to which the fragment corresponds are routinely determinable by one of ordinary skill in the art based on the intended purpose for the fragment.

A "full-length" polynucleotide sequence is one containing at least a translation initiation codon (e.g., methionine) followed by an open reading frame and a translation termination codon. A "full-length" polynucleotide sequence encodes a "full-length" polypeptide sequence.

"Homology" refers to sequence similarity or, interchangeably, sequence identity, between two or more polynucleotide sequences or two or more polypeptide sequences.

The terms "percent identity" and "% identity," as applied to polynucleotide sequences, refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences.

Percent identity between polynucleotide sequences may be determined using the default parameters of the CLUSTAL V algorithm as incorporated into the MEGA-LIGN version 3.12e sequence alignment program. This program is part of the LASERGENE software package, a suite of molecular biological analysis programs (DNASTAR, Madison Wis.). CLUSTAL V is described in Higgins, D. G. and P. M. Sharp (1989) CABIOS 5:151–153 and in Higgins, D. G. et al. (1992) CABIOS 8:189–191. For pairwise alignments of polynucleotide sequences, the default parameters are set as follows: Ktuple=2, gap penalty=5, window=4, and "diagonals saved"=4. The "weighted" residue weight table is selected as the default. Percent identity is reported by CLUSTAL V as the "percent similarity" between aligned polynucleotide sequences.

Alternatively, a suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403–410), which is available from several sources, including the NCBI, Bethesda, Md., and on the Internet at http://www.ncbi.nlm.nih.gov/

BLAST/. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at http://www.ncbi.nlm.nih.gov/gorf/b12.html. The "BLAST 2 Sequences" tool can be used for both blastn and blastp (discussed below). BLAST programs are commonly used with gap and other parameters set to default settings. For example, to compare two nucleotide sequences, one may use blastn with the "BLAST 2 Sequences" tool Version 2.0.12 (April-21-2000) set at default parameters. Such default parameters may be, for example:

Matrix: BLOSUM62
Reward for match: 1
Penalty for mismatch: −2
Open Gap: 5 and Extension Gap: 2 penalties
Gap×drop-off: 50
Expect: 10
Word Size: 11
Filler: on.

Percent identity may be measured over the length of an entire defined sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

Nucleic acid sequences that do not show a high degree of identity may nevertheless encode similar amino acid sequences due to the degeneracy of the genetic code. It is understood that changes in a nucleic acid sequence can be made using this degeneracy to produce multiple nucleic acid sequences that all encode substantially the same protein.

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods lake into account conservative amino acid substitutions. Such conservative substitutions, explained in more detail above, generally preserve the charge and hydrophobicity at the site of substitution, thus preserving the structure (and therefore function) of the polypeptide.

Percent identity between polypeptide sequences may be determined using the default parameters of the CLUSTAL V algorithm as incorporated into the MEGALIGN version 3.12e sequence alignment program (described and referenced above). For pairwise alignments of polypeptide sequences using CLUSTAL V, the default parameters are set as follows: Ktuple=1, gap penalty=3, window=5, and "diagonals saved"=5. The PAM250 matrix is selected as the default residue weight table. As with polynucleotide alignments, the percent identity is reported by CLUSTAL V as the "percent similarity" between aligned polypeptide sequence pairs.

Alternatively the NCBI BLAST software suite may be used. For example, for a pairwise comparison of two polypeptide sequences, one may use the "BLAST 2 Sequences" tool Version 2.0.12 (Apr. 21, 2000) with blastp set at default parameters. Such default parameters may be, for example:

Matrix: BLOSUM62
Open Gap: 11 and Extension Gap: 1 penalties
Gap×drop-off: 50
Expect: 10
Word Size: 3
Filter: on.

Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

"Human artificial chromosomes" (HACs) are linear microchromosomes which may contain DNA sequences of about 6 kb to 10 Mb in size, and which contain all of the elements required for chromosome replication, segregation and maintenance.

The term "humanized antibody" refers to an antibody molecule in which the amino acid sequence in the non-antigen binding regions has been altered so that the antibody more closely resembles a human antibody, and still retains its original binding ability.

"Hybridization" refers to the process by which a polynucleotide strand anneals with a complementary strand through base pairing under defined hybridization conditions. Specific hybridization is an indication that two nucleic acid sequences share a high degree of complementarity. Specific hybridization complexes form under permissive annealing conditions and remain hybridized after the "washing" step (s). The washing step(s) is particularly important in determining the stringency of the hybridization process, with more stringent conditions allowing less non-specific binding, i.e., binding between pairs of nucleic acid strands that are not perfectly matched. Permissive conditions for annealing of nucleic acid sequences are routinely determinable by one of ordinary skill in the art and may be consistent among hybridization experiments, whereas wash conditions may be varied among experiments to achieve the desired stringency, and therefore hybridization specificity. Permissive annealing conditions occur, for example, at 68° C. in the presence of about 6×SSC, about 1% (w/v) SDS, and about 100 µg/ml sheared, denatured salmon sperm DNA.

Generally, stringency of hybridization is expressed, in part, with reference to the temperature under which the wash step is carried out. Such wash temperatures are typically selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. An equation for calculating $T_m$ and conditions for nucleic acid hybridization are well known and can be found in Sambrook, J. et al., 1989, *Molecular Cloning: A Laboratory Manual,* 2nd ed., vol. 1–3, Cold Spring Harbor Press, Plainview N.Y.; specifically see volume 2, chapter 9.

High stringency conditions for hybridization between polynucleotides of the present invention include wash conditions of 68° C. in the presence of about 0.2×SSC and about 0.1% SDS, for 1 hour. Alternatively, temperatures of about 65° C., 60° C., 55° C., or 42° C. may be used. SSC concentration may be varied from about 0.1 to 2×SSC, with SDS being present at about 0.1%. Typically, blocking reagents are used to block non-specific hybridization. Such blocking reagents include, for instance, sheared and denatured salmon sperm DNA at about 100–200 µg/ml. Organic solvent, such as formamide at a concentration of about 35–50% v/v, may also be used under particular circumstances, such as for RNA:DNA hybridizations. Useful variations on these wash conditions will be readily apparent to those of ordinary skill in the art. Hybridization, particularly under high stringency conditions, may be suggestive of evolutionary similarity between the nucleotides. Such similarity is strongly indicative of a similar role for the nucleotides and their encoded polypeptides.

The term "hybridization complex" refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" and "addition" refer to changes in an amino acid or nucleotide sequence resulting in the addition of one or more amino acid residues or nucleotides, respectively.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

An "immunogenic fragment" is a polypeptide or oligopeptide fragment of HYENZ which is capable of eliciting an immune response when introduced into a living organism, for example, a mammal. The term "immunogenic fragment" also includes any polypeptide or oligopeptide fragment of HYENZ which is useful in any of the antibody production methods disclosed herein or known in the art.

The term "microarray" refers to an arrangement of a plurality of polynucleotides, polypeptides, or other chemical compounds on a substrate.

The terms "element" and "array element" refer to a polynucleotide, polypeptide, or other chemical compound having a unique and defined position on a microarray.

The term "modulate" refers to a change in the activity of HYENZ. For example, modulation may cause an increase or a decrease in protein activity, binding characteristics, or any other biological, functional, or immunological properties of HYENZ.

The phrases "nucleic acid" and "nucleic acid sequence" refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material.

"Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame.

"Peptide nucleic acid" (PNA) refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell.

"Post-translational modification" of an HYENZ may involve lipidation, glycosylation, phosphorylation, acetylation, racemization, proteolytic cleavage, and other modifications known in the art. These processes may occur synthetically or biochemically. Biochemical modifications will vary by cell type depending on the enzymatic milieu of HYENZ.

"Probe" refers to nucleic acid sequences encoding HYENZ, their complements, or fragments thereof, which are used to detect identical, allelic or related nucleic acid sequences. Probes are isolated oligonucleotides or polynucleotides attached to a detectable label or reporter molecule. Typical labels include radioactive isotopes, ligands, chemiluminescent agents, and enzymes. "Primers" are short nucleic acids, usually DNA oligonucleotides, which may be annealed to a target polynucleotide by complementary base-pairing. The primer may then be extended along the target DNA strand by a DNA polymerase enzyme. Primer pairs can be used for amplification (and identification) of a nucleic acid sequence, e.g., by the polymerase chain reaction (PCR).

Probes and primers as used in the present invention typically comprise at least 15 contiguous nucleotides of a known sequence. In order to enhance specificity, longer probes and primers may also be employed, such as probes and primers that comprise at least 20, 25, 30, 40, 50, 60, 70, 80, 90, 100, or at least 150 consecutive nucleotides of the disclosed nucleic acid sequences. Probes and primers may be considerably longer than these examples, and it is understood that any length supported by the specification, including the tables, figures, and Sequence Listing, may be used.

Methods for preparing and using probes and primers are described in the references, for example Sambrook, J. et al. (1989) *Molecular Cloning: A Laboratory Manual,* 2nd ed., vol. 1–3, Cold Spring Harbor Press, Plainview N.Y.; Ausubel, F. M. et al. (1987) *Current Protocols in Molecular Biology*, Greene Publ. Assoc. & Wiley-Intersciences, New York N.Y.; Innis, M. et al. (1990) *PCR Protocols, A Guide to Methods and Applications*, Academic Press, San Diego Calif. PCR primer pairs can be derived from a known sequence, for example, by using computer programs intended for that purpose such as Primer (Version 0.5, 1991, Whitehead Institute for Biomedical Research, Cambridge Mass.).

Oligonucleotides for use as primers are selected using software known in the art for such purpose. For example, OLIGO 4.06 software is useful for the selection of PCR primer pairs of up to 100 nucleotides each, and for the analysis of oligonucleotides and larger polynucleotides of up to 5,000 nucleotides from an input polynucleotide sequence of up to 32 kilobases. Similar primer selection programs have incorporated additional features for expanded capabilities. For example, the PrimOU primer selection program (available to the public from the Genome Center at University of Texas South West Medical Center, Dallas Tex.) is capable of choosing specific primers from megabase sequences and is thus useful for designing primers on a genome-wide scope. The Primer 3 primer selection program (available to the public from the Whitehead Institute/MIT Center for Genome Research, Cambridge Mass.) allows the user to input a "mispriming library," in which sequences to avoid as primer binding sites are user-specified. Primer3 is useful, in particular, for the selection of oligonucleotides for microarrays. (The source code for the latter two primer selection programs may also be obtained from their respective sources and modified to meet the user's specific needs.) The PrimeGen program (available to the public from the UK Human Genome Mapping Project Resource Centre, Cambridge UK) designs primers based on multiple sequence alignments, thereby allowing selection of primers that hybridize to either the most conserved or least conserved regions of aligned nucleic acid sequences. Hence, this program is useful for identification of both unique and conserved oligonucleotides and polynucleotide fragments. The oligonucleotides and polynucleotide fragments identified by any of the above selection methods are useful in hybridization technologies, for example, as PCR or sequencing primers, microarray elements, or specific probes to identify fully or partially complementary polynucleotides in a sample of nucleic acids. Methods of oligonucleotide selection are not limited to those described above.

A "recombinant nucleic acid" is a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques such as those described in Sambrook, supra. The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

Alternatively, such recombinant nucleic acids may be part of a viral vector, e.g., based on a vaccinia virus, that could be use to vaccinate a mammal wherein the recombinant nucleic acid is expressed, inducing a protective immunological response in the mammal.

A "regulatory element" refers to a nucleic acid sequence usually derived from untranslated regions of a gene and includes enhancers, promoters, introns, and 5' and 3' untranslated regions (UTRs). Regulatory elements interact with host or viral proteins which control transcription, translation, or RNA stability.

"Reporter molecules" are chemical or biochemical moieties used for labeling a nucleic acid, amino acid, or antibody. Reporter molecules include radionuclides; enzymes; fluorescent, chemiluminescent, or chromogenic agents; substrates; cofactors; inhibitors; magnetic particles; and other moieties known in the art.

An "RNA equivalent," in reference to a DNA sequence, is composed of the same linear sequence of nucleotides as the reference DNA sequence with the exception that all occurrences of the nitrogenous base thymine are replaced with uracil, and the sugar backbone is composed of ribose instead of deoxyribose.

The term "sample" is used in its broadest sense. A sample suspected of containing nucleic acids encoding HYENZ, or fragments thereof, or HYENZ itself, may comprise a bodily fluid; an extract from a cell, chromosome, organelle, or membrane isolated from a cell; a cell; genomic DNA, RNA, or cDNA, in solution or bound to a substrate; a tissue; a tissue print; etc.

The terms "specific binding" and "specifically binding" refer to that interaction between a protein or peptide and an agonist, an antibody, an antagonist, a small molecule, or any natural or synthetic binding composition. The interaction is dependent upon the presence of a particular structure of the protein, e.g., the antigenic determinant or epitope, recognized by the binding molecule. For example, if an antibody is specific for epitope "A," the presence of a polypeptide comprising the epitope A, or the presence of free unlabeled A, in a reaction containing free labeled A and the antibody will reduce the amount of labeled A that binds to the antibody.

The term "substantially purified" refers to nucleic acid or amino acid sequences that are removed from their natural environment and are isolated or separated, and are at least 60% free, preferably at least 75% free, and most preferably at least 90% free from other components with which they are naturally associated.

A "substitution" refers to the replacement of one or more amino acid residues or nucleotides by different amino acid residues or nucleotides, respectively.

"Substrate" refers to any suitable rigid or semi-rigid support including membranes, filters, chips, slides, wafers, fibers, magnetic or nonmagnetic beads, gels, tubing, plates, polymers, microparticles and capillaries. The substrate can have a variety of surface forms, such as wells, trenches, pins, channels and pores, to which polynucleotides or polypeptides are bound.

A "transcript image" refers to the collective pattern of gene expression by a particular cell type or tissue under given conditions at a given time.

"Transformation" describes a process by which exogenous DNA is introduced into a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, bacteriophage or viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "transgenic organism," as used herein, is any organism, including but not limited to animals and plants, in which one or more of the cells of the organism contains heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. The transgenic organisms contemplated in accordance with the present invention include bacteria, cyanobacteria, fungi, plants, and animals. The isolated DNA of the present invention can be introduced into the host by methods known in the art, for example infection, transfection, transformation or transconjugation. Techniques for transferring the DNA of the present invention into such organisms are widely known and provided in references such as Sambrook, J. et al. (1989), supra.

A "variant" of a particular nucleic acid sequence is defined as a nucleic acid sequence having at least 40% sequence identity to the particular nucleic acid sequence over a certain length of one of the nucleic acid sequences using blastn with the "BLAST 2 Sequences" tool Version 2.0.9 (May 07, 1999) set at default parameters. Such a pair of nucleic acids may show, for example, at least 50%, at least 60%, at least 70%, at least 80%, at least 85%, at least 90%, at least 95% or at least 98% or greater sequence identity over a certain defined length. A variant may be described as, for example, an "allelic" (as defined above), "splice," "species," or "polymorphic" variant. A splice variant may have significant identity to a reference molecule, but will generally have a greater or lesser number of polynucleotides due to alternative splicing of exons during mRNA processing. The corresponding polypeptide may possess additional functional domains or lack domains that are present in the reference molecule. Species variants are polynucleotide sequences that vary from one species to another. The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one nucleotide base. The presence of SNPs may be indicative of, for example, a certain population, a disease state, or a propensity for a disease state.

A "variant" of a particular polypeptide sequence is defined as a polypeptide sequence having at least 40% sequence identity to the particular polypeptide sequence over a certain length of one of the polypeptide sequences using blastp with the "BLAST 2 Sequences" tool Version 2.0.9 (May 7, 1999) set at default parameters. Such a pair of polypeptides may show, for example, at least 50%, at least 60%, at least 70%, at least 80%, at least 90%, at least 95%, or at least 98% or greater sequence identity over a certain defined length of one of the polypeptides.

The Invention

The invention is based on the discovery of new human hydrolytic enzymes (HYENZ), the polynucleotides encoding HYENZ, and the use of these compositions for the diagnosis, treatment, or prevention of neurological disorders, immune system disorders, genetic disorders, and cell proliferation disorders, including cancer.

Table 1 lists the Incyte clones used to assemble full length nucleotide sequences encoding HYENZ. Columns 1 and 2 show the sequence identification numbers (SEQ ID NOs) of the polypeptide and nucleotide sequences, respectively. Column 3 shows the clone IDs of the Incyte clones in which nucleic acids encoding each HYENZ were identified, and column 4 shows the cDNA libraries from which these clones were isolated. Column 5 shows Incyte clones and their corresponding cDNA libraries. Clones for which cDNA libraries are not indicated were derived from pooled cDNA libraries. In some cases, GenBank sequence identifiers are also shown in column 5. The Incyte clones, and GenBank cDNA sequences, where indicated, in column 5 were used to assemble the consensus nucleotide sequence of each HYENZ and are useful as fragments in hybridization technologies.

The columns of Table 2 show various properties of each of the polypeptides of the invention: column 1 references the SEQ ID NO; column 2 shows the number of amino acid residues in each polypeptide; column 3 shows potential phosphorylation sites; column 4 shows potential glycosylation sites; column 5 shows the amino acid residues comprising signature sequences and motifs; column 6 shows homologous sequences as identified by BLAST analysis; and column 7 shows analytical methods and in some cases, searchable databases to which the analytical methods were applied. The methods of column 7 were used to characterize each polypeptide through sequence homology and protein motifs.

The columns of Table 3 show the tissue-specificity and diseases, disorders, or conditions associated with nucleotide sequences encoding HYENZ. The first column of Table 3 lists the nucleotide SEQ ID NOs. Column 2 lists fragments of the nucleotide sequences of column 1. These fragments are useful, for example, in hybridization or amplification technologies to identify SEQ ID NO:15–28 and to distinguish between SEQ ID NO:15–28 and related polynucleotide sequences. The polypeptides encoded by these fragments are useful, for example, as immunogenic peptides. Column 3 lists tissue categories which express HYENZ as a fraction of total tissues expressing HYENZ. Column 4 lists diseases, disorders, or conditions associated with those tissues expressing HYENZ as a fraction of total tissues expressing HYENZ. Column 5 lists the vectors used to subclone each cDNA library.

The columns of Table 4 show descriptions of the tissues used to construct the cDNA libraries from which cDNA clones encoding HYENZ were isolated. Column 1 references the nucleotide SEQ ID NOs, column 2 shows the cDNA libraries from which these clones were isolated, and column 3 shows the tissue origins and other descriptive information relevant to the cDNA libraries in column 2.

SEQ ID NO:19 maps to chromosome 1 within the interval from 75.3 to 81.6 centiMorgans. This interval also contains a gene associated with T cell acute lymphocytic leukemia 1. This interval also contains ESTs associated with various hydrolytic enzymes, such as carnitine palmitoyltransferase 1 and fatty acid amide hydrolase (FAAH).

The invention also encompasses HYENZ variants. A preferred HYENZ variant is one which has at least about 80%, or alternatively at least about 90%, or even at least about 95% amino acid sequence identity to the HYENZ amino acid sequence, and which contains at least one functional or structural characteristic of HYENZ.

The invention also encompasses polynucleotides which encode HYENZ. In a particular embodiment, the invention encompasses a polynucleotide sequence comprising a sequence selected from the group consisting of SEQ ID NO:15–28, which encodes HYENZ. The polynucleotide sequences of SEQ ID NO:15–28, as presented in the Sequence Listing, embrace the equivalent RNA sequences, wherein occurrences of the nitrogenous base thymine are replaced with uracil, and the sugar backbone is composed of ribose instead of deoxyribose.

The invention also encompasses a variant of a polynucleotide sequence encoding HYENZ. In particular, such a variant polynucleotide sequence will have at least about 70%, or alternatively at least about 85%, or even at least about 95% polynucleotide sequence identity to the polynucleotide sequence encoding HYENZ. A particular aspect of the invention encompasses a variant of a polynucleotide sequence comprising a sequence selected from the group consisting of SEQ ID NO:15–28 which has at least about 70%, or alternatively at least about 85%, or even at least about 95% polynucleotide sequence identity to a nucleic acid sequence selected from the group consisting of SEQ ID NO: 15–28. Any one of the polynucleotide variants described above can encode an amino acid sequence which contains at least one functional or structural characteristic of HYENZ.

It will be appreciated by those skilled in the art that as a result of the degeneracy of the genetic code, a multitude of polynucleotide sequences encoding HYENZ, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring HYENZ, and all such variations are to be considered as being specifically disclosed.

Although nucleotide sequences which encode HYENZ and its variants are generally capable of hybridizing to the nucleotide sequence of the naturally occurring HYENZ under appropriately selected conditions of stringency, it may be advantageous to produce nucleotide sequences encoding HYENZ or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host, Other reasons for substantially altering the nucleotide sequence encoding HYENZ and its derivatives without altering the encoded amino acid sequences include the production of RNA transcripts having more desirable properties, such as a greater half-life, than transcripts produced from the naturally occurring sequence.

The invention also encompasses production of DNA sequences which encode HYENZ and HYENZ derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding HYENZ or any fragment thereof.

Also encompassed by the invention are polynucleotide sequences that are capable of hybridizing to the claimed polynucleotide sequences, and, in particular, to those shown in SEQ ID NO:15–28 and fragments thereof under various conditions of stringency. (See, e.g., Wahl, G. M. and S. L. Berger (1987) Methods Enzymol. 152:399–407; Kimmel, A. R. (1987) Methods Enzymol. 152:507–511.) Hybridization conditions, including annealing and wash conditions, are described in "Definitions."

Methods for DNA sequencing are well known in the art and may be used to practice any of the embodiments of the invention. The methods may employ such enzymes as the Klenow fragment of DNA polymerase 1, SEQUENASE (US Biochemical, Cleveland Ohio), Taq polymerase (PE Biosystems, Foster City Calif.), thermostable T7 polymerase (Amersham Pharmacia Biotech, Piscataway N.J.), or combinations of polymerases and proofreading exonucleases such as those found in the ELONGASE amplification system (Life Technologies, Gaithersburg Md.). Preferably, sequence preparation is automated with machines such as the MICROLAB 2200 liquid transfer system (Hamilton, Reno Nev.), PTC200 thermal cycler (MJ Research, Watertown Mass.) and ABI CATALYST 800 thermal cycler (PE Biosystems). Sequencing is then carried out using either the ABI 373 or 377 DNA sequencing system (PE Biosystems), the MEGABACE 1000 DNA sequencing system (Molecular Dynamics, Sunnyvale Calif.), or other systems known in the art. Mm resulting sequences are analyzed using a variety of algorithms which are well known in the art. (See, e.g., Ausubel, F. M. (1997) *Short Protocols in Molecular Biology*, John Wiley & Sons, New York N.Y., unit 7.7; Meyers, R. A (1995) *Molecular Biology and Biotechnology*, Wiley VCH, New York N.Y., pp. 856–853.)

The nucleic acid sequences encoding HYENZ may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318–322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 1:111–119.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker, J. D. et al. (1991) Nucleic Acids Res. 19:3055–3060). Additionally, one may use PCR, nested primers, and PROMOTERFINDER libraries (Clontech Palo Alto Calif.) to walk genomic DNA. This procedure avoids the need to screen libraries and is useful in finding intron/exon junctions. For all PCR-based methods, primers may be designed using commercially available software, such as OLIGO 4.06 Primer Analysis software (National Biosciences, Plymouth Minn.) or another appropriate program, to be about 22 to 30 nucleotides in length, to have a GC content of about 50% or more, and to anneal to the template at temperatures of about 68° C. to 72° C.

When screening for full-length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Gnomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., GENOTYPER and SEQUENCE NAVIGATOR, PE Biosystems), and the entire process from loading of samples to computer analysis and electronic data display may be computer controlled Capillary electrophoresis is especially preferable for sequencing small DNA fragments which may be present in limited amounts in a particular sample.

In another embodiment of the invention, polynucleotide sequences or fragments thereof which encode HYENZ may be cloned in recombinant DNA molecules that direct expression of HYENZ, or fragments or functional equivalents thereof, in appropriate host cells. Due to the inherent degeneracy of the genetic code, other DNA sequences which encode substantially the same or a functionally equivalent amino acid sequence may be produced and used to express HYENZ.

The nucleotide sequences of the present invention can be engineered using methods generally known in the art in order to alter HYENZ-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

The nucleotides of the present invention may be subjected to DNA shuffling techniques such as MOLECULAR-BREEDING (Maxygen Inc., Santa Clara Calif.; described in U.S. Pat. No. 5,837,458; Chang, C.-C. et al. (1999) Nat. Biotechnol. 17:793–797; Christians, F. C. et al. (1999) Nat. Biotechnol. 17:259–264; and Crameri, A. et al. (1996) Nat. Biotechnol. 14:315–319) to alter or improve the biological properties of HYENZ, such as its biological or enzymatic activity or its ability to bind to other molecules or compounds. DNA shuffling is a process by which a library of gene variants is produced using PCR-mediated recombination of gene fragments. The library is then subjected to selection or screening procedures that identify those gene variants with the desired properties. These preferred variants may then be pooled and further subjected to recursive rounds of DNA shuffling and selection/screening. Thus, genetic diversity is created through "artificial" breeding and rapid molecular evolution. For example, fragments of a single gene containing random point mutations may be recombined, screened, and then reshuffled until the desired properties are optimized. Alternatively, fragments of a given gene may be recombined with fragments of homologous genes in the same gene family, either from the same or different species, thereby maximizing the genetic diversity of multiple naturally occurring genes in a directed and controllable manner.

In another embodiment, sequences encoding HYENZ may be synthesized, in whole or in part, using chemical methods well known in the art. (See, e.g., Caruthers, M. H. et al. (1980) Nucleic Acids Symp. Ser. 7:215–223; Horn, T. et al. (1980) Nucleic Acids Symp. Ser. 7:225–232.) Alternatively, HYENZ itself or a fragment thereof may be synthesized using chemical methods. For example, peptide synthesis can be performed using various solution-phase or solid-phase techniques. (See, e.g., Creighton, T. (1984) Proteins. Structures and Molecular Properties, WH Freeman, New York N.Y., pp. 55–60; and Roberge, J. Y. et al. (1995) Science 269:202–204.) Automated synthesis may be achieved using the ABI 431 A peptide synthesizer (PE Biosystems). Additionally, the amino acid sequence of HYENZ, or any part thereof, may be altered during direct synthesis and/or combined with sequences from other proteins, or any part thereof, to produce a variant polypeptide or a polypeptide having a sequence of a naturally occurring polypeptide.

The peptide may be substantially purified by preparative high performance liquid chromatography. (See, e.g., Chiez, R. M. and F. Z. Regnier (1990) Methods Enzymol. 182:392–421.) The composition of the synthetic peptides may be confirmed by amino acid analysis or by sequencing. (See, e.g., Creighton, supra, pp. 28–53.)

In order to express a biologically active HYENZ, the nucleotide sequences encoding HYENZ or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding HYENZ. Such elements may vary in their strength and specificity. Specific initiation signals may also be used to achieve more efficient translation of sequences encoding HYENZ. Such signals include the ATG initiation codon and adjacent sequences, e.g. the Kozak sequence. In cases where sequences encoding HYENZ and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20:125–162.)

Methods which are well known to those skilled in the art may be used to construct expression vectors containing sequences encoding HYENZ and appropriate transcriptional and translational control elements. These methods include in vitro recombinant DNA techniques, synthetic techniques, and in vivo genetic recombination (See, e.g., Sambrook, J. et al. (1989) Molecular Cloning, A Laboratory Manual, Cold Spring Harbor Press, Plainview N.Y., ch. 4, 8, and 16–17; Ausubel, F. M. et al. (1995) Current Protocols in Molecular Biology, John Wiley & Sons, New York N.Y., ch 9, 13, and 16.)

A variety of expression vector/host systems may be utilized to contain and express sequences encoding HYENZ. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus, CaMV, or tobacco mosaic virus, TMV) or with bacterial expression vectors (e.g., Ti or pBR322 plasmids); or animal cell systems. (See, e.g., Sambrook, supra; Ausubel, supra; Van Heeke, G. and S. M. Schuster (1989) J. Biol. Chem. 264:5503–5509; Bitter, G. A. et al. (1987) Methods Enzymol. 153:516–544; Scorer, C. A et al. (1994) Bio/Technology 12:181–184; Engelhard, E. K. et al. (1994) Proc. Natl. Acad. Sci. USA 91:3224–3227; Sandig, V. et al. (1996) Hum. Gene Ther. 7:1937–1945; Takarnatsu, N. (1987) EMBO J. 6:307–311; Coruzzi, G. et al. (1984) EMBO J. 3:1671–1680; Broglie, R. et al. (1984) Science 224:838–843; Winter, J. et al. (1991) Results Probl. Cell Differ. 17:85–105; The McGraw Hill Yearbook of Science and Technology (1992) McGraw Hill, New York N.Y., pp. 191–196; Logan, J. and T. Shenk (1984) Proc. Natl. Acad. Sci. USA 81:3655–3659; and Harrington, J. J. et al. (1997) Nat. Genet. 15:345–355.) Expression vectors derived from retroviruses, adenoviruses, or herpes or vaccinia viruses, or from various bacterial plasmids, may be used for delivery of nucleotide sequences to the targeted organ, tissue, or cell population. (See, e.g., Di Nicola, M. et al. (1998) Cancer Gen. Ther. 5(6):350–356; Yu, M. et al. (1993)

Proc. Natl. Acad. Sci. USA 90(13):6340–6344; Buller, R. M. et al. (1985) Nature 317(6040):813–815; McGregor, D. P. et al. (1994) Mol. Immunol. 31(3):219–226; and Verma, T. M. and N. Somia (1997) Nature 389:239–242.) The invention is not limited by the host cell employed.

In bacterial systems, a number of cloning and expression vectors may be selected depending upon the use intended for polynucleotide sequences encoding HYENZ. For example, routine cloning, subcloning, and propagation of polynucleotide sequences encoding HYENZ can be achieved using a multifunctional E. coli vector such as PBLUESCRIPT (Stratagene, La Jolla Calif.) or PSPORT1 plasmid (Life Technologies). Ligation of sequences encoding HYENZ into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, cg., Van Heeke, G. and S. M. Schuster (1989) J. Biol. Chen 264:5503–5509.) When large quantities of HYENZ are needed e.g. for the production of antibodies, vectors which direct high level expression of HYENZ may be used. For example, vectors containing the strong, inducible T5 or 17 bacteriophage promoter may be used.

Yeast expression systems may be used for production of HYENZ. A number of vectors containing constitutive or inducible promoters, such as alpha factor, alcohol oxidase, and PGH promoters, may be used in the yeast *Saccharomyces cerevisiae* or *Pichia pastoris*. In addition, such vectors direct either the secretion or intracellular retention of expressed proteins and enable integration of foreign sequences into the host genome for stable propagation. (See, e.g., Ausubel, 1995, supra; Bitter, supra; and Scorer, supra.)

Plant systems may also be used for expression of HYENZ. Transcription of sequences encoding HYENZ may be driven viral promoters, e.g., the 355 and 19S promoters of CAMV used alone or in combination with the omega leader sequence from TMV (Takamatsu, N. (1987) EMBO J. 6:307–311). Alternatively, plant promoters such as the small subunit of RUBISCO or heat shock promoters may be used (See, e.g., Coruzzi, supra; Broglie, supra; and Winter, supra.) These constructs can be introduced into plant cells by direct DNA transformation or pathogen-mediated transfection (See, e.g., *The McGraw Hill Yearbook of Science and Technology* (1992) McGraw Hill, New York N.Y., pp. 191–196.)

In mammalian cells, a number of viral-based expression systems may be utilized. In cases where an adenovirus is used as an expression vector, sequences encoding HYENZ may be ligated into an adenovirus transcription/translation complex consisting of the late promoter and tripartite leader sequence. Insertion in a non-essential E1 or E3 region of the viral genome may be used to obtain infective virus which expresses HYENZ in host cells. (See, e.g., Logan, J. and T. Shenk (1984) Proc. Natl. Acad. Sci. USA 81:3655–3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACS) may also be employed to deliver larger fragments of DNA than can be contained in and expressed from a plasmid HACs of about 6 kb to 10 Mb are constructed and delivered via conventional delivery methods (liposomes, polycationic amino polymers, or vesicles) for therapeutic purposes. (See, e.g., Harrington, J. J. et al. (1997) Nat. Genet. 15:345–355.)

For long term production of recombinant proteins in mammalian systems, stable expression of HYENZ in cell lines is preferred. For example, sequences encoding HYENZ can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk$^-$ and apr$^-$ cells, respectively. (See, e.g., Wigler, M. et al. (1977) Cell 11:223–232; Lowy, I. et al. (1980) Cell 22:817–823.) Also, antimetabolite, antibiotic, or herbicide resistance can be used as the basis for selection. For example, dhfr confers resistance to methotrexate; neo confers resistance to the aminoglycosides neomycin and G418; and als and pat confer resistance to chlorosulfuron and phosphinotricin acetyltransferase, respectively. (See, e.g., Wigler, M. et al. (1980) Proc. Natl. Acad. Sci. USA 77:3567–3570; Colbere-Garapin, F. et al. (1981) J. Mol. Biol. 150:1–14.) Additional selectable genes have been described, e.g., trpB and hisD, which alter cellular requirements for metabolites. (See, e.g., Hartman, S. C. and R. C. Mulligan (1988) Proc. Natl. Acad. Sci. USA 85:8047–8051.) Visible markers, e.g., anthocyanins, green fluorescent proteins (GFP; Clontech), βglucuronidase and its substrate β-glucuronide, or luciferase and its substrate luciferin may be used. These markers can be used not only to identify transformants, but also to quantify the amount of transient or stable protein expression attributable to a specific vector system. (See, e.g., Rhodes, C. A. (1995) Methods Mol. Biol. 55:121–131.)

Although the presence/absence of marker gene expression suggests that the gene of interest is also present, the presence and expression of the gene may need to be confirmed. For example, if the sequence encoding HYENZ is inserted within a marker gene sequence, transformed cells containing sequences encoding HYENZ can be identified by the absence of marker gene function. Alternatively, a marker gene can be placed in tandem with a sequence encoding HYENZ under the control of a single promoter. Expression of the marker gene in response to induction or selection usually indicates expression of the tandem gene as well.

In general, host cells that contain the nucleic acid sequence encoding HYENZ and that express HYENZ may be identified by a variety of procedures known to those of skill in the art. These procedures include, but are not limited to, DNA—DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of HYENZ using either specific polyclonal or monoclonal antibodies are known in the art Examples of such techniques include enzyme-linked immunosorbent assays (ELISAs), radioimmunoassays (RIAs), and fluorescence activated cell sorting (SACS). A two-site, monoclonal-based immunoassay utilizing monoclonal antibodies reactive to two non-interfering epitopes on HYENZ is preferred, but a competitive binding assay may be employed. These and other assays are well known in the art. (See, e.g., Hampton, R. et al. (1990) *Serological Methods, a Laboratory Manual*, APS Press, St. Paul Minn., Sect. IV; Coligan, J. E. et al. (1997) *Current Protocols in Immunology*, Greene Pub. Associates and Wiley-Interscience, New York N.Y.; and Pound, J. D. (1998) *Immunochemical Protocols*, Humana Press, Totowa N.J.)

A wide variety of labels and conjugation techniques are known by those skilled in the art and may be used in various nucleic acid and amino acid assays. Means for producing labeled hybridization or PCR probes for detecting sequences related to polynucleotides encoding HYENZ include oligolabeling, nick translation, end-labeling, or PCR amplification using a labeled nucleotide. Alternatively, the sequences encoding HYENZ, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Amersham Pharmacia Biotech, Promega (Madison Wis.), and US Biochemical. Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding HYENZ may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode HYENZ may be designed to contain signal sequences which direct secretion of HYENZ through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" or "pro" form of the protein may also be used to specify protein targeting, folding, and/or activity. Different host cells which have specific cellular machinery and characteristic mechanisms for post-translational activities (e.g., CHO, HeLa, MDCK, HEK293, and WI38) are available from the American Type Culture Collection (ATCC, Manassas Va.) and may be chosen to ensure the correct modification and processing of the foreign protein.

In another embodiment of the invention, natural, modified, or recombinant nucleic acid sequences encoding HYENZ may be ligated to a heterologous sequence resulting in translation of a fusion protein in any of the aforementioned host systems. For example, a chimeric HYENZ protein containing a heterologous moiety that can be recognized by a commercially available antibody may facilitate the screening of peptide libraries for inhibitors of HYENZ activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the HYENZ encoding sequence and the heterologous protein sequence, so that HYENZ may be cleaved away from the heterologous moiety following purification. Methods for fusion protein expression and purification are discussed in Ausubel (1995, supra, ch. 10). A variety of commercially available kits may also be used to facilitate expression and purification of fusion proteins.

In a further embodiment of the invention, synthesis of radiolabeled HYENZ may be achieved in vitro using the TNT rabbit reticulocyte lysate or wheat germ extract system (Promega). These systems couple transcription and translation of protein-coding sequences operably associated with the T7, T3, or SP6 promoters. Translation takes place in the presence of a radiolabeled amino acid precursor, for example, $^{35}$S-methionine.

HYENZ of the present invention or fragments thereof may be used to screen for compounds that specifically bind to HYENZ. At least one and up to a plurality of test compounds may be screened for specific binding to HYENZ. Examples of test compounds include antibodies, oligonucleotides, proteins (e.g., receptors), or small molecules.

In one embodiment, the compound thus identified is closely related to the natural ligand of HYENZ, e.g., a ligand or fragment thereof, a natural substrate, a structural or functional mimetic, or a natural binding partner. (See, e.g., Coligan, J. E. et al. (1991) *Current Protocols in immunology* 1(2): Chapter 5.) Similarly, the compound can be closely related to the natural receptor to which HYENZ binds, or to at least a fragment of the receptor, e.g., the ligand binding site. In either case, the compound can be rationally designed using known techniques. In one embodiment, screening for these compounds involves producing appropriate cells which express HYENZ, either as a secreted protein or on the cell membrane. Preferred cells include cells from mammals, yeast, *Drosophila*, or *E. coli*. Cells expressing HYENZ or cell membrane fractions which contain HYENZ are then contacted with a test compound and binding, stimulation, or inhibition of activity of either HYENZ or the compound is analyzed.

An assay may simply test binding of a test compound to the polypeptide, wherein binding is detected by a fluorophore, radioisotope, enzyme conjugate, or other detectable label. For example, the assay may comprise the steps of combining at least one test compound with HYENZ, either in solution or affixed to a solid support, and detecting the binding of HYENZ to the compound. Alternatively, the assay may detect or measure binding of a test compound in the presence of a labeled competitor. Additionally, the assay may be carried out using cell-free preparations, chemical libraries, or natural product mixtures, and the test compound (s) may be free in solution or affixed to a solid support.

HYENZ of the present invention or fragments thereof may be used to screen for compounds that modulate the activity of HYENZ. Such compounds may include agonists, antagonists, or partial or inverse agonists. In one embodiment, an assay is performed under conditions permissive for HYENZ activity, wherein HYENZ is combined with at least one test compound, and the activity of HYENZ in the presence of a test compound is compared with the activity of HYENZ in the absence of the test compound. A change in the activity of HYENZ in the presence of the test compound is indicative of a compound that modulates the activity of HYENZ. Alternatively, a test compound is combined with an in vitro or cell-free system comprising HYENZ under conditions suitable for HYENZ activity, and the assay is performed. In either of these assays, a test compound which modulates the activity of HYENZ may do so indirectly and need not come in direct contact with the test compound. At least one and up to a plurality of test compounds may be screened.

In another embodiment, polynucleotides encoding HYENZ or their mammalian homologs may be "knocked out" in an animal model system using homologous recombination in embryonic stem (ES) cells. Such techniques are well known in the art and are useful for the generation of animal models of human disease. (See, e.g., U.S. Pat. No. 5,175,383 and U.S. Pat. No. 5,767,337.) For example, mouse ES cells, such as the mouse 129/SvJ cell line, are derived from the early mouse embryo and grown in culture. The ES cells are transformed with a vector containing the gene of interest disrupted by a marker gene, e.g., the neomycin phosphotransferase gene (neo; Capecchi, M. R. (1989) Science 244:1288–1292). The vector integrates into the corresponding region of the host genome by homologous recombination. Alternatively, homologous recombination takes place using the Cre-loxP system to knockout a gene of interest in a tissue- or developmental stage-specific manner (Marth, J. D. (1996) Clin. Invest 97:1999–2002; Wagner, CU. et al. (1997) Nucleic Acids Res. 25:43234330). Transformed ES cells are identified and microinjected into mouse cell blastocysts such as those from the C57BL/6 mouse strain. The blastocysts are surgically transferred to pseudopregnant dams, and the resulting chimeric progeny are genotyped and bred to produce heterozygous or homozygous strains. Transgenic animals thus generated may be tested with potential therapeutic or toxic agents.

Polynucleotides encoding HYENZ may also be manipulated in vitro in ES cells derived from human blastocysts. Human ES cells have the potential to differentiate into at least eight separate cell lineages including endoderm, mesoderm, and ectodermal cell types. These cell lineages differentiate into, for example, neural cells, hematopoietic lineages, and cardiomyocytes (Thomson, J. A. et al. (1998) Science 282:1145–1147).

Polynucleotides encoding HYENZ can also be used to create "knockin" humanized animals (pigs) or transgenic animals (mice or rats) to model human disease. With knockin technology, a region of a polynucleotide encoding HYENZ is injected into animal ES cells, and the injected sequence integrates into the animal cell genome. Transformed cells are injected into blastulae, and the blastulae are implanted as described above. Transgenic progeny or inbred lines are studied and treated with potential pharmaceutical agents to obtain information on treatment of a human disease. Alternatively, a mammal inbred to overexpress HYENZ, e.g., by secreting HYENZ in its milk, may also serve as a convenient source of that protein (Janne, J. et al. (1998) Biotechnol. Annu. Rev. 4:55–74).

Therapeutics

Chemical and structural similarity, e.g., in the context of sequences and motifs, exists between regions of HYENZ and hydrolytic enzymes. In addition, the expression of HYENZ is closely associated with cancerous, cardiovascular, dermatologic, developmental, endocrine, gastrointestinal, hematopoietic/immune, inflamed, nervous, proliferating, reproductive, and urologic tissues. Therefore, HYENZ appears to play a role in neurological disorders, immune system disorders, genetic disorders, and cell proliferation disorders, including cancer. In the treatment of disorders associated with increased HYENZ expression or activity, it is desirable to decrease the expression or activity of HYENZ. In the treatment of disorders associated with decreased HYENZ expression or activity, it is desirable to increase the expression or activity of HYENZ.

Therefore, in one embodiment, HYENZ or a fragment or derivative thereof may be administered to a subject to treat or prevent a disorder associated with decreased expression or activity of HYENZ. Examples of such disorders include, but are not limited to, a neurological disorder, such as epilepsy, ischemic cerebrovascular disease, stroke, cerebral neoplasms, Alzheimer's disease, Pick's disease, Huntington's disease, dementia, Parkinson's disease and other extrapyramidal disorders, amyotrophic lateral sclerosis and other motor neuron disorders, progressive neural muscular atrophy, retinitis pigmentosa, hereditary ataxias, multiple sclerosis and other demyelinating diseases, bacterial and viral meningitis, brain abscess, subdural empyema, epidural abscess, suppurative intracranial thrombophlebitis, myelitis and radiculitis, viral central nervous system disease; prion diseases including kuru, Creutzfeldt-Jakob disease, and Gerstmann-Straussler-Scheinker syndrome; fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorder of the central nervous system, cerebral palsy, a neuroskeletal disorder, an autonomic nervous system disorder, a cranial nerve disorder, a spinal cord disease, muscular dystrophy and other neuromuscular disorder, a peripheral nervous system disorder, dermatomyositis and polymyositis; inherited, metabolic, endocrine, and toxic myopathy; myasthenia gravis, periodic paralysis; a mental disorder including mood, anxiety, and schizophrenic disorders; seasonal affective disorder (SAD); akathesia, amnesia, catatonia, diabetic neuropathy, tardive dyskinesia, dystonias, paranoid psychoses, postherpetic neuralgia, and Tourette's disorder; an immune system disorder, such as inflammation, actinic keratosis, acquired immunodeficiency syndrome (AIDS), Addison's disease, adult respiratory distress syndrome, allergies, ankylosing spondylitis, amyloidosis, anemia, arteriosclerosis, asthma, atherosclerosis, autoimmune hemolytic anemia, autoimmune thyroiditis, bronchitis, bursitis, cholecystitis, cirrhosis, contact dermatitis, Crohn's disease, atopic dermatitis, dermatomyositis, diabetes mellitus, emphysema, erythroblastosis fetalis, erythema nodosum, atrophic gastritis, glomerulonephritis, Goodpasture's syndrome, gout, Graves' disease, Hashimoto's thyroiditis, paroxysmal nocturnal hemoglobinuria, hepatitis, hypereosinophilia, irritable bowel syndrome, episodic lymphopenia with lymphocytotoxins, mixed connective tissue disease (MCTD), multiple sclerosis, myasthenia gravis, myocardial or pericardial inflammation, myelofibrosis, osteoarthritis, osteoporosis, pancreatitis, polycytheriia vera, polymyositis, psoriasis, Reiter's syndrome, rheumatoid arthritis, scleroderma, Sjögren's syndrome, systemic anaphylaxis, systemic lupus erythematosus, systemic sclerosis, primary thrombocythemia, thrombocytopenic purpura, ulcerative colitis, uveitis, Werner syndrome, complications of cancer, hemodialysis, and extracorporeal circulation, trauma, and hematopoietic cancer including lymphoma, leukemia, and myeloma; a genetic disorder, such as GM1-gangliosidosis, Niemann-Pick disease, adrenoleukodystrophy, Alport's syndrome, choroideremia, Duchenne and Becker muscular dystrophy, Down's syndrome, cystic fibrosis, chronic granulomatous disease, Gaucher's disease, Huntingion's chorea, Marfan's syndrome, muscular dystrophy, myotonic dystrophy, pycnodysostosis, Refsum's syndrome, retinoblastoma, sickle cell anemia, thalassemia, Werner syndrome, von Willebrand's disease, von Hippel-Lindau syndrome, Wims' tumor, Zellweger syndrome, peroxisomal acyl-CoA oxidase deficiency, peroxisomal thiolase deficiency, peroxisomal bifunctional protein deficiency, mitochondrial carnitine palmitoyl transferase and carnitine deficiency, mitochondrial very-long-chain acyl-CoA dehydrogenase deficiency, mitochondrial medium-chain acyl-CoA dehydrogenase deficiency, mitochondrial short-chain acyl-CoA dehydrogenase deficiency, mitochondrial electron transport flavoprotein and electron transport flavoprotein:ubiquinone oxidoreductase deficiency, mitochondrial trifunctional protein deficiency, and mitochondrial short-chain 3-hydroxyacyl-CoA dehydrogenase deficiency; and a cell proliferation disorder, such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, In particular, a cancer of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In another embodiment, a vector capable of expressing HYENZ or a fragment or derivative thereof may be administered to a subject to treat or prevent a disorder associated with decreased expression or activity of HYENZ including, but not limited to, those described above.

In a further embodiment, a composition comprising a substantially purified HYENZ in conjunction with a suitable pharmaceutical carrier may be administered to a subject to treat or prevent a disorder associated with decreased expression or activity of HYENZ including, but not limited to, those provided above.

In still another embodiment, an agonist which modulates the activity of HYENZ may be administered to a subject to treat or prevent a disorder associated with decreased expression or activity of HYENZ including, but not limited to, those listed above.

In a further embodiment, an antagonist of HYENZ may be administered to a subject to treat or prevent a disorder associated with increased expression or activity of HYENZ. Examples of such disorders include, hut are not limited to, those neurological disorders, immune system disorders, genetic disorders, and cell proliferation disorders, including cancer described above. In one aspect, an antibody which specifically binds HYENZ may be used directly as an antagonist or indirectly as a targeting or delivery mechanism for bringing a pharmaceutical agent to cells or tissues which express HYENZ.

In an additional embodiment, a vector expressing the complement of the polynucleotide encoding HYENZ may be administered to a subject to treat or prevent a disorder associated with increased expression or activity of HYENZ including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of HYENZ may be produced using methods which are generally known in the art. In particular, purified HYENZ may be used to produce antibodies or to screen libraries of pharmaceutical agents to identify those which specifically bind HYENZ. Antibodies to HYENZ may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are generally preferred for therapeutic use.

For the production of antibodies, various hosts including goats, rabbits, rats, mice, humans, and others may be immunized by injection with HYENZ or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to HYENZ have an amino acid sequence consisting of at least about 5 amino acids, and generally will consist of at least about 10 amino acids. It is also preferable that these oligopeptides, peptides, or fragments are identical to a portion of the amino acid sequence of the natural protein. Short stretches of HYENZ amino acids may be fused with those of another protein, such as KLH, and antibodies to the chimeric molecule may be produced.

Monoclonal antibodies to HYENZ may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R. J. et al. (1983) Proc. Natl. Acad. Sci. USA 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. USA 81:6851–6855; Neuberger, M. S. et al. (1984) Nature 312:604–608; and Takeda, S. et al. (1985) Nature 314:452454.) Alternatively, techniques described for the production of single chain antibodies may be adapted, using methods known in the art, to produce HYENZ-specific single chain antibodies. Antibodies with related specificity, but of distinct idiotypic composition, may be generated by chain shuffling from random combinatorial immunoglobulin libraries. (See, e.g., Burton, D. R. (1991) Proc. Natl. Acad. Sci. USA 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. USA 86:3833–3837; Winter, G. et al. (1991) Nature 349:293–299.)

Antibody fragments which contain specific binding sites for HYENZ may also be generated. For example, such fragments include, but are not limited to, F(ab')$_2$ fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HYENZ and its specific antibody. A two-site, monoclonal-based immunoassay utilizing monoclonal antibodies reactive to two non-interfering HYENZ epitopes is generally used, but a competitive binding assay may also be employed (Pound, supra).

Various methods such as Scatchard analysis in conjunction with radioimmunoassay techniques may be used to assess the affinity of antibodies for HYENZ. Affinity is expressed as an association constant, $K_a$, which is defined as the molar concentration of HYENZ-antibody complex divided by the molar concentrations of free antigen and free antibody under equilibrium conditions. The $K_a$ determined for a preparation of polyclonal antibodies, which are heterogeneous in their affinities for multiple HYENZ epitopes, represents the average affinity, or avidity, of the antibodies for HYENZ. The $K_a$ determined for a preparation of monoclonal antibodies, which are monospecific for a particular HYENZ epitope, represents a true measure of affinity. High-affinity antibody preparations with $K_a$ ranging from about $10^6$ to $10^{12}$ L/mole are preferred for use in immunoassays in which the HYENZ-antibody complex must withstand rigorous manipulations. Low-affinity antibody preparations with $K_a$ ranging from about $10^6$ to $10^7$ L/mole are preferred for use in immunopurification and similar procedures which ultimately require dissociation of HYENZ, preferably in active form, from the antibody (Catty, D. (1988) *Antibodies, Volume 1: A Practical Approach*, IRL Press, Washington D.C.; Liddell, J. E. and A. Cryer (1991) *A Practical Guide to Monoclonal Antibodies*, John Wiley & Sons, New York N.Y.).

The titer and avidity of polyclonal antibody preparations may be further evaluated to determine the quality and suitability of such preparations for certain downstream applications. For example, a polyclonal antibody preparation containing at least 1–2 mg specific antibody/ml, preferably 5–10 mg specific antibody/ml, is generally employed in procedures requiring precipitation of HYENZ-antibody complexes. Procedures for evaluating antibody specificity, titer, and avidity, and guidelines for antibody quality and usage in various applications, are generally available (See, e.g., Catty, supra, and Coligan et al., supra.)

In another embodiment of the invention, the polynucleotides encoding HYENZ, or any fragment or complement thereof, may be used for therapeutic purposes. In one aspect, modifications of gene expression can be achieved by designing complementary sequences or antisense molecules (DNA, RNA, PNA, or modified oligonucleotides) to the coding or regulatory regions of the gene encoding HYENZ. Such technology is well known in the art, and antisense oligonucleotides or larger fragments can be designed from various locations along the coding or control regions of sequences encoding HYENZ. (See, e.g., Agrawal, S., ed. (1996) *Antisense Therapeutics*, Humana Press Inc., Totawa N.J.)

In therapeutic use, any gene delivery system suitable for introduction of the antisense sequences into appropriate target cells can be used. Antisense sequences can be delivered intracellularly in the form of an expression plasmid which, upon transcription, produces a sequence complementary to at least a portion of the cellular sequence encoding the target protein. (See, e.g., Slater, J. E. et al. (1998) J. Allergy Clin. Immunol. 102(3):469475; and Scanlon, K. J. et al. (1995) 9(13):1288–1296.) Antisense sequences can also be introduced Intracellularly through the use of viral vectors, such as retrovirus and adeno-associated virus vectors. (See, e.g., Miller, A. D. (1990) Blood 76:271; Ausubel, supra; Uckert, W. and W. Walther (1994) Pharmnacol. Ther. 63(3):323–347.) Other gene delivery mechanisms include liposome-derived systems, artificial viral envelopes, and other systems known in the art. (See, e.g., Rossi, J. J. (1995) Br. Med. Bull. 51(1):217–225; Boado, R. J. et al. (1998) J. Pharm. Sci. 87(11):1308–1315; and Morris, M. C. et al. (1997) Nucleic Acids Res. 25(14):2730–2736.)

In another embodiment of the invention, polynucleotides encoding HYENZ may be used for somatic or germline gene therapy. Gene therapy may be performed to (i) correct a genetic deficiency (e.g., in the cases of severe combined immunodeficiency (SCID)-X1 disease characterized by X-linked inheritance (Cavazzana-Calvo, M. et al. (2000) Science 288:669–672), severe combined immunodeficiency syndrome associated with an inherited adenosine deaminase (ADA) deficiency (Blaese, R. M. et al. (1995) Science 270:475480; Bordignon, C. et al. (1995) Science 270:470–475), cystic fibrosis (Zabner, J. et al. (1993) Cell 75:207–216; Crystal, R. G. et al. (1995) Hum. Gene Therapy 6:643–666; Crystal, R. G. et al. (1995) Hum. Gene Therapy 6:667–703), thalassamias, familial hypercholesterolemia, and hemophilia resulting from Factor VIII or Factor IX deficiencies (Crystal, R. G. (1995) Science 270:404410; Verma, I. M. and N. Somia (1997) Nature 389:239–242)), (ii) express a conditionally lethal gene product (e.g., in the case of cancers which result from unregulated cell proliferation), or (iii) express a protein which affords protection against intracellular parasites (e.g., against human retroviruses, such as human immunodeficiency virus (HIV) (Baltimore, D. (1988) Nature 335:395–396; Poescla, E. et al. (1996) Proc. Natl. Acad. Sci. USA 93:11395–11399), hepatitis B or C virus (HBV, HCV); fungal parasites, such as *Candida albicans* and *Paracoccidioides brasiliensis*; and protozoan parasites such as *Plasmodium falciparum* and *Trynanosoma cruzi*). In the case where a genetic deficiency in HYENZ expression or regulation causes disease, the expression of HYENZ from an appropriate population of transduced cells may alleviate the clinical manifestations caused by the genetic deficiency.

In a further embodiment of the invention, diseases or disorders caused by deficiencies in HYENZ are treated by constructing mammalian expression vectors encoding HYENZ and introducing these vectors by mechanical means into HYENZ-deficient cells. Mechanical transfer technologies for use with cells in vivo or ex vitro include (i) direct DNA microinjection into individual cells, (ii) ballistic gold particle delivery, (iii) liposome-mediated transfection, (iv) receptor-mediated gene transfer, and (v) the use of DNA transposons (Morgan, R. A. and W. F. Anderson (1993) Annu. Rev. Biochem. 62:191–217; Ivics, Z. (1997) Cell 91:501–510; Boulay, J-L. and H. Récipon (1998) Curr. Opin. Biotechnol. 9:445–450).

Expression vectors that may be effective for the expression of HYENZ include, but are not limited to, the PCDDNA 3.1, EPITAG, PRCCMV2, PREP, PVAX vectors (Invitrogen, Carlsbad Calif.), PCMV-SCRIPT, PCMV-TAG, PEGSH/PERV (Stratagene, La Jolla Calif.), and PTET-OFF, PTET-ON, PTRE2, PTRE2-LUC, PTK-HYG (Clontech, Palo Alto Calif.). HYENZ may be expressed using (i) a constitutively active promoter, (e.g., from cytomegalovirus (CMV), Rous sarcoma virus (RSV), SV40 virus, thymidine kinase (TK), or β-actin genes), (ii) an inducible promoter (e.g., the tetracycline-regulated promoter (Gossen, M. and H. Bujard (1992) Proc. Natl. Acad. Sci. USA 89:5547–5551; Gossen, M. et al. (1995) Science 268:1766–1769; Rossi, F. M. V. and H. M. Blau (1998) Curr. Opin. Biotechnol. 9:451–456), commercially available in the T-REX plasmid (Invitrogen)); the ecdysone-inducible promoter (available in the plasmids PVGRXR and PIND; Invitrogen); the FK506/rapamycin inducible promoter; or the RU486/mifepristone inducible promoter (Rossi, F. M. V. and H. M. Blau, supra)), or (iii) a tissue-specific promoter or the native promoter of the endogenous gene encoding HYENZ from a normal individual.

Commercially available liposome transformation kits (e.g., the PERFECT LIPID TRANSFECTION KIT, available from Invitrogen) allow one with ordinary skill in the art to deliver polynucleotides to target cells in culture and require minimal effort to optimize experimental parameters. In the alternative, transformation is performed using the calcium phosphate method (Graham, F. L. and A. J. Eb (1973) Virology 52:456467), or by electroporation (Neumann, E. et al. (1982) EMBO J. 1:841–845). The introduction of DNA to primary cells requires modification of these standardized mammalian transfection protocols.

In another embodiment of the invention, diseases or disorders caused by genetic defects with respect to HYENZ expression are treated by constructing a retrovirus vector consisting of (i) the polynucleotide encoding HYENZ under the control of an independent promoter or the retrovirus long terminal repeat (LTR) promoter, (ii) appropriate RNA packaging signals, and (iii) a Rev-responsive element (RRE) along with additional retrovirus cis-acting RNA sequences and coding sequences required for efficient vector propagation. Retrovirus vectors (e.g., PFB and PFBNEO) are commercially available (Stratagene) and are based on published data (Riviere, I. et al. (1995) Proc. Natl. Acad. Sci. USA 92:6733–6737), incorporated by reference herein. The vector is propagated in an appropriate vector producing cell line (VPCL) that expresses an envelope gene with a tropism for receptors on the target cells or a promiscuous envelope protein such as VSVg (Armentano, D. et al. (1987) J. Virol. 61:1647–1650; Bender, M. A et al. (1987) J. Virol. 61:1639–1646; Adam, M. A. and A. D. Miller (1988) J. Virol. 62:3802–3806; Dull, T. et al. (1998) J. Virol. 72:8463–8471; Zufferey, R. et al. (1998) J. Virol. 72:9873–9880). U.S. Pat. No. 5,910,434 to Rigg ("Method for obtaining retrovirus packaging cell lines producing high transducing efficiency retroviral supernatant") discloses a method for obtaining retrovirus packaging cell lines and is hereby incorporated by reference. Propagation of retrovirus vectors, transduction of a population of cells (e.g., CD4$^+$ T-cells), and the return of transduced cells to a patient are procedures well known to persons skilled in the art of gene therapy and have been well documented (Ranga, U. et al. (1997) J. Virol. 71:7020–7029; Bauer, G. et al. (1997) Blood 89:2259–2267; Bonyhadi, M. L. (1997) J. Virol. 71:47074716; Ranga, U. et al. (1998) Proc. Natl. Acad. Sci. USA 95:1201–1206; Su, L. (1997) Blood 89:2283–2290).

In the alternative, an adenovirus-based gene therapy delivery system is used to deliver polynucleotides encoding HYENZ to cells which have one or more genetic abnormalities with respect to the expression of HYENZ. The construction and packaging of adenovirus-based vectors are well known to those with ordinary skill in the art. Replication defective adenovirus vectors have proven to be versatile for importing genes encoding immunoregulatory proteins into intact islets in the pancreas (Csete, M. E. et al. (1995) Transplantation 27:263–268). Potentially useful adenoviral vectors are described in U.S. Pat. No. 5,707,618 to Armentano ("Adenovirus vectors for gene therapy"), hereby incorporated by reference. For adenoviral vectors, see also Antinozzi, P. A. et al. (1999) Annu. Rev. Nutr. 19:511–544; and Verma, I. M. and N. Somia (1997) Nature 18:389:239–242, both incorporated by reference herein.

In another alternative, a herpes-based, gene therapy delivery system is used to deliver polynucleotides encoding HYENZ to target cells which have one or more genetic abnormalities with respect to the expression of HYENZ. The use of herpes simplex virus (HSV)-based vectors may be especially valuable for introducing HYENZ to cells of the central nervous system, for which HSV has a tropism. The construction and packaging of herpes-based vectors are well known to those with ordinary skill in the art. A replication-competent herpes simplex virus (HSV) type 1-based vector has been used to deliver a reporter gene to the eyes of primates (Liu, X. et al. (1999) Exp. Eye Res. 169:385–395). The construction of a HSV-1 virus vector has also been disclosed in detail in U.S. Pat. No. 5,804,413 to DeLuca ("Herpes simplex virus strains for gene transfer") which is hereby incorporated by reference. U.S. Pat. No. 5,804,413 teaches the use of recombinant HSV d92 which consists of a genome containing at least one exogenous gene to be transferred to a cell under the control of the appropriate promoter for purposes including human gene therapy. Also taught by this patent are the construction and use of recombinant HSV strains deleted for ICP4, ICP27 and ICP22. For HSV vectors, see also Goins, W. F. et al. (1999) J. Virol. 73:519–532 and Xu, H. et al. (1994) Dev. Biol. 163:152–161, hereby incorporated by reference. The manipulation of cloned herpesvirus sequences, the generation of recombinant virus following the transfection of multiple plasmids containing different segments of the large herpesvirus genomes, the growth and propagation of herpesvirus, and the infection of cells with herpesvirus are techniques well known to those of ordinary skill in the art.

In another alternative, an alphavirus (positive, single-stranded RNA virus) vector is used to deliver polynucleotides encoding HYENZ to target cells. The biology of the prototypic alphavirus, Semliki Forest Virus (SFV), has been studied extensively and gene transfer vectors have been based on the SFV genome (Garoff, H. and K.-J. Li (1998) Curr. Opin. Biotechnol. 9:464–469). During alphavirus RNA replication, a subgenomic RNA is generated that normally encodes the viral capsid proteins. This subgenomic RNA replicates to higher levels than the full-length genomic RNA, resulting in the overproduction of capsid proteins relative to the viral proteins with enzymatic activity (e.g., protease and polymerase). Similarly, inserting the coding sequence for HYENZ into the alphavirus genome in place of the capsid-coding region results in the production of a large number of HYENZ-coding RNAs and the synthesis of high levels of HYENZ in vector transduced cells. While alphavirus infection is typically associated with cell lysis within a few days, the ability to establish a persistent infection in hamster normal kidney cells (BHK-21) with a variant of Sindbis virus (SIN) indicates that the lytic replication of alphaviruses can be altered to suit the needs of the gene therapy application (Dryga, S. A et al. (1997) Virology 228:74–83). The wide host range of alphaviruses will allow the introduction of HYENZ into a variety of cell types. The specific transduction of a subset of cells in a population may require the sorting of cells prior to transduction The methods of manipulating infectious cDNA clones of alphaviruses, performing alphavirus cDNA and RNA transfections, and performing alphavirus infections, are well known to those with ordinary skill in the art.

Oligonucleotides derived from the transcription initiation site, e.g., between about positions −10 and +10 from the start site, may also be employed to inhibit gene expression. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing, Mt. Kisco N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding HYENZ.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HYENZ. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

An additional embodiment of the invention encompasses a method for screening for a compound which is effective in altering expression of a polynucleotide encoding HYENZ. Compounds which may be effective in altering expression of a specific polynucleotide may include, but are not limited to, oligonucleotides, antisense oligonucleotides, triple helix-forming oligonucleotides, transcription factors and other polypeptide transcriptional regulators, and non-macromolecular chemical entities which are capable of interacting with specific polynucleotide sequences. Effective compounds may alter polynucleotide expression by acting as either inhibitors or promoters of polynucleotide expression. Thus, in the treatment of disorders associated with increased HYENZ expression or activity, a compound which specifically inhibits expression of the polynucleotide encoding HYENZ may be therapeutically useful, and in the treatment of disorders associated with decreased HYENZ expression or activity, a compound which specifically promotes expression of the polynucleotide encoding HYENZ may be therapeutically useful.

At least one, and up to a plurality, of test compounds may be screened for effectiveness in altering expression of a specific polynucleotide. A test compound may be obtained by any method commonly known in the art, including chemical modification of a compound known to be effective in altering polynucleotide expression; selection from an existing, commercially-available or proprietary library of naturally-occurring or non-natural chemical compounds; rational design of a compound based on chemical and/or structural properties of the target polynucleotide; and selection from a library of chemical compounds created combinatorially or randomly. A sample comprising a polynucleotide encoding HYENZ is exposed to at least one test compound thus obtained. The sample may comprise, for example, an intact or permeabilized cell, or an in vitro cell-free or reconstituted biochemical system. Alterations in the expression of a polynucleotide encoding HYENZ are assayed by any method commonly known in the art. Typically, the expression of a specific nucleotide is detected by hybridization with a probe having a nucleotide sequence complementary to the sequence of the polynucleotide encoding HYENZ. The amount of hybridization may be quantified, thus forming the basis for a comparison of the expression of the polynucleotide both with and without exposure to one or more test compounds. Detection of a change in the expression of a polynucleotide exposed to a test compound indicates that the test compound is effective in altering the expression of the polynucleotide. A screen for a compound effective in altering expression of a specific polynucleotide can be carried out, for example, using a *Schizosaccharomyces pombe* gene expression system (Atkins, D. et al. (1999) U.S. Pat. No. 5,932,435; Arndt, G. M. et al. (2000) Nucleic Acids Res. 28:E15) or a human cell line such as HeLa cell (Clarke, M. L. et al. (2000) Biochem. Biophys. Res. Commun. 268:8–13). A particular embodiment of the present invention involves screening a combinatorial library of oligonucleotides (such as deoxyribonucleotides, ribonucleotides, peptide nucleic acids, and modified oligonucleotides) for antisense activity against a specific polynucleotide sequence (Bruice, T. W. et al. (1997) U.S. Pat. No. 5,686,242; Bruice, T. W. et al. (2000) U.S. Pat. No. 6,022,691).

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K et al. (1997) Nat. Biotechnol. 15:462–466.)

Any of the therapeutic methods described above may be applied to any subject in need of such therapy, including, for example, mammals such as humans, dogs, cats, cows, horses, rabbits, and monkeys.

An additional embodiment of the invention relates to the administration of a composition which generally comprises an active ingredient formulated with a pharmaceutically acceptable excipient. Excipients may include, for example, sugars, starches, celluloses, gums, and proteins. Various formulations are commonly known and are thoroughly discussed in the latest edition of Remnington's Pharmaceutical Sciences (Maack Publishing, Easton Pa.). Such compositions may consist of HYENZ, antibodies to HYENZ, and mimetics, agonists, antagonists, or inhibitors of HYENZ.

The compositions utilized in this invention may be administered by any number of routes including, but not limited to, oral, intravenous, intramuscular, intra-arterial, intramedullary, intrathecal, intraventricular, pulmonary, transdermal, subcutaneous, intraperitoneal, intranasal, enteral, topical, sublingual, or rectal means.

Compositions for pulmonary administration may be prepared in liquid or dry powder form. These compositions are generally aerosolized immediately prior to inhalation by the patient. In the case of small molecules (e.g. traditional low molecular weight organic drugs), aerosol delivery of fast-acting formulations is well-known in the art. In the case of macromolecules (e.g. larger peptides and proteins), recent developments in the field of pulmonary delivery via the alveolar region of the lung have enabled the practical delivery of drugs such as insulin to blood circulation (see, e.g., Patton, J. S. et al., U.S. Pat. No. 5,997,848). Pulmonary delivery has the advantage of administration without needle injection, and obviates the need for potentially toxic penetration enhancers.

Compositions suitable for use in the invention include compositions wherein the active ingredients are contained in an effective amount to achieve the intended purpose. The determination of an effective dose is well within the capability of those skilled in the art.

Specialized forms of compositions may be prepared for direct intracellular delivery of macromolecules comprising HYENZ or fragments thereof. For example, liposome preparations containing a cell-impermeable macromolecule may promote cell fusion and intracellular delivery of the macromolecule Alternatively, HYENZ or a fragment thereof may be joined to a short cationic N-terminal portion from the HIV Tat-1 protein. Fusion proteins thus generated have been found to transduce into the cells of all tissues, including the brain, in a mouse model system (Schwarze, S. R. et al. (1999) Science 285:1569–1572).

For any compound, the therapeutically effective dose can be estimated initially either in cell culture assays, e.g., of neoplastic cells, or in animal models such as mice, rats, rabbits, dogs, monkeys, or pigs. An animal model may also be used to determine the appropriate concentration range and route of administration. Such information can then be used to determine useful doses and routes for administration in humans.

A therapeutically effective dose refers to that amount of active ingredient, for example HYENZ or fragments thereof, antibodies of HYENZ, and agonists, antagonists or inhibitors of HYENZ, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of toxic to therapeutic effects is the therapeutic index, which can be expressed as the $LD_{50}/ED_{50}$ ratio. Compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in tight of factors related to the subject requiring treatment. Dosage and administration are adjusted to provide sufficient levels of the active moiety or to maintain the desired effect. Factors which may be taken into account include the severity of the disease state, the general health of the subject, the age, weigh and gender of the subject, time and frequency of administration, drug combination(s), reaction sensitivities, and response to therapy. Long-acting compositions may be administered every 3 to 4 days, every week, or biweekly depending on the half-life and clearance rate of the particular formulation.

Normal dosage amounts may vary from about 0.1 $\mu$g to 100,000 $\mu$g, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind HYENZ may be used for the diagnosis of disorders characterized by expression of HYENZ, or in assays to monitor patients being treated with HYENZ or agonists, antagonists, or inhibitors of HYENZ. Antibodies useful for diagnostic purposes may be prepared in the same manner as described above for therapeutics. Diagnostic assays for HYENZ include methods which utilize the antibody and a label to detect HYENZ in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring HYENZ, including ELISAs, RIAs, and FACS, are known in the art and provide a basis for diagnosing altered or abnormal levels of HYENZ expression. Normal or standard values for HYENZ expression are established by combining body fluids or cell extracts taken from normal mammalian subjects, for example, human subjects, with antibody to HYENZ under conditions suitable for complex formation. The amount of standard complex formation may be quantitated by various methods, such as photometric means. Quantities of HYENZ expressed in subject, control, and disease samples from biopsied tissues are compared with the standard values. Deviation between standard and subject values establishes the parameters for diagnosing disease.

In another embodiment of the invention, the polynucleotides encoding HYENZ may be used for diagnostic purposes. The polynucleotides which may be used include oligonucleotide sequences, complementary RNA and DNA molecules, and PNAs. The polynucleotides may be used to detect and quantify gene expression in biopsied tissues in which expression of HYENZ may be correlated with disease. The diagnostic assay may be used to determine absence, presence, and excess expression of HYENZ, and to monitor regulation of HYENZ levels during therapeutic intervention.

In one aspect, hybridization with PCR probes which are capable of detecting polynucleotide sequences, including genomic sequences, encoding HYENZ or closely related molecules may be used to identify nucleic acid sequences which encode HYENZ. The specificity of the probe, whether it is made from a highly specific region, e.g., the 5' regulatory region, or from a less specific region, e.g., a conserved motif, and the stringency of the hybridization or amplification will determine whether the probe identifies only naturally occurring sequences encoding HYENZ, allelic variants, or related sequences.

Probes may also be used for the detection of related sequences, and may have at least 50% sequence identity to any of the HYENZ encoding sequences. The hybridization probes of the subject invention may be DNA or RNA and may be derived from the sequence of SEQ ID NO: 15–28 or from genomic sequences including promoters, enhancers, and introns of the HYENZ gene.

Means for producing specific hybridization probes for DNAs encoding HYENZ include the cloning of polynucleotide sequences encoding HYENZ or HYENZ derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding HYENZ may be used for the diagnosis of disorders associated with expression of HYENZ. Examples of such disorders include, but are not limited to, a neurological disorder, such as epilepsy, ischemic cerebrovascular disease, stroke, cerebral neoplasms. Alzheimer's disease, Pick's disease, Huntington's disease, dementia. Parkinson's disease and other extrapyramidal disorders, amyotrophic lateral sclerosis and other motor neuron disorders, progressive neural muscular atrophy, retinitis pigmentosa, hereditary ataxias, multiple sclerosis and other demyelinating diseases, bacterial and viral meningitis, brain abscess, subdural empyema, epidural abscess, suppurative intracranial thrombophlebitis, myelitis and radiculitis, viral central nervous system disease; prion diseases including kuru, Creutzfeldt-Jakob disease, and Gerstmann-Straussler-Scheinker syndrome; fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorder of the central nervous system, cerebral palsy, a neuroskeletal disorder, an autonomic nervous system disorder, a cranial nerve disorder, a spinal cord disease, muscular dystrophy and other neuromuscular disorder, a peripheral nervous system disorder, dermatomyositis and polymyositis; inherited, metabolic, endocrine, and toxic myopathy; myasthenia gravis, periodic paralysis; a mental disorder including mood, anxiety, and schizophrenic disorders; seasonal affective disorder (SAD); akathesia, amnesia, catatonia, diabetic neuropathy, tardive dyskinesia, dystonias, paranoid psychoses, postherpetic neuralgia, and Tourette's disorder; an immune system disorder, such as inflammation, actinic keratosis, acquired immunodeficiency syndrome (AIDS), Addison's disease, adult respiratory distress syndrome, allergies, ankylosing spondylitis, amyloidosis, anemia, arteriosclerosis, asthma, atherosclerosis, autoimmune hemolytic anemia, autoimmune thyroiditis, bronchitis, bursitis, cholecystitis, cirrhosis, contact dermatitis, Crohn's disease, atopic dermatitis, dermatomyositis, diabetes mellitus, emphysema, erythroblastosis fetalis, erythema nodosum, atrophic gastritis, glomerulonephritis, Goodpasture's syndrome, gout, Graves' disease, Hachimoto's thyroiditis, paroxysmal nocturnal hemoglobinuria, hepatitis, hypereosinophilia, irritable bowel syndrome, episodic lymphopenia with lymphocytotoxins, mixed connective tissue disease (MCTD), multiple sclerosis, myasthenia gravis, myocardial or pericardial inflammation, myelofibrosis, osteoarthritis, osteoporosis, pancreatitis, polycythemia vera, polymyositis, psoriasis, Reiter's syndrome, rheumatoid arthritis, scleroderma, Sjögren's syndrome, systemic anaphylaxis, systemic lupus erythematosus, systemic sclerosis, primary thrombocythemia, thrombocytopenic purpura, ulcerative colitis, uveitis, Werner syndrome, complications of cancer, hemodialysis, and extracorporeal circulation, trauma, and hematopoietic cancer including lymphoma, leukemia, and myeloma; a genetic disorder, such as GM1-gangliosidosis, Niemann-Pick disease, adrenoleukodystrophy, Alport's syndrome, choroideremia, Duchenne and Becker muscular dystrophy, Down's syndrome, cystic fibrosis, chronic granulomatous disease, Gaucher's disease, Huntington's chorea, Marfan's syndrome, muscular dystrophy, myotonic dystrophy, pycnodysostosis, Refsum's syndrome, retinoblastoma, sickle cell anemia, thalassemia, Werner syndrome, von Willebrand's disease, von Hippel-Lindau syndrome, Wilms' tumor, Zellweger syndrome, peroxisomal acyl-CoA oxidase deficiency, peroxisomal thiolase deficiency, peroxisomal bifunctional protein deficiency, mitochondrial carnitine palmitoyl transferase and carnitine deficiency, mitochondrial very-long-chain acyl-CoA dehydrogenase deficiency, mitochondrial medium-chain acyl-CoA dehydrogenase deficiency, mitochondrial short-chain acyl-CoA dehydrogenase deficiency, mitochondrial electron transport flavoprotein and electron transport flavoprotein:ubiquinone oxidoreductase deficiency, mitochondrial trifunctional protein deficiency, and mitochondrial short-chain 3-hydroxyacyl-CoA dehydrogenase deficiency; and a cell proliferation disorder, such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombotythemia, and cancers including adenocarcinoma, leukemia, lymphoma, melanoma, myeloma, sarcoma, teratocarcinoma, and, in particular, a cancer of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. The polynucleotide sequences encoding HYENZ may be used in Southern or northern analysis, dot blot, or other membrane-baser technologies; in PCR technologies; in dipstick, pin, and multiformat ELISA-like assays; and in microarrays utilizing fluids or tissues from patients to detect altered HYENZ expression. Such qualitative or quantitative methods are well known in the art.

In a particular aspect, the nucleotide sequences encoding HYENZ may be useful in assays that detect the presence of associated disorders, particularly those mentioned above. The nucleotide sequences encoding HYENZ may be labeled by standard methods and added to a fluid or tissue sample from a patient under conditions suitable for the formation of hybridization complexes. After a suitable incubation period, the sample is washed and the signal is quantified and compared with a standard value. If the amount of signal in the patient sample is significantly altered in comparison to a control sample then the presence of altered levels of nucleotide sequences encoding HYENZ in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of HYENZ, a normal or standard profile for expression is established. This may be accomplished by combining body fluids or cell extracts taken from normal subjects, either animal or human, with a sequence, or a fragment thereof, encoding HYENZ, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of an abnormal amount of transcript (either under- or overexpressed) in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HYENZ may involve the use of PCR. These oligomers may be chemically synthesized, generated enzymatically, or produced in vitro. Oligomers will preferably contain a fragment of a polynucleotide encoding HYENZ, or a fragment of a polynucleotide complementary to the polynucleotide encoding HYENZ, and will be employed under optimized conditions for identification of a specific gene or condition Oligomers may also be employed under less stringent conditions for detection or quantification of closely related DNA or RNA sequences.

In a particular aspect, oligonucleotide primers derived from the polynucleotide sequences encoding HYENZ may be used to detect single nucleotide polymorphisms (SNPs). SNPs are substitutions, insertions and deletions that are a frequent cause of inherited or acquired genetic disease in humans. Methods of SNP detection include, but are not limited to, single-stranded conformation polymorphism (SSCP) and fluorescent SSCP (fSSCP) methods. In SSCP, oligonucleotide primers derived from the polynucleotide sequences encoding HYENZ are used to amplify DNA using the polymerase chain reaction (PCR). The DNA may be derived, for example, from diseased or normal tissue, biopsy samples, bodily fluids, and the like. SNPs in the DNA cause differences in the secondary and tertiary structures of PCR products in single-stranded form, and these differences are detectable using gel electrophoresis in non-denaturing gels. In fSCCP, the oligonucleotide primers are fluorescently labeled, which allows detection of the amplimers in high-throughput equipment such as DNA sequencing machines. Additionally, sequence database analysis methods, termed in silico SNP (is SNP), are capable of identifying polymorphisms by comparing the sequence of individual overlapping DNA fragments which assemble into a common consensus sequence. These computer-based methods filter out sequence variations due to laboratory preparation of DNA and sequencing errors using statistical models and automated analyses of DNA sequence chromatograms. In the alternative, SNPs may be detected and characterized by mass spectrometry using, for example, the high throughput MASSARRAY system (Sequenom, Inc., San Diego Calif.).

Methods which may also be used to quantify the expression of HYENZ include radiolabeling or biotinylating nucleotides, coamplification of a control nucleic acid, and interpolating results from standard curves. (See, e.g., Melby, P. C. et al. (1993) J. Immunol. Methods 159:235–244; Duplaa, C. et al. (1993) Anal. Biochem. 212:229–236.) The speed of quantitation of multiple samples may be accelerated by running the assay in a high-throughput format where the oligomer or polynucleotide of interest is presented in various dilutions and a spectrophotometric or colorimetric response gives rapid quantitation.

In further embodiments, oligonucleotides or longer fragments derived from any of the polynucleotide sequences described herein may be used as elements on a microarray. The microarray can be used in transcript imaging techniques which monitor the relative expression levels of large numbers of genes simultaneously as described in Seilhamer, J. J. et al., "Comparative Gene Transcript Analysis," U.S. Pat. No. 5,840,484, incorporated herein by reference. The microarray may also be used to identify genetic variants, mutations, and polymorphisms. This information may be used to determine gene function, to understand the genetic basis of a disorder, to diagnose a disorder, to monitor progression/regression of disease as a function of gene expression, and to develop and monitor the activities of therapeutic agents in the treatment of disease in particular, this information may be used to develop a pharmacogenomic profile of a patient in order to select the most appropriate and effective treatment regimen for that patient. For example, therapeutic agents which are highly effective and display the fewest side effects may be selected for a patient based on his/her pharmacogenomic profile.

In another embodiment, antibodies specific for HYENZ, or HYENZ or fragments thereof may be used as elements on a microarray. The microarray may be used to monitor or measure protein—protein interactions, drug-target interactions, and gene expression profiles, as described above A particular embodiment relates to the use of the polynucleotides of the present invention to generate a transcript image of a tissue or cell type. A transcript image represents the global pattern of gene expression by a particular tissue or cell type Global gene expression patterns are analyzed by quantifying the number of expressed genes and their relative abundance under given conditions and at a given time. (See Seilhamer et al., "Comparative Gene Transcript Analysis," U.S. Pat. No. 5,840,484, expressly incorporated by reference herein.) Thus a transcript image may be generated by hybridizing the polynucleotides of the present invention or their complements to the totality of transcripts or reverse transcripts of a particular tissue or cell type. In one embodiment, the hybridization takes place in high-throughput format, wherein the polynucleotides of the present invention or their complements comprise a subset of a plurality of elements on a microarray. The resultant transcript image would provide a profile of gene activity.

Transcript images may be generated using transcripts isolated from tissues, cell lines, biopsies, or other biological samples. The transcript image may thus reflect gene expression in vivo, as in the case of a tissue or biopsy sample, or in vitro, as in the case of a cell line.

Transcript images which profile the expression of the polynucleotides of the present invention may also be used in conjunction with in vitro model systems and preclinical evaluation of pharmaceuticals, as well as toxicological testing of industrial and naturally-occurring environmental compounds. All compounds induce characteristic gene expression patterns, frequently termed molecular fingerprints or toxicant signatures, which are indicative of mechanisms of action and toxicity (Nuwaysir, E. F. et al. (1999) Mol. Carcinog. 24:153–159; Steiner, S. and N. L. Anderson (2000) Toxicol. Lett. 112–113:467471, expressly incorporated by reference herein). If a test compound has a signature similar to that of a compound with known toxicity, it is likely to share those toxic properties. These fingerprints or signatures are most useful and refined when they contain expression information from a large number of genes and gene families. Ideally, a genome-wide measurement of expression provides the highest quality signature. Even genes whose expression is not altered by any tested compounds are important as well, as the levels of expression of these genes are used to normalize the rest of the expression data. The normalization procedure is useful for comparison of expression data after treatment with different compounds. While the assignment of gene function to elements of a toxicant signature aids in interpretation of toxicity mechanisms, knowledge of gene function is not necessary for the statistical matching of signatures which leads to prediction of toxicity. (See, for example, Press Release 00–02 from the National Institute of Environmental Health Sciences, released Feb. 29, 2000, available at http://www.niehs.nih.gov/oc/news/toxchip.htm) Therefore, it is important and desirable in toxicological screening using toxicant signatures to include all expressed gene sequences.

In one embodiment, the toxicity of a test compound is assessed by treating a biological sample containing nucleic acids with the test compound. Nucleic acids that are expressed in the treated biological sample are hybridized with one or more probes specific to the polynucleotides of the present invention, so that transcript levels corresponding to the polynucleotides of the present invention may be quantified. The transcript levels in the treated biological sample are compared with levels in an untreated biological sample. Differences in the transcript levels between the two samples are indicative of a toxic response caused by the test compound in the treated sample.

Another particular embodiment relates to the use of the polypeptide sequences of the present invention to analyze the proteome of a tissue or cell type. The term proteome refers to the global pattern of protein expression in a particular tissue or cell type. Each protein component of a proteome can be subjected individually to further analysis. Proteome expression patterns, or profiles, are analyzed by quantifying the number of expressed proteins and their relative abundance under given conditions and at a given time. A profile of a cell's proteome may thus be generated by separating and analyzing the polypeptides of a particular tissue or cell type. In one embodiment, the separation is achieved using two-dimensional gel electrophoresis, in which proteins from a sample are separated by isoelectric focusing in the first dimension, and then according to molecular weight by sodium dodecyl sulfate slab gel electrophoresis in the second dimension (Steiner and Anderson, supra). The proteins are visualized in the gel as discrete and uniquely positioned spots, typically by staining the gel with an agent such as Coomnassie Blue or silver or fluorescent stains. The optical density of each protein spot is generally proportional to the level of the protein in the sample. The optical densities of equivalently positioned protein spots from different samples, for example, from biological samples either treated or untreated with a test compound or therapeutic agent, are compared to identify any changes in protein spot density related to the treatment. The proteins in the spots are partially sequenced using, for example, standard methods employing chemical or enzymatic cleavage followed by mass spectrometry. The identity of the protein in a spot may be determined by comparing its partial sequence, preferably of at least 5 contiguous amino acid residues, to the polypeptide sequences of the present invention. In some cases, further sequence data may be obtained for definitive protein identification.

A proteomic profile may also be generated using antibodies specific for HYENZ to quantify the levels of HYENZ expression. In one embodiment, the antibodies are used as elements on a microarray, and protein expression levels are quantified by exposing the microarray to the sample and detecting the levels of protein bound to each array element (Lueking, A. et al. (1999) Anal. Biochem. 270:103–111; Mendoze, L. G. et al. (1999) Biotechniques 27:778–788). Detection may be performed by a variety of methods known in the art, for example, by reacting the proteins in the sample with a thiol- or amino-reactive fluorescent compound and detecting the amount of fluorescence bound at each array element.

Toxicant signatures at the proteome level are also useful for toxicological screening, and should be analyzed in parallel with toxicant signatures at the transcript level. There is a poor correlation between transcript and protein abundances for some proteins in some tissues (Anderson, N. L. and J. Seilhamer (1997) Electrophoresis 18:533–537), so proteome toxicant signatures may be useful in the analysis of compounds which do not significantly affect the transcript image, but which alter the proteomic profile. In addition, the analysis of transcripts in body fluids is difficult, due to rapid degradation of mRNA, so proteomic profiling may be more reliable and informative in such cases.

In another embodiment, the toxicity of a test compound is assessed by treating a biological sample containing proteins with the test compound. Proteins that are expressed in the treated biological sample are separated so that the amount of each protein can be quantified. The amount of each protein is compared to the amount of the corresponding protein in an untreated biological sample. A difference in the amount of protein between the two samples is indicative of a toxic response to the test compound in the treated sample. Individual proteins are identified by sequencing the amino acid residues of the individual proteins and comparing these partial sequences to the polypeptides of the present invention.

In another embodiment, the toxicity of a test compound is assessed by treating a biological sample containing proteins with the test compound. Proteins from the biological sample are incubated with antibodies specific to the polypeptides of the present invention. The amount of protein recognized by the antibodies is quantified. The amount of protein in the treated biological sample is compared with the amount in an untreated biological sample. A difference in the amount of protein between the two samples is indicative of a toxic response to the test compound in the treated sample.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. USA 93:10(61410619. Baldeschweiler et al. (1995) PCT application WO95/251116; Shalon, D. et al. (1995) PCT application WO95/35505; Heller, R. A. et al. (1997) Proc. Natl. Acad. Sci. USA 94:2150–2155; and Heller, M. J. et al. (1997) U.S. Pat. No. 5,605,662.) Various types of microarrays are well known and thoroughly described in *DNA Microarrays: A Practical Approach*, M. Schena, ed (1999) Oxford University Press, London, hereby expressly incorporated by reference.

In another embodiment of the invention, nucleic acid sequences encoding HYENZ may be used to generate hybridization probes useful in mapping the naturally occurring genomic sequence. Either coding or noncoding sequences may be used, and in some instances, noncoding sequences may be preferable over coding sequences. For example, conservation of a coding sequence among members of a multi-gene family may potentially cause undesired cross hybridization during chromosomal mapping. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Harrington, J. J. et al. (1997) Nat. Genet. 15:345–355; Price, C. M. (1993) Blood Rev. 7:127–134; and Trask, B. J. (1991) Trends Genet. 7:149–154.) Once mapped, the nucleic acid sequences of the invention may be used to develop genetic linkage maps, for example, which correlate the inheritance of a disease state with the inheritance of a particular chromosome region or restriction fragment length polymorphism (RFLP). (See, e.g., Lander, E. S. and D. Botstein (1986) Proc. Natl. Acad. Sci. USA 83:7353–7357.)

Fluorescent in situ hybridization (FISH) may be correlated with other physical and genetic map data (See, e.g., Heinz-Ulrich, et al. (1995) in Meyers, supra, pp. 965–968.) Examples of genetic map data can be found in various scientific journals or at the Online Mendelian Inheritance in Man (OMIM) World Wide Web site. Correlation between the location of the gene encoding HYENZ on a physical map and a specific disorder, or a predisposition to a specific disorder, may help define the region of DNA associated with that disorder and thus may further positional cloning efforts.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the exact chromosomal locus is not known. This information is valuable to investigators searching for disease genes using positional cloning or other gene discovery techniques. Once the gene or genes responsible for a disease or syndrome have been crudely localized by genetic linkage to a particular genomic region, e.g., ataxia-telangiectasia to 11q22–23, any sequences mapping to that area may represent associated or regulatory genes for further investigation. (See, e.g., Gatti, R. A. et al. (1988) Nature 336:577–580.) The nucleotide sequence of the instant invention may also be used to detect differences in the chromosomal location due to translocation, inversion, etc., among normal, carrier, or affected individuals.

In another embodiment of the invention, HYENZ, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between HYENZ and the agent being tested may be measured.

Another technique for drug screening provides for high throughput screening of compounds having suitable binding affinity to the protein of interest. (See. e.g., Geysen, et al. (1984) PCT application WO84/03564.) In this method, large numbers of different small test compounds are synthesized on a solid substrate. The test compounds are reacted with HYENZ, or fragments thereof, and washed. Bound HYENZ is then detected by methods well known in the art. Purified HYENZ can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HYENZ specifically compete with a test compound for binding HYENZ. In this manner, antibodies can be used to detect the presence of any peptide which shares one or more antigenic determinants with HYENZ.

In additional embodiments, the nucleotide sequences which encode HYENZ may be used in any molecular biology techniques that have yet to be developed, provided the new techniques rely on properties of nucleotide sequences that are currently known, including, but not limited to, such properties as the triplet genetic code and specific base pair interactions.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The disclosures of all patents, applications and publications, mentioned above and below, in particular U.S. Ser. No. 60/151,819, are hereby expressly incorporated by reference.

EXAMPLES

I. Construction of cDNA Libraries

RNA was purchased from Clontech or isolated from tissues described in Table 4. Some tissues were homogenized and lysed in guanidinium isothiocyanate, while others were homogenized and lysed in phenol or in a suitable mixture of denaturants, such as TRIZOL (Life Technologies), a monophasic solution of phenol and guanidine isothiocyanate, The resulting lysates were centrifuged over CsCl cushions or extracted with chloroform. RNA was precipitated from the lysates with either isopropanol or sodium acetate and ethanol, or by other routine methods.

Phenol extraction and precipitation of RNA were repeated as necessary to increase RNA purity. In some cases, RNA was treated with DNase. For most libraries, poly(A+) RNA was isolated using oligo d(T)-coupled paramagnetic particles (Promega), OLIGOTEX latex particles (QIAGEN, Chatsworth Calif.), or an OLIGOTEX mRNA purification kit (QIAGEN). Alternatively, RNA was isolated directly from tissue lysates using other RNA isolation kits, e.g., the POLY(A)PURE mRNA purification kit (Ambion, Austin Tex.).

In some cases, Stratagene was provided with RNA and constructed the corresponding cDNA libraries. Otherwise, cDNA was synthesized and cDNA libraries were constructed with the UNIZAP vector system (Stratagene) or SUPERSCRIPT plasmid system (Life Technologies), using the recommended procedures or similar methods known in the art. (See, e.g., Ausubel, 1997, supra, units 5.1–6.6.) Reverse transcription was initiated using oligo de) or random primers. Synthetic oligonucleotide adapters were ligated to double stranded cDNA, and the cDNA was digested with the appropriate restriction enzyme or enzymes. For most libraries, the cDNA was size-selected (300–1000 bp) using SEPHACRYL S1000, SEPHAROSE CL2B, or SEPHAROSE CL4B column chromatography (Amersham Pharmacia Biotech) or preparative agarose gel electrophoresis. cDNAs were ligated into compatible restriction enzyme sites of the polylinker of a suitable plasmid, e.g., PBLUESCRIPT plasmid (Stratagene), PSPORT1 plasmid (Life Technologies), pcDNA2.1 plasmid (Invitrogen, Carlsbad Calif.), or pINCY plasmid (Incyte Genomics, Palo Alto Calif.). Recombinant plasmids were transformed into competent E. coli cells including XL1-Blue, XL1-BlueMRF, or SOLR from Stratagene or DH5α, DH 10B, or ElectroMAX DH10B from Life Technologies.

II. Isolation of cDNA CLONES

Plasmids obtained as described in Example I were recovered from host cells by in vivo excision using the UNIZAP vector system (Stratagene) or by cell lysis. Plasmids were purified using at least one of the following: a Magic or WIZARD Minipreps DNA purification system (Promega); an AGTC Miniprep purification kit (Edge Biosystems, Gaithersburg Md.); and QIAWELL 8 Plasmid, QIAWELL 8 Plus Plasmid, QIAWELL 8 Ultra Plasmid purification systems or the R.E.A.L. PREP 96 plasmid purification kit from QIAGEN. Following precipitation, plasmids were resuspended in 0.1 ml of distilled water and stored, with or without lyophilization, at 4° C.

Alternatively, plasmid DNA was amplified from host cell lysates using direct link PCR in a high-throughput format (Rao, V. B. (1994) Anal. Biochem. 216:1–14). Host cell lysis and thermal cycling steps were carried out in a single reaction mixture. Samples were processed and stored in 384-well plates, and the concentration of amplified plasmid DNA was quantified fluorometrically using PICOGREEN dye (Molecular Probes, Eugene Oreg.) and a FLUOROSKAN II fluorescence scanner (Labsystems Oy, Helsinki, Finland).

III. Sequencing and Analysis

Incyte cDNA recovered in plasmids as described in Example II were sequenced as follows. Sequencing reactions were processed using standard methods or high-throughput instrumentation such as the ABI CATALYST 800 (PE Biosystems) thermal cycler or the PTC-200 thermal cycler (MJ Research) in conjunction with the HYDRA microdispenser (Robbins Scientific) or the MICROLAB 2200 (Hamilton) liquid transfer system. cDNA sequencing reactions were prepared using reagents provided by Amersham Pharmacia Biotech or supplied in ABI sequencing kits such as the ABI PRISM BIGDYE Terminator cycle sequencing ready reaction kit (PE Biosystems). Electrophoretic separation of cDNA sequencing reactions and detection of labeled polynucleotides were carried out using the MEGABACE 1000 DNA sequencing system (Molecular Dynamics); the ABI PRISM 373 or 377 sequencing system (PE Biosystems) in conjunction with standard ABI protocols and base calling software; or other sequence analysis systems known in the art. Reading frames within the cDNA sequences were identified using standard methods (reviewed in Ausubel, 1997, supra, unit 7.7). Some of the cDNA sequences were selected for extension using the techniques disclosed in Example VI.

The polynucleotide sequences derived from cDNA sequencing were assembled and analyzed using a combination of software programs which utilize algorithms well known to those skilled in the art. Table 5 summarizes the tools, programs, and algorithms used and provides applicable descriptions, references, and threshold parameters. The first column of Table 5 shows the tools, programs, and algorithms used, the second column provides brief descriptions thereof, the third column presents appropriate references, all of which are incorporated by reference herein in their entirety, and the fourth column presents, where applicable, the scores, probability values, and other parameters used to evaluate the strength of a match between two sequences (the higher the score, the greater the homology between two sequences). Sequences were analyzed using MACDNASIS PRO software (Hitachi Software Engineering, South San Francisco Calif.) and LASERGENE software (DNASTAR). Polynucleotide and polypeptide sequence alignments were generated using the default parameters specified by the clustal algorithm as incorporated into the MEGALIGN multisequence alignment program (DNASTAR), which also calculates the percent identity between aligned sequences.

The polynucleotide sequences were validated by removing vector, linker, and polyA sequence and by masking ambiguous bases, using algorithms and programs based on BLAST, dynamic programming, and dinucleotide nearest neighbor analysis. The sequences were then queried against a selection of public databases such as the GenBank primate, rodent, mammalian, vertebrate, and eukaryote databases, and BLOCKS, PRINTS, DOMO, PRODOM, and PFAM to acquire annotation using programs based on BLAST, FASTA, and BLIMPS. The sequences were assembled into full length polynucleotide sequences using programs based on Phred, Phrap, and Consed, and were screened for open reading frames using programs based on GeneMark, BLAST, and FASTA The full length polynucleotide sequences were translated to derive the corresponding full length amino acid sequences, and these full length sequences were subsequently analyzed by querying against databases such as the GenBank databases (described above), SwissProt, BLOCKS, PRINTS, DOMO, PRODOM, Prosite, and Hidden Markov Model (HMM)-based protein family databases such as PFAM. HMM is a probabilistic approach which analyzes consensus primary structures of gene families. (See, e.g., Eddy, S. R. (1996) Curr. Opin. Struct. Biol. 6:361–365.)

The programs described above for the assembly and analysis of full length polynucleotide and amino acid sequences were also used to identify polynucleotide sequence fragments from SEQ ID NO:15–28. Fragments from about 2010 about 4(00 nucleotides which are useful in hybridization and amplification technologies were described in The Invention section above.

IV. Analysis of Polynucleotide Expression

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; Ausubel, 1995, supra, ch. 4 and 16.)

Analogous computer techniques applying BLAST were used to search for identical or related molecules in cDNA databases such as GenBank or LIFESEQ (Incyte Genomics). This analysis is much faster than multiple membrane-based hybridizations. In addition, the sensitivity of the computer search can be modified to determine whether any particular match is categorized as exact or similar. The basis of the search is the product score, which is defined as:

$$\frac{\text{BLAST Score} \times \text{Percent Identity}}{5 \times \text{minimum}\{\text{length}(\text{Seq. 1}), \text{length}(\text{Seq. 2})\}}$$

The product score takes into account both the degree of similarity between two sequences and the length of the sequence match. The product score is a normalized value between 0 and 100, and is calculated as follows: the BLAST score is multiplied by the percent nucleotide identity and the product is divided by (5 times the length of the shorter of the two sequences). The BLAST score is calculated by assigning a score of +5 for every base that matches in a high-scoring segment pair (HSP), and −4 for every mismatch. Two sequences may share more than one HSP (separated by gaps). If there is more than one HSP, then the pair with the highest BLAST score is used to calculate the product score. The product score represents a balance between fractional overlap and quality in a BLAST alignment. For example, a product score of 100 is produced only for 100% identity over the entire length of the shorter of the two sequences being compared. A product score of 70 is produced either by 100% identity and 70% overlap at one end, or by 88% identity and 100% overlap at the other. A product score of 50 is produced either by 100% identity and 50% overlap at one end, or 79% identity and 100% overlap.

The results of northern analyses are reported as a percentage distribution of libraries in which the transcript encoding HYENZ occurred. Analysis involved the categorization of cDNA libraries by organ/tissue and disease. The organ/tissue categories included cardiovascular, dermatologic, developmental, endocrine, gastrointestinal, hematopoietic/immune, musculoskeletal, nervous, reproductive, and urologic. The disease/condition categories included cancer, inflammation, trauma, cell proliferation, neurological, and pooled. For each category, the number of libraries expressing the sequence of interest was counted and divided by the total number of libraries across all categories. Percentage values of tissue-specific and disease- or condition-specific expression are reported in Table 3.

V. Chromosomal Mapping of HYENZ Encoding Polynucleotides

The cDNA sequences which were used to assemble SEQ ID NO:15–28 were compared with sequences from the Incyte LIFESEQ database and public domain databases using BLAST and other implementations of the Smith-Waterman algorithm. Sequences from these databases that matched SEQ ID NO:15–28 were assembled into clusters of contiguous and overlapping sequences using assembly algorithms such as Phrap (Table 5). Radiation hybrid and genetic mapping data available from public resources such as the Stanford Human Genome Center (SHGC), Whitehead Institute for Genome Research (WIGR), and Généthon were used to determine if any of the clustered sequences had been previously mapped. Inclusion of a mapped sequence in a cluster resulted in the assignment of all sequences of that cluster, including its particular SEQ ID NO:, to that map location.

The genetic map location of SEQ ID NO:19 is described in The Invention as a range, or interval, of a human chromosome. The map position of an interval, in centiMorgans, is measured relative to the terminus of the chromosome's p-arm. (The centiMorgan (cM) is a unit of measurement based on recombination frequencies between chromosomal markers. On average, 1 cM is roughly equivalent to 1 megabase (Mb) of DNA in humans, although this can vary widely due to hot and cold spots of recombination.) The cM distances are based on genetic markers mapped by Généthon which provide boundaries for radiation hybrid markers whose sequences were included in each of the clusters. Human genome maps and other resources available to the public, such as the NCBI "GeneMap'99" World Wide Web site (http://www.ncbi.nlm.nih.gov/genemap/), can be employed to determine if previously identified disease genes map within or in proximity to the intervals indicated above.

VI. Extension of HYENZ Encoding Polynucleotides

The full length nucleic acid sequences of SEQ ID NO:15–28 were produced by extension of an appropriate fragment of the full length molecule using oligonucleotide primers designed from this fragment. One primer was synthesized to initiate 5' extension of the known fragment, and the other primer, to initiate 3' extension of the known fragment. The initial primers were designed using OLIGO 4.06 software (National Biosciences), or another appropriate programs to be about 22 to 30 nucleotides in length, to have a GC content of about 50% or more, and to anneal to the target sequence at temperatures of about 68° C. to about 72° C. Any stretch of nucleotides which would result in hairpin structures and primer—primer dimerizations was avoided.

Selected human cDNA libraries were used to extend the sequence. If more than one extension was necessary or desired, additional or nested sets of primers were designed.

High fidelity amplification was obtained by PCR using methods well known in the art. PCR was performed in 96-well plates using the PTC-200 thermal cycler (MJ Research, Inc.). The reaction mix contained DNA template, 200 nmol of each primer, reaction buffer containing $Mg^{2+}$, $(NH_4)_2SO_4$, and β-mercaptocthanol, Taq DNA polymerase (Amersham Pharmacia Biotech), ELONGASE enzyme (Life Technologies), and Pfu DNA polymerase (Stratagene), with the following parameters for primer pair PCI A and PCI B: Step 1: 94° C., 3 min; Step 2: 94° C., 15 sec; Step 3: 60° C., 1 min; Step 4: 68° C., 2 min; Step 5: Steps 2, 3, and 4 repeated 20 times; Step 6: 68° C., 5 min; Step 7: storage at 4° C. In the alternative, the parameters for primer pair T7 and SK+ were as follows: Step 1: 94° C., 3 min; Step 2: 94° C., 15 sec; Step 3: 57° C., 1 min. Step 4: 68° C., 2 min; Step 5: Steps 2, 3, and 4 repeated 20 times; Step 6: 68° C., 5 min; Step 7: storage at 4° C.

The concentration of DNA in each well was determined by dispensing 100 μl PICOGREEN quantitation reagent (0.25% (v/v) PICOGREEN; Molecular Probes, Eugene Oreg.) dissolved in 1×TE and 0.5 μl of undiluted PCR product into each well of an opaque fluorimeter plate (Corning Costar, Acton Mass.), allowing the DNA to bind to the reagent. The plate was scanned in a Fluoroskan II (Labsystems Oy, Helsinki, Finland) to measure the fluorescence of the sample and to quantify the concentration of DNA. A 5 µl to 10 µl aliquot of the reaction mixture was analyzed by electrophoresis on a 1% agarose mini-gel to determine which reactions were successful in extending the sequence.

The extended nucleotides were desalted and concentrated transferred to 384-well plates, digested with CviJI cholera virus endonuclease (Molecular Biology Research, Madison Wis.), and sonicated or sheared prior to religation into pUC 18 vector (Amersham Pharmacia Biotech). For shotgun sequencing, the digested nucleotides were separated on low concentration (0.6 to 0.8%) agarose gels, fragments were excised, and agar digested with Agar ACE (Promega). Extended clones were religated using T4 ligase (New England Biolabs, Beverly Mass.) into pUC 18 vector (Amersham Pharmacia Biotech), treated with Pfu DNA polymerase (Stratagene) to fill-in restriction site overhangs, and transfected into competent E. coli cells. Transformed cells were selected on antibiotic-containing media, and individual colonies were picked and cultured overnight at 37° C. in 384-well plates in LBI2× carb liquid media.

The cells were lysed, and DNA was amplified by PCR using Taq DNA polymerase (Amersham Pharmacia Biotech) and Pfu DNA polymerase (Stratagene) with the following parameters: Step 1: 94° C., 3 nin; Step 2: 94° C., 15 sec; Step 3: 60° C., 1 min; Step 4: 72° C., 2 min; Step 5: steps 2, 3, and 4 repeated 29 times; Step 6: 72° C., 5 min; Step 7: storage at 4° C. DNA was quantified by PICOGREEN reagent (Molecular Probes) as described above. Samples with low DNA recoveries were reamplified using the same conditions as described above. Samples were diluted with 20% dimethysulfoxide (1:2, v/v), and sequenced using DYENAMIC energy transfer sequencing primers and the DYENAMIC DIRECT kit (Amersham Pharmacia Biotech) or the ABI PRISM BIGDYE Terminator cycle sequencing ready reaction kit (PE Biosystems).

In like manner, the polynucleotide sequences of SEQ ID NO:15–28 are used to obtain 5' regulatory sequences using the procedure above, along with oligonucleotides designed for such extension, and an appropriate genomic library.

VII. Labeling and Use of Individual Hybridization Probes

Hybridization probes derived from SEQ ID NO:15–28 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 software (National Biosciences) and labeled by combining 50 pmol of each oligomer, 250 µCi of [γ-$^{32}$P] adenosine triphosphate (Amersham Pharmacia Biotech), and T4 polynucleotide kinase (DuPont NEN, Boston Mass.). The labeled oligonucleotides are substantially purified using a SEPHADEX G-25 superfine size exclusion dextran bead column (Amersham Pharmacia Biotech). An aliquot containing $10^7$ counts per minute of the labeled probe is used in a typical membrane-based hybridization analysis of human genomic DNA digested with one of the following endonucleases: Ase I, Bgl II, Eco RI, Pst L, Xba I, or Pvu II (DuPont NEN).

The DNA from each digest is fractionated on a 0.7% agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under conditions of up to, for example, 0.1×saline sodium citrate and 0.5% sodium dodecyl sulfate. Hybridization patterns are visualized using autoradiography or an alternative imaging means and compared.

VIII. Microarrays

The linkage or synthesis of array elements upon a microarray can be achieved utilizing photolithography, piezoelectric printing (inkjet printing, See, e.g., Baldeschweiler, supra), mechanical microspotting technologies, and derivatives thereof. The substrate in each of the aforementioned technologies should be uniform and solid with a non-porous surface (Schena (1999), supra). Suggested substrates include silicon, silica, glass slides, glass chips, and silicon wafers. Alternatively, a procedure analogous to a dot or slot blot may also be used to arrange and link elements to the surface of a substrate using thermal, UV, chemical, or mechanical bonding procedures. A typical array may be produced using available methods and machines well known to those of ordinary skill in the art and may contain any appropriate number of elements. (See, e.g., Schena, M. et al. (1995) Science 270:467–470; Shalon, D. et al. (1996) Genome Res. 6:639–645; Marshall, A and J. Hodgson (1998) Nat Biotechnol. 16:27–31.)

Full length cDNAs, Expressed Sequence Tags (ESTs), or fragments or oligomers thereof may comprise the elements of the microarray. Fragments or oligomers suitable for hybridization can be selected using software well known in the art such as LASERGENE software (DNASTAR). The array elements are hybridized with polynucleotides in a biological sample. The polynucleotides in the biological sample are conjugated to a fluorescent label or other molecular tag for ease of detection. After hybridization, nonhybridized nucleotides from the biological sample are removed, and a fluorescence scanner is used to detect hybridization at each array element. Alternatively, laser desorbtion and mass spectrometry may be used for detection of hybridization. The degree of complementarity and the relative abundance of each polynucleotide which hybridizes to an element on the microarray may be assessed. In one embodiment, microarray preparation and usage is described in detail below.

Tissue or Cell Sample Preparation

Total RNA is isolated from tissue samples using the guanidinium thiocyanate method and poly(A)$^+$ RNA is purified using the oligo-(dT) cellulose method. Each poly (A)$^+$ RNA sample is reverse transcribed using MMLV reverse-transcriptase, 0.05 pg/µl oligo-(dT) primer (21mer), 1×first strand buffer, 0.03 units/µl RNase inhibitor, 500 µM dATP, 500 µM dGTP, 500 µM dTTP, 40 µM dCTP, 40 µM dCTP-Cy3 (BDS) or dCTP-Cy5 (Amersham Pharmacia Biotech). The reverse transcription reaction is performed in a 25 ml volume containing 200 ng poly(A)$^+$ RNA with GEMBRIGHT kits (Incyte). Specific control poly(A)$^+$ RNAs are synthesized by in vitro transcription from non-coding yeast genomic DNA. After incubation at 37° C. for 2 hr, each reaction sample (one with Cy3 and another with Cy5 labeling) is treated with 2.5 ml of 0.5M sodium hydroxide and incubated for 20 minutes at 85° C. to the stop the reaction and degrade the RNA. Samples are purified using two successive CHROMA SPIN 30 gel filtration spin columns (CLONTECH Laboratories, Inc. (CLONTECH), Palo Alto Calif.) and after combining, both reaction samples are ethanol precipitated using 1 ml of glycogen (1 mg/ml), 60 ml sodium acetate, and 300 ml of 100% ethanol. The sample is then dried to completion using a SpeedVac (Savant Instruments Inc., Holbrook N.Y.) and resuspended in 14 µl 5×SSC/ 0.2% SDS.

Microarray Preparation

Sequences of the present invention are used to generate array elements. Each array element is amplified from bacterial cells containing vectors with cloned cDNA inserts. PCR amplification uses primers complementary to the vector sequences flanking the cDNA insert. Array elements are amplified in thirty cycles of PCR from an initial quantity of 1–2 ng to a final quantity greater than 5 $\mu$g. Amplified array elements are then purified using SEPHACRYL-400 (Amersham Pharmacia Biotech).

Purified array elements are immobilized on polymer-coated glass slides. Glass microscope slides (Corning) are cleaned by ultrasound in 0.1% SDS and acetone, with extensive distilled water washes between and after treatments. Glass slides are etched in 4% hydrofluoric acid (VWR Scientific Products Corporation (VWR), West Chester Pa.), washed extensively in distilled water, and coated with 0.05% aminopropyl silane (Sigma) in 95% ethanol. Coated slides are cured in a 110° C. oven.

Array elements are applied to the coated glass substrate using a procedure described in U.S. Pat. No. 5,807,522, incorporated herein by reference. 1 $\mu$l of the array element DNA, at an average concentration of 100 ng/$\mu$l, is loaded into the open capillary printing element by a high-speed robotic apparatus. The apparatus then deposits about 5 nl of array element sample per slide.

Microarrays are UV-crosslinked using a STRATALINKER UV-crosslinker (Stratagene). Microarrays are washed at room temperature once in 0.2% SDS and three times in distilled water. Non-specific binding sites are blocked by incubation of microarrays in 0.2% casein in phosphate buffered saline (PBS) (Tropix, Inc., Bedford Mass.) for 30 minutes at 60° C. followed by washes in 0.2% SDS and distilled water as before.

Hybridization

Hybridization reactions contain 9 $\mu$l of sample mixture consisting of 0.2 $\mu$g each of Cy3 and Cy5 labeled cDNA synthesis products in 5×SSC, 0.2% SDS hybridization buffer. The sample mixture is heated to 65° C. for 5 minutes and is aliquoted onto the microarray surface and covered with an 1.8 cm² coverslip. The arrays are transferred to a waterproof chamber having a cavity just slightly larger than a microscope slide. The chamber is kept at 100% humidity internally by the addition of 140 $\mu$l of 5×SSC in a corner of the chamber. The chamber containing the arrays is incubated for about 6.5 hours at 60° C. The arrays are washed for 10 min at 45° C. in a first wash buffer (1×SSC, 0.1% SDS), three times for 10 minutes each at 45° C. in a second wash buffer (0.1×SSC), and dried.

Detection

Reporter-labeled hybridization complexes are detected with a microscope equipped with an Innova 70 mixed gas 10 W laser (Coherent, Inc., Santa Clara Calif.) capable of generating spectral lines at 488 nm for excitation of Cy3 and at 632 nm for excitation of Cy5. The excitation laser light is focused on the array using a 20× microscope objective (Nikon, Inc., Melville N.Y.). The slide containing the array is placed on a computer-controlled X-Y stage on the microscope and raster-scanned past the objective. The 1.8 cm×1.8 cm array used in the present example is scanned with a resolution of 20 micrometers.

In two separate scans, a mixed gas multiline laser excites the two fluorophores sequentially. Emitted light is split, based on wavelength, into two photomultiplier tube detectors (PMT R1477, Hamamatsu Photonics Systems, Bridgewater N.J.) corresponding to the two fluorophores. Appropriate filters positioned between the array and the photomultiplier tubes are used to filter the signals. The emission maxima of the fluorophores used are 565 nm for Cy3 and 650 nm for Cy5. Each array is typically scanned twice, one scan per fluorophore using the appropriate filters at the laser source, although the apparatus is capable of recording the spectra from both fluorophores simultaneously.

The sensitivity of the scans is typically calibrated using the signal intensity generated by a cDNA control species added to the sample mixture at a known concentration. A specific location on the array contains a complementary DNA sequence, allowing the intensity of the signal at that location to be correlated with a weight ratio of hybridizing species of 1:100,000. When two samples from different sources (e.g., representing test and control cells), each labeled with a different fluorophore, are hybridized to a single array for the purpose of identifying genes that are differentially expressed, the calibration is done by labeling samples of the calibrating cDNA with the two fluorophores and adding identical amounts of each to the hybridization mixture.

The output of the photomultiplier lube is digitized using a 12-bit RTI-835H analog-to-digital (A/D) conversion board (Analog Devices, Inc., Norwood Mass.) installed in an IBM-compatible PC computer. The digitized data are displayed as an image where the signal intensity is mapped using a linear 20-color transformation to a pseudocolor scale ranging from blue (low signal) to red (high signal). The data is also analyzed quantitatively. Where two different fluorophores are excited and measured simultaneously, the data are first corrected for optical crosstalk (due to overlapping emission spectra) between the fluorophores using each fluorophore's emission spectrum.

A grid is superimposed over the fluorescence signal image such that the signal from each spot is centered in each element of the grid. The fluorescence signal within each element is then integrated to obtain a numerical value corresponding to the average intensity of the signal. The software used for signal analysis is the GEMTOOLS gene expression analysis program (Incyte).

IX. Complementary Polynucleotides

Sequences complementary to the HYENZ-encoding sequences, or any parts thereof, are used to detect, decrease, or inhibit expression of naturally occurring HYENZ. Although use of oligonucleotides comprising from about 15 to 30 base pairs is described, essentially the same procedure is used with smaller or with larger sequence fragments. Appropriate oligonucleotides are designed using OLIGO 4.06 software (National Biosciences) and the coding sequence of HYENZ. To inhibit transcription, a complementary oligonucleotide is designed from the most unique 5' sequence and used to prevent promoter binding to the coding sequence. To inhibit translation, a complementary oligonucleotide is designed to prevent ribosomal binding to the HYENZ-encoding transcript.

X. Expression of HYENZ

Expression and purification of HYENZ is achieved using bacterial or virus-based expression systems. For expression of HYENZ in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element Recombinant vectors are transformed into suitable bacterial hosts, e.g., BL21 (DE3). Antibiotic resistant bacteria express HYENZ upon induction with isopropyl beta-D-thiogalactopyranoside (IPTG). Expression of HYENZ in eukaryotic cells is achieved by infecting insect or mammalian cell lines with recombinant *Autographica californica* nuclear polyhedrosis virus (AcMNPV), commonly known as baculovirus. The nonessential polyhedrin gene of baculovirus is replaced with cDNA encoding HYENZ by either homologous recombination or bacterial-mediated transposition involving transfer plasmid intermediates. Viral infectivity is maintained and the strong polyhedrin promoter drives high levels of cDNA transcription. Recombinant baculovirus is used to infect *Soodrotera frueirieda* (Sf9) insect cells in most cases, or human hepatocytes, in some cases. Infection of the latter requires additional genetic modifications to baculovirus. (See Engelhard, E. K et al. (1994) Proc. Natl. Acad. Sci. USA 91:3224–3227; Sandig, V. et al. (1996) Hum. Gene Ther. 7:1937–1945.)

In most expression systems, HYENZ is synthesized as a fusion protein with, e.g., glutathione S-transferase (GST) or a peptide epitope tag, such as FLAG or 6-His, permitting rapid single-step, affinity-based purification of recombinant fusion protein from crude cell lysates. GST, a 26-kilodalton enzyme from *Schistosoma japonicum*, enables the purification of fusion proteins on immobilized glutathione under conditions that maintain protein activity and antigenicity (Amersham Pharmacia Biotech). Following purification, the GST moiety can be proteolytically cleaved from HYENZ at specifically engineered sites. FLAG, an 8-amino acid peptide, enables immunoaffinity purification using commercially available monoclonal and polyclonal anti-FLAG antibodies (Eastman Kodak). 6-His, a stretch of six consecutive histidine residues, enables purification on metal-chelate resins (QIAGEN). Methods for protein expression and purification are discussed in Ausubel (1995, supra, ch. 10 and 16). Purified HYENZ obtained by these methods can be used directly in the assays shown in Examples XI and XV.

XI. Demonstration of HYENZ Activity

For purposes of example, an assay measuring the F-glucosidase activity of an HYENZ molecule is described. Varying amounts of HYENZ are incubated with 1 mM 4-nitrophenyl β-glycopyranoside (a substrate) in 50 mM sodium acetate buffer, pH 5.0, for various times (typically 1–5 minutes) at 37° C. The reaction is halted by heating to 100° C. for 2 minutes. The absorbance is measured spectrophotometrically at 410 nm, and is proportional to the activity of HYENZ in the sample. (Hrmova, M. et al. (1998) J. Biol. Chef 273:11134–11143.)

XII. Functional Assays

HYENZ function is assessed by expressing the sequences encoding HYENZ at physiologically elevated levels in mammalian cell culture systems. cDNA is subcloned into a mammalian expression vector containing a strong promoter that drives high levels of cDNA expression. Vectors of choice include PCMV SPORT plasmid (Life Technologies) and pCR3.1 plasmid (Invitrogen), both of which contain the cytomegalovirus promoter. 5–10 µg of recombinant vector are transiently transfected into a human cell line, for example, an endothelial or hematopoietic cell line, using either liposome formulations or electroporation 1–2 µg of an additional plasmid containing sequences encoding a marker protein are co-transfected. Expression of a marker protein provides a means to distinguish transfected cells from nontransfected cells and is a reliable predictor of cDNA expression from the recombinant vector. Marker proteins of choice include, e.g., Green Fluorescent Protein (GFP; Clontech), CD64, or a CD64-GFP fusion protein. Flow cytometry (FCM), an automated, laser optics-based technique, is used to identify transfected cells expressing GFP or CD64-GFP and to evaluate the apoptotic state of the cells and other cellular properties. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) *Flow Cytometry*, Oxford, New York N.Y.

The influence of HYENZ on gene expression can be assessed using highly purified populations of cells transfected with sequences encoding HYENZ and either CD64 or CD64-GFP. CD64 and CD64(GFP are expressed on the surface of transferred cells and bind to conserved regions of human immunoglobulin G (IgG). Transfected cells are efficiently separated from nontransfected cells using magnetic beads coated with either human IgG or antibody against CD64 (DYNAL, Lake Success N.Y.). mRNA can be purified from the cells using methods well known by those of skill in the art. Expression of mRNA encoding HYENZ and other genes of interest can be analyzed by northern analysis or microarray techniques.

XIII. Production of HYENZ Specific Antibodies

HYENZ substantially purified using polyacrylamide gel electrophoresis (PAGE; see, e.g., Harrington, M. G. (1990) Methods Enzymol. 182:488–495), or other purification techniques, is used to immunize rabbits and to produce antibodies using standard protocols.

Alternatively, the HYENZ amino acid sequence is analyzed using LASERGENE software (DNASTAR) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel, 1995, supra, ch. 11.) Typically, oligopeptides of about 15 residues in length are synthesized using an ABI 43 IA peptide synthesizer (PE Biosystems) using FMOC chemistry and coupled to KLH (Sigma-Aldrich, St. Louis Mo.) by reaction with N-maleimidobenzoyl-N-hydroxysuccinimide ester (MBS) to increase immunogenicity. (See, e.g., Ausubel, 1995, supra.) Rabbits are immunized with the oligopeptide-KLH complex in complete Freund's adjuvant. Resulting antisera are tested for antipeptide and anti-HYENZ activity by, for example, binding the peptide or HYENZ to a substrate, blocking with 1% BSA, reacting with rabbit antisera, washing, and reacting with radio-iodinated goat anti-rabbit IgG. XIV. Purification of Naturally Occurring HYENZ Using Specific Antibodies Naturally occurring or recombinant HYENZ is substantially purified by immunoaffinity chromatography using antibodies specific for HYENZ. An immunoaffinity column is constructed by covalently coupling anti-HYENZ antibody to an activated chromatographic resin, such as CNBr-activated SEPHAROSE (Amersham Pharmacia Biotech). After the coupling, the resin is blocked and washed according to the manufacturer's instructions.

Media containing HYENZ are passed over the immunoaffinity column, and the column is washed under conditions that allow the preferential absorbance of HYENZ (e.g., high ionic strength buffers in the presence of detergent). The column is eluted under conditions that disrupt antibody/HYENZ binding (e.g., a buffer of pH 2 to pH 3, or a high concentration of a chaotrope, such as urea or thiocyanate ion), and HYENZ is collected.

XV. Identification of Molecules Which Interact with HYENZ

HYENZ, or biologically active fragments thereof, are labeled with $^{125}$I Bolton-Hunter reagent. (See, e.g., Bolton A. E. and W. M. Hunter (1973) Biochem. J. 133:529–539.) Candidate molecules previously arrayed in the wells of a multi-well plate are incubated with the labeled HYENZ, washed, and any wells with labeled HYENZ complex are assayed. Data obtained using different concentrations of HYENZ are used to calculate values for the number, affinity, and association of HYENZ with the candidate molecules.

Alternatively, molecules interacting with HYENZ are analyzed using the yeast two-hybrid system as described in Fields, S. and O. Song (1989, Nature 340:245–246), or using commercially available kits based on the two-hybrid system, such as the MATCHMAKER system (Clontech).

HYENZ may also be used in the PATHCALLING process (CuraGen Corp., New Haven Conn.) which employs the yeast two-hybrid system in a high-throughput manner to determine all interactions between the proteins encoded by two large libraries of genes (Nandabalan, K. et al. (2000) U.S. Pat. No. 6,057,101).

Various modifications and variations of the described methods and systems of the invention will be apparent to those skilled in the art without departing from the scope and spirit of the invention. Although the invention has been described in connection with certain embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

TABLE 1

| Polypeptide SEQ ID NO: | Nucleotide SEQ ID NO: | Clone ID | Library | Fragments |
|---|---|---|---|---|
| 1 | 15 | 1659002 | URETTUT01 | 1419114T1 (KIDNNOT09), 1513348F6 (PANCTUT01), 1659002H1 (URETTUT01), 2510396F6 (CONUTUT01), 5608212H1 (MONOTXS05) |
| 2 | 16 | 1881009 | LEUKNOT03 | 515242R1 (MMLRIDT01), 900867R1 (BRSTTUT03), 948697R1 (PANCNOT05), 1440708F1 (THYRNOT03), 1513974T1 (PANCTUT01), 1881009F6 and 1881009H1 (LEUKNOT03), 3664878H1 (PANCNOT16), 4647111H1 (PROSTUT20) |
| 3 | 17 | 2054065 | BEPINOT01 | 222269R1 (PANCNOT01), 274662R6 (PANCDIT03), 882151R1 (THYRNOT02), 996561H1 (KIDNTUT01), 1868521F6 (SKINBIT01), 2054065H1, 2054065T6, 2054065X23R1, AND 2054065X24R1 (BEPINOT01), 3208022H1 (PENCNOT03), 4624711H1 (FIBRTXT02) |
| 4 | 18 | 2183367 | SININOT01 | 2053428T6 (BEPINOT01), 2183367T6 (SININOT01), 2189606H1 (PROSNOT26), 2246242R6 (HIPONON02) |
| 5 | 19 | 2458536 | ENDANOT01 | 1806579T6 (SINTNOT13), 2050775F6 (LIVRFET02), 2458536H1 (ENDANOT01), 3769120H1 (BRSTNOT24), SBHA02033F1, SBHA01031F1, SBHA02361F1 |
| 6 | 20 | 2472979 | THP1NOT03 | 1344324H1 (PROSNOT11), 1959519R6 (BRSTNOT04), 2296250R6 (BRSTNOT05), 2472979F6 and 2472979H1 (THP1NOT03), 2672695F6 (KIDNNOT19), 2929079H1 (TLYMNOT04), 3337871H1 (SPLNNOT10), 3521758H1 (LUNGNON03), 3688966H1 (HEAANOT01), 4310094H1 (BRAUNOT01), 5264492H2 (CONDTUT02), 5286514H1 (LIVRTUS02) |
| 7 | 21 | 2612754 | UTRSTUT05 | 1376855F1 (LUNGNOT10), 1454080F1 (PENITUT01), 1617023F6 (BRAITUT12), 2481271F6 (SMCANOT01), 2612754H1 and 2612754X302T3 (UTRSTUT05), 3053767T6 (LNODNOT08), 3435070F6 (PENCNOT05), 4215323H1 (ADRENOT15) |
| 8 | 22 | 2616646 | GBLANOT01 | 938230H1 (CERVNOT01), 969237R6 (BRSTNOT05), 1283020F6 and 1283020T6 (COLNNOT16), 1442777F6 (THYRNOT03), 1967639R6 (BRSTNOT04), 2616646H1 (GBLANOT01), 3222187H1 (COLNNON03), 3478572F6 (OVARNOT11), SBWA04634V1, g884974 |
| 9 | 23 | 2625111 | PROSTUT12 | 1214365R6 (BRSTTUT01), 1316376H1 (BLADTUT02), 2625111H1 and 2625111T6 (PROSTUT12), SBKA00669F1 |
| 10 | 24 | 2724525 | LUNGTUT10 | 004103H1 (HMCINOT01), 798699R6 (OVARNOT03), 963092R2 (BRSTTUT03), 1890931F6 (BLADTUT07), 2724525F6 and 2724525H1 (LUNGTUT10), 2785502F6 (BRSTNOT13) |
| 11 | 25 | 2824691 | ADRETUT06 | 149275R6 and 1492752T1 (PROSNON01), 2824691F6 and 2824691H1 (ADRETUT06), 3229650H1 (COTRNOT01), 5063468F6 (ARTFTDT01), 5212888F6 (ENDMUNT01) |
| 12 | 26 | 4722794 | COLCTUT02 | 1522169F6 (BLADTUT04), 1699132F6 (BLADTUT05), 2656074H1 (THYMNOT04), 2903776F6 (DRGCNOT01), 3664053T6 (PANCNOT16), 3664085F6 (PANCNOT16), 5603737H1 (MONOTXN03), 5611754H1 (MONOTXS05) |
| 13 | 27 | 5328267 | DRGTNON04 | 5328267H1 and 5328758F6 (DRGTNON04) |
| 14 | 28 | 5382277 | COLNNOT38 | 265659H1 (HNT2AGT01), 1494983T1 (PROSNON01), 1974971T6 (PANCTUT02), 5283447F6 (TESTNON04), 5382277H1 (COLNNOT38) |

TABLE 2

| Protein SEQ ID NO: | Amino Acid Residues | Potential Phosphorylation Sites | Potential Glycosylation Sites | Signature Sequence | Homologous Sequence | Analytical Methods |
|---|---|---|---|---|---|---|
| 1 | 288 | T172 S183 T237 S276 T278 S12 T136 S215 Y196 | N95 | Microbodies C-terminal targeting signal: D286–L293 Hydrolase protein hydroxyaclglutathione glyoxalase II probable intergenic region isozyme multigene: I43–N205 | enzyme involved in lipogenesis and lipolysis (g2960101) [*Mycobacterium tuberculosis*] | BLAST - GenBank, BLAST - PRODOM, MOTIFS |
| 2 | 432 | S48 T79 S104 S109 S122 S332 S392 T400 S420 S143 T343 | N131 N330 | Signal Peptide: M1–Y19 Protein hydrolase glycosidase alpha trehalase acid precursor alpha-trehalose glucohydrolase glycoprotein: M1–L156 | ATH1 (g1061284) [*Saccharomyces cerevisiae*] | BLAST - GenBank, BLAST - PRODOM MOTIFS, SPScan |
| 3 | 737 | S297 S668 S15 S27 T52 T85 S108 T146 T177 T247 S317 S324 T374 T419 T425 S504 S505 T593 S630 T646 T657 T677 S699 T29 T231 S340 S457 S668 S701 | N175 N192 N406 | Cell attachment sequence: R248–D250 | dipeptidyl peptidase III (g4519883) [*Homo sapiens*] | BLAST - GenBank, MOTIFS |
| 4 | 108 | T2 S24 S48 | | Polypeptide deformylase: G62–M93 | | BLIMPS - PFAM, MOTIFS |
| 5 | 510 | T25 S26 S242 S276 S298 T357 T380 S172 T291 S374 S479 S495 | N122 N302 | Exonuclease: V61–G69, L187–L199, H438–M451 | | MOTIFS, BLIMPS - PFAM |
| 6 | 732 | S242 S509 S97 T188 S304 S357 S385 S386 S398 T400 S508 T671 S18 S31 T101 S317 S498 S529 S616 | N95 N474 N580 N613 N686 N717 | | serine-rich protein (g3873550) [*Schizosaccharomyces pombe*] P38IP (g5163089) [*Homo sapiens*] | BLAST - GenBank, MOTIFS |
| 7 | 343 | S299 S312 S294 S334 | N165 | Signal Peptide: M1–R35 Aminoacyl-transfer RNA synthetases class II: Y34–D53 transmembrane Domain: W263–V281 | phosphatidic acid phosphohydrolase type-2c (g2911498) [*Homo sapiens*] | BLAST - GenBank, MOTIFS, HMMER, SPScan |
| 8 | 717 | S413 S216 S236 S261 S271 S310 T361 S393 S423 T548 T590 S624 S712 S7 S125 S629 S650 S662 S698 | | Signal Peptide: M1–G29 Lipases serine active site: L482–G491 Transmembrane Domains: Y103–C123, K141–W163, N176–I198 | MDGL precursor (g217986) [*Penicillium camemberti*] | BLAST - GenBank, MOTIFS; HMMER; SPScan |
| 9 | 236 | T86 S208 T22 S40 T50 S53 T57 S128 | | Signal Peptide: M1–G43 MutT domain: V79–V94 | | BLIMPS - PRINTS, MOTIFS, SPScan |
| 10 | 386 | S2 S52 T62 S72 S114 T186 T242 T249 T279 T66 T204 S215 S226 S269 T286 T294 | N60 | Lipase serine active site: E129–I180 Epoxide hydrolase signature: L344–F366 Esterase/hydrolase epoxide: T62–V163 Hydrolase; tropinesterase; hydroxy; dehydrogenase; S74–T204 | similar to Hydrolase; cDNA EST EMBL: T00652 comes from this gene; cDNA (g4008339) | BLAST - GenBank, BLAST - PRODOM, BLAST - DOMO, BLIMPS - PRINTS, MOTIFS, ProfileScan |
| 11 | 522 | S66 T93 S181 T275 S301 S429 S479 S501 S509 S4 S31 S154 T245 Y488 | N80 N155 N273 N309 N329 N346 | Polyprotein endonuclease protease pol reverse transcriptase hydrolase RNA-directed DNA polymerase: V63–K187 Pol Polyprotein: G83–D262 | protease, reverse transcriptase, ribonuclease H, integrase (g4539021) [*Drosophila buzzatii*] | BLAST - GenBank, BLAST - PRODOM, BLAST - DOMO, MOTIFS |
| 12 | 420 | S222 S8 T26 S35 S118 S223 S383 T188 S348 | N227 | ATP/GTP-binding site (P-loop): A117–S124 Hydrolase N4 precursor: I119–F164, G244–E276 Hydrolase N4 precursor protein signal/1-asparaginase: K66–G270 | asparaginase related protein (g7800880) [*Neurospora crassa*] | BLAST - GenBank, BLAST - PRODOM, BLAST - DOMO, BLIMPS - PRODOM, MOTIFS |

TABLE 2-continued

| Protein SEQ ID NO: | Amino Acid Residues | Potential Phosphorylation Sites | Potential Glycosylation Sites | Signature Sequence | Homologous Sequence | Analytical Methods |
|---|---|---|---|---|---|---|
| 13 | 186 | S42 S167 T29 T88 Y142 | | Signal Peptide: M1–A18 Lysozyme: K19–C146 α-lactalbumin/lysozyme C signature: C95–C113 I74–C134 | precursor protein; P lysozyme (g49676) [*Mus musculus domesticus*] | BLIMPS - BLOCKS, BLIMPS - PRINTS BLAST - GenBank, BLAST - PRODOM, BLAST - DOMO, MOTIFS, SPScan, HMMER - PFAM, HMMER, ProfileScan |
| 14 | 248 | S221 S38 T139 S201 | N89 | Signal Peptide: M1–G36 Isoamyl acetate-hydrolyzing esterase, EC 3.1.-.-hydrolase: W15–W235 | isoamyl acetate hydrolytic enzyme (g2073519) [*Saccharomyces cerevisiae*] | BLAST - GenBank, BLAST - PRODOM, MOTIFS, SPScan |

TABLE 3

| SEQ ID NO: | Fragment | Tissue Expression (Fraction of Total) | Disease or Condition (Fraction of Total) | Vector |
|---|---|---|---|---|
| 15 | 1–47 852–911 | Cardiovascular (0.238) Gastrointestinal (0.238) Reproductive (0.190) | Cancer (0.548) Inflammation (0.333) Cell Proliferation (0.238) | pINCY |
| 16 | 596–655 974–1033 | Reproductive (0.216) Gastrointestinal (0.198) Hematopoietic/Immune (0.171) Cardiovascular (0.153) | Cancer (0.477) Inflammation (0.369) Cell Proliferation (0.135) | pTNCY |
| 17 | 536–595 | Reproductive (0.231) Nervous (0.179) Hematopoietic/Immune (0.167) Cardiovascular (0.154) Gastrointestinal (0.128) | Cancer (0.410) Inflammation (0.397) Cell Proliferation (0.244) | PSPORT1 |
| 18 | 110–169 | Reproductive (0.375) Dermatologic (0.125) Endocrine (0.125) Gastrointestinal (0.125) Hematopoietic/Immune (0.125) Nervous (0.125) | Inflammation (0.375) Cancer (0.250) Cell Proliferation (0.125) | pINCY |
| 19 | 433–492 940–999 | Nervous (0.233) Reproductive (0.233) Developmental (0.116) Gastrointestinal (0.116) | Cancer (0.419) Inflammation (0.279) Cell Proliferation (0.279) | PBLUESCRIPT |
| 20 | 541–600 1027–1086 | Reproductive (0.250) Hematopoietic/Immune (0.233) Gastrointestinal (0.150) Cardiovascular (0.117) Nervous (0.100) | Inflammation (0.484) Cancer (0.333) Cell Proliferation (0.200) | pINCY |
| 21 | 487–546 919–978 | Nervous (0.284) Reproductive (0.230) Gastrointestinal (0.122) | Cancer (0.500) Inflammation (0.311) Cell Proliferation (0.095) | pINCY |
| 22 | 651–710 | Reproductive (0.245) Gastrointestinal (0.170) Nervous (0.170) Hematopoietic/Immune (0.132) | Cancer (0.491) Inflammation (0.358) Cell Proliferation (0.226) | pINCY |
| 23 | 109–168 325–384 | Gastrointestinal (0.429) Reproductive (0.286) Urologic (0.143) | Cancer (0.500) Inflammation (0.286) | pINCY |
| 24 | 271–330 | Reproductive (0.312) Nervous (0.203) Gastrointestinal (0.125) | Cancer (0.562) Inflammation (0.203) Cell Proliferation (0.188) | pINCY |
| 25 | 650–709 1298–1357 | Nervous (0.364) Reproductive (0.182) Cardiovascular (0.182) | Inflammation (0.637) Cancer (0.273) Cell Proliferation (0.091) | pINCY |
| 26 | 272–331 | Reproductive (0.296) Hematopoietic/Immune (0.222) Cardiovascular (0.148) Nervous (0.111) | Cancer (0.556) Inflammation (0.333) Cell Proliferation (0.148) | pINCY |
| 27 | 489–548 | Nervous (1.000) | Inflammation (1.000) | pINCY |
| 28 | 103–162 | Reproductive (0.208) Nervous (0.195) Cardiovascular (0.169) Hematopoietic/Immune (0.156) | Cancer (0.416) Inflammation (0.351) Cell Proliferation (0.234) | pINCY |

TABLE 4

| Nucleotide SEQ ID NO: | Library | Library Description |
|---|---|---|
| 15 | URETTUT01 | The library was constructed using RNA isolated from right ureter tumor tissue of a 69-year-old Caucasian male during ureterectomy and lymph node excision. Pathology indicated invasive grade 3 transitional cell carcinoma. Patient history included benign colon neoplasm, asthma, emphysema, acute duodenal ulcer, and hyperplasia of the prostate. Family history included atherosclerotic coronary artery disease, congestive heart failure, and malignant lung neoplasm. |
| 16 | LEUKNOT03 | The library was constructed using RNA isolated from white blood cells of a 27-year-old female with blood type A+. The donor tested negative for cytomegalovirus (CMV). |
| 17 | BEPINOT01 | The library was constructed using RNA isolated from a bronchial epithelium primary cell line derived from a 54-year-old Caucasian male. |
| 18 | SININOT01 | The library was constructed using RNA isolated from ileum tissue obtained from the small intestine of a 4-year-old Caucasian female, who died from a closed head injury. Patient history included jaundice. Previous surgeries included a double hernia repair. |
| 19 | ENDANOT01 | The library was constructed using RNA isolated from aortic endothelial cell tissue from an explanted heart removed from a male during a heart transplant. |
| 20 | THP1NOT03 | The library was constructed using RNA isolated from untreated THP-1 cells. THP-1 (ATCC TIB 202) is a human promonocyte line derived from the peripheral blood of a 1-year-old Caucasian male with acute monocytic leukemia (ref: Int. J. Cancer (1980) 26:171). |
| 21 | UTRSTUT05 | The library was constructed using RNA isolated from uterine tumor tissue removed from a 41-year-old Caucasian female during a vaginal hysterectomy with dilation and curettage. Pathology indicated uterine leiomyoma. The endometrium was secretory and contained fragments of endometrial polyps. Benign endo- and ectocervical mucosa were identified in the endocervix. Patient history included a ventral hernia and a benign ovarian neoplasm. |
| 22 | GBLANOT01 | The library was constructed using RNA isolated from diseased gallbladder tissue removed from a 53-year-old Caucasian female during a cholecystectomy. Pathology indicated mild chronic cholecystitis and cholelithiasis with approximately 150 mixed gallstones. Family history included benign hypertension. |
| 23 | PROSTUT12 | The library was constructed using RNA isolated from prostate tumor tissue removed from a 65-year-old Caucasian male during a radical prostatectomy. Pathology indicated an adenocarcinoma (Gleason grade 2+2). Adenofibromatous hyperplasia was also present. The patient presented with elevated prostate specific antigen (PSA). |
| 24 | LUNGTUT10 | The library was constructed using RNA isolated from lung tumor tissue removed from the left upper lobe of a 65-year-old Caucasian female during a segmental lung resection. Pathology indicated a metastatic grade 2 myxoid liposarcoma and a metastatic grade 4 liposarcoma. Patient history included soft tissue cancer, breast cancer, and secondary lung cancer. |
| 25 | ADRETUT06 | The library was constructed using RNA isolated from adrenal tumor tissue removed from a 57-year-old Caucasian female during a unilateral right adrenalectomy. Pathology indicated pheochromocytoma, forming a nodular mass completely replacing the medulla of the adrenal gland. The surgical margins were negative for tumor. |
| 26 | COLCTUT02 | The library was constructed using RNA isolated from colon tumor tissue removed from the cecum of a 30-year-old Caucasian female during partial colectomy, open liver biopsy, incidental appendectomy, and permanent colostomy. Pathology indicated carcinoid tumor (grade 1 neuroendocrine carcinoma) arising in the terminal ileum, forming a mass in the right colon. Patient history included chronic sinus infections and endometriosis. Family history included hyperlipidemia, anxiety, upper lobe lung cancer, stomach cancer, liver cancer, and cirrhosis. |
| 27 | DRGTNON04 | The normalized dorsal root ganglion library was constructed from 5.64 million independent clones from a dorsal root ganglion library. Starting RNA was made from thoracic dorsal root ganglion tissue from a 32-year-old Caucasian male, who died from acute pulmonary edema, acute bronchopneumonia, pleural and pericardial effusion, and lymphoma. The patient presented with pyrexia, fatigue, and GI bleeding. The patient received radiation therapy. Patient history included probable cytomegalovirus infection, liver congestion and steatosis, splenomegaly, hemorrhagic cystitis, thyroid hemorrhage, respiratory failure, pneumonia, natural killer cell lymphoma of the pharynx, and Bell's palsy. The library was normalized in one round using conditions adapted from Soares et al., PNAS (1994) 91:9228 and Bonaldo et al., Genome Research 6 (1996):791, except that a significantly longer (48-hours/round) reannealing hybridizaiton was used. |
| 28 | COLNNOT38 | The library was constructed using RNA isolated from colon tissue removed from a Caucasian male fetus, who died from Patau's syndrome (trisomy 13) at 20-weeks' gestation. |

TABLE 5

| Program | Description | Reference | Parameter Threshold |
|---|---|---|---|
| ABI FACTURA | A program that removes vector sequences and masks ambiguous bases in nucleic acid sequences. | PE Biosystems, Foster City, CA. | |
| ABI/ PARACEL FDF | A Fast Data Finder useful in comparing and annotating amino acid or nucleic acid sequences. | PE Biosystems, Foster City, CA; Paracel Inc., Pasadena, CA. | Mismatch <50% |
| ABI AutoAssembler | A program that assembles nucleic acid sequences. | PE Biosystems, Foster City, CA. | |
| BLAST | A Basic Local Alignment Search Tool useful in sequence similarity search for amino acid and nucleic acid sequences. BLAST includes five functions: blastp, blastn, blastx, tblastn, and tblastx. | Altschul, S. F. et al. (1990) J. Mol. Biol. 215:403–410; Altschul, S.F. et al. (1997) Nucleic Acids Res. 25:3389–3402. | ESTs: Probability value = 1.0E–8 or less Full Length sequences: Probability value = 1.0E–10 or less |
| FASTA | A Pearson and Lipman algorithm that searches for similarity between a query sequence and a group of sequences of the same type. FASTA comprises as least five functions: fasta, tfasta, fastx, tfastx, and ssearch. | Pearson, W. R. and D. J. Lipman (1988) Proc. Natl. Acad Sci. USA 85:2444–2448; Pearson, W. R. (1990) Methods Enzymol. 183:63–98; and Smith, T. F. and M. S. Waterman (1981) Adv. Appl. Math 2:482–489. | ESTs: fasta E value = 1.06E–6 Assembled ESTs: fasta Identity = 95% or greater and Match length = 200 bases or greater; fastx E value = 1.0E–8 or less Full Length sequences: fastx score = 100 or greater |

TABLE 5-continued

| Program | Description | Reference | Parameter Threshold |
|---|---|---|---|
| BLIMPS | A BLocks IMProved Searcher that matches a sequence against those in BLOCKS, PRINTS, DOMO, PRODOM, and PFAM databases to search for gene families, sequence homology, and structural fingerprint regions. | Henikoff, S. and J. G. Henikoff (1991) Nucleic Acids Res. 19:6565–6572; Henikoff, J. G. and S. Henikoff (1996) Methods Enzymol. 266:88–105; and Attwood, T. K. et al. (1997) J. Chem. Inf. Comput. Sci. 37:417–424. | Score = 1000 or greater; Ratio of Score/Strength = 0.75 or larger; and, if applicable, Probability value = 1.0E–3 or less |
| HMMER | An algorithm for searching a query sequence against hidden Markov model (HMM)-based databases of protein family consensus sequences, such as PFAM. | Krogh, A. et al. (1994) J. Mol. Biol. 235:1501–1531; Sonnhammer, E. L. L. et al. (1988) Nucleic Acids Res. 26:320–322. | Score = 10–50 bits for PFAM hits, depending on individual protein families |
| ProfileScan | An algorithm that searches for structural and sequence motifs in protein sequences that match sequence patterns defined in Prosite. | Gribskov, M. et al. (1988) CABIOS 4:61–66; Gribskov, M. et al. (1989) Methods Enzymol. 183:146–159; Bairoch, A. et al. (1997) Nucleic Acids Res. 25:217–221. | Normalized quality score ≥ GCG-specified "HIGH" value for that particular Prosite motif. Generally, score = 1.4–2.1. |
| Phred | A base-calling algorithm that examines automated sequencer traces with high sensitivity and probability. | Ewing, B. et al. (1998) Genome Res. 8:175–185; Ewing, B. and P. Green (1998) Genome Res. 8:186–194. | |
| Phrap | A Phils Revised Assembly Program including SWAT and CrossMatch, programs based on efficient implementation of the Smith-Waterman algorithm, useful in searching sequence homology and assembling DNA sequences. | Smith, T. F. and M. S. Waterman (1981) Adv. Appl. Math. 2:482–489; Smith, T. F. and M. S. Waterman (1981) J. Mol. Biol. 147:195–197; and Green, P., University of Washington, Seattle, WA. | Score = 120 or greater; Match length = 56 or greater |
| Consed | A graphical tool for viewing and editing Phrap assemblies. | Gordon, D. et al. (1998) Genome Res. 8:195–202. | |
| SPScan | A weight matrix analysis program that scans protein sequences for the presence of secretory signal peptides. | Nielson, H. et al. (1997) Protein Engineering 10:1–6; Claveric, J. M. and S. Audic (1997) CABIOS 12:431–439. | Score = 3.5 or greater |
| Motifs | A program that searches amino acid sequences for patterns that matched those defined in Prosite. | Bairoch, A. et al. (1997) Nucleic Acids Res. 25:217–221; Wisconsin Package Program Manual, version 9, page M51–59, Genetics Computer Group, Madison, WI. | |

What is claimed is:

1. An isolated polynucleotide encoding a polypeptide selected from the group, consisting of:
   a) a polypeptide comprising the amino acid sequence of SEQ ID NO:12;
   b) a polypeptide comprising a naturally occurring amino acid sequence at least 90% identical to the amino acid sequence of SEQ ID NO:12;
   c) a biologically active fragment of a polypeptide having the amino acid sequence of SEQ ID NO:12; and
   d) an immunogenic fragment of a polyeptide having the amino acid sequence of SEQ ID NO:12, wherein the immunogenic fragment comprises at least 10 contiguous amino acids of SEQ ID NO:12.

2. An isolated polynucleotide encoding a polypeptide of claim 1 comprising the amino acid sequence of SEQ ID NO:12.

3. An isolated polynucleotide of claim 2, comprising the polynucleotide sequence of SEQ ID NO:26.

4. A recombinant polynucleotide comprising a promoter sequence operably linked to a polynucleotide of claim 1.

5. A cell transformed with a recombinant polynucleotide of claim 4.

6. A method for producing a polypeptide of claim 1, the method comprising:
   a) culturing a cell under conditions suitable for expression of the polypeptide, wherein said cell is transformed with a recombinant polynucleotide, and said recombinant polynucleotide comprises a promoter sequence operably linked to a polynucleotide encoding the polypeptide of claim 1, and
   b) recovering the polypeptide so expressed.

7. An isolated polynucleotide selected from the group consisting of:
   a) a polynucleotide comprising the polynucleotide sequence SEQ ID NO:26,
   b) a polynucleotide comprising a naturally occurring polynucleotide sequence at least 90% identical to the polynucleotide sequence SEQ ID NO:26,
   c) a polynucleotide complementary to a polynucleotide of a),
   d) a polynucleotide complementary to a polynucleotide of b), and
   e) an RNA equivalent of a)–d).

8. A method of detecting a target polynucleotide in a sample, said target polynucleotide having a sequence of a polynucleotide of claim 7, the method comprising:

a) hybridizing the sample with a probe comprising at least 20 contiguous nucleotides comprising a sequence complementary to said target polynucleotide in the sample, and which probe specifically hybridizes to said target polynucleotide, under conditions whereby a hybridization complex is formed between said probe and said target polynucleotide or fragments thereof, and b) detecting the presence or absence of said hybridization complex.

9. A method of claim 8; wherein the probe comprises at least 60 contiguous nucleotides.

10. A method of claim 8, further comprising:

c) detecting the amount of said hybridization complex, if present in the sample.

11. A method of detecting a target polynucleotide in a sample, said target polynucleotide having a sequence of a polynucleotide of claim 7, the method comprising:

a) amplifying said target polynucleotide or fragment thereof using polymerase chain reaction amplification, and b) detecting the presence or absence of said amplified target polynucleotide or fragment thereof.

12. A method of claim 11, further comprising:

c) detecting the amount of said amplified target polynucleotide or fragment thereof, if present in the sample.

13. An isolated polynucleotide comprising at least 60 contiguous nucleotides of:

a) the polynucleotide sequence of SEQ ID NO: 26;

b) a naturally occurring polynucleotide sequence at least 90% identical to the polynucleotide sequence of SEQ ID NO: 26;

c) a polynucleotide complementary to the polynucleotide of a);

d) a polynucleotide complementary to the polynucleotide of b); and e) an RNA equivalent of a)–d).

* * * * *

SEQUENCE LISTING

```
<160> NUMBER OF SEQ ID NOS: 28

<210> SEQ ID NO 1
<211> LENGTH: 288
<212> TYPE: PRT
<213> ORGANISM: Homo sapiens
<220> FEATURE:
<221> NAME/KEY: misc_feature
<223> OTHER INFORMATION: Incyte ID No: 1659002CD1

<400> SEQUENCE: 1

Met Ala Ala Val Leu Gln Arg Val Glu Arg Leu Ser Asn Arg Val
 1               5                  10                  15

Val Arg Val Leu Gly Cys Asn Pro Gly Pro Met Thr Leu Gln Gly
                20                  25                  30

Thr Asn Thr Tyr Leu Val Gly Thr Gly Pro Arg Arg Ile Leu Ile
                35                  40                  45

Asp Thr Gly Glu Pro Ala Ile Pro Glu Tyr Ile Ser Cys Leu Lys
                50                  55                  60

Gln Ala Leu Thr Glu Phe Asn Thr Ala Ile Gln Glu Ile Val Val
                65                  70                  75

Thr His Trp His Arg Asp His Ser Gly Ile Gly Asp Ile Cys
                80                  85                  90

Lys Ser Ile Asn Asn Asp Thr Thr Tyr Cys Ile Lys Lys Leu Pro
                95                  100                 105

Arg Asn Pro Gln Arg Glu Glu Ile Ile Gly Asn Gly Glu Gln Gln
                110                 115                 120

Tyr Val Tyr Leu Lys Asp Gly Asp Val Ile Lys Thr Glu Gly Ala
                125                 130                 135
```

```
Thr Leu Arg Val Leu Tyr Thr Pro Gly His Thr Asp Asp His Met
            140                 145                 150

Ala Leu Leu Glu Glu Asn Ala Ile Phe Ser Gly Asp Cys
            155                 160                 165

Ile Leu Gly Glu Gly Thr Thr Val Phe Glu Asp Leu Tyr Asp Tyr
            170                 175                 180

Met Asn Ser Leu Lys Glu Leu Lys Ile Lys Ala Asp Ile Ile
            185                 190                 195

Tyr Pro Gly His Gly Pro Val Ile His Asn Ala Glu Ala Lys Ile
            200                 205                 210

Gln Gln Tyr Ile Ser His Arg Asn Ile Arg Glu Gln Gln Ile Leu
            215                 220                 225

Thr Leu Phe Arg Glu Asn Phe Glu Lys Ser Phe Thr Val Met Glu
            230                 235                 240

Leu Val Lys Ile Ile Tyr Lys Asn Thr Pro Glu Asn Leu His Glu
            245                 250                 255

Met Ala Lys His Asn Leu Leu Leu His Leu Lys Lys Leu Glu Lys
            260                 265                 270

Glu Gly Lys Ile Phe Ser Asn Thr Asp Pro Asp Lys Lys Trp Lys
            275                 280                 285

Ala His Leu
```

<210> SEQ ID NO 2
<211> LENGTH: 432
<212> TYPE: PRT
<213> ORGANISM: Homo sapiens
<220> FEATURE:
<221> NAME/KEY: misc_feature
<223> OTHER INFORMATION: Incyte ID No: 1881009CD1

<400> SEQUENCE: 2

```
Met Phe Pro Ser Ile Leu Met Phe His Pro Glu Ala Ala Arg Ala
 1               5                  10                  15

Ile Leu Glu Tyr Arg Ile Arg Thr Leu Asp Gly Ala Leu Glu Asn
            20                  25                  30

Ala Gln Asn Leu Gly Tyr Gln Gly Ala Lys Phe Ala Trp Glu Ser
            35                  40                  45

Ala Asp Ser Gly Leu Glu Val Cys Pro Glu Asp Ile Tyr Gly Val
            50                  55                  60

Gln Glu Val His Val Asn Gly Ala Val Val Leu Ala Phe Glu Leu
            65                  70                  75

Tyr Tyr His Thr Thr Gln Asp Leu Gln Leu Phe Arg Glu Ala Gly
            80                  85                  90

Gly Trp Asp Val Val Arg Ala Val Ala Glu Phe Trp Cys Ser Arg
            95                  100                 105

Val Glu Trp Ser Pro Arg Glu Glu Lys Tyr His Leu Arg Gly Val
            110                 115                 120

Met Ser Pro Asp Glu Tyr His Ser Gly Val Asn Asn Ser Val Tyr
            125                 130                 135

Thr Asn Val Leu Val Gln Asn Ser Leu Arg Phe Ala Ala Ala Leu
            140                 145                 150

Ala Gln Asp Leu Gly Leu Pro Ile Pro Ser Gln Trp Leu Ala Val
            155                 160                 165

Ala Asp Lys Ile Lys Val Pro Phe Asp Val Glu Gln Asn Phe His
            170                 175                 180
```

-continued

```
Pro Glu Phe Asp Gly Tyr Glu Pro Gly Glu Val Val Lys Gln Ala
            185                 190                 195

Asp Val Val Leu Leu Gly Tyr Pro Val Pro Phe Ser Leu Ser Pro
            200                 205                 210

Asp Val Arg Arg Lys Asn Leu Glu Ile Tyr Glu Ala Val Thr Ser
            215                 220                 225

Pro Gln Gly Pro Ala Met Thr Trp Ser Met Phe Ala Val Gly Trp
            230                 235                 240

Met Glu Leu Lys Asp Ala Val Arg Ala Arg Gly Leu Leu Asp Arg
            245                 250                 255

Ser Phe Ala Asn Met Ala Glu Pro Phe Lys Val Trp Thr Glu Asn
            260                 265                 270

Ala Asp Gly Ser Gly Ala Val Asn Phe Leu Thr Gly Met Gly Gly
            275                 280                 285

Phe Leu Gln Ala Val Val Phe Gly Cys Thr Gly Phe Arg Val Thr
            290                 295                 300

Arg Ala Gly Val Thr Phe Asp Pro Val Cys Leu Ser Gly Ile Ser
            305                 310                 315

Arg Val Ser Val Ser Gly Ile Phe Tyr Gln Gly Asn Lys Leu Asn
            320                 325                 330

Phe Ser Phe Ser Glu Asp Ser Val Thr Val Glu Val Thr Ala Arg
            335                 340                 345

Ala Gly Pro Trp Ala Pro His Leu Glu Ala Glu Leu Trp Pro Ser
            350                 355                 360

Gln Ser Arg Leu Ser Leu Leu Pro Gly His Lys Val Ser Phe Pro
            365                 370                 375

Arg Ser Ala Gly Arg Ile Gln Met Ser Pro Pro Lys Leu Pro Gly
            380                 385                 390

Ser Ser Ser Ser Glu Phe Pro Gly Arg Thr Phe Ser Asp Val Arg
            395                 400                 405

Asp Pro Leu Gln Ser Pro Leu Trp Val Thr Leu Gly Ser Ser Ser
            410                 415                 420

Pro Thr Glu Ser Leu Thr Val Asp Pro Ala Ser Glu
            425                 430
```

<210> SEQ ID NO 3
<211> LENGTH: 737
<212> TYPE: PRT
<213> ORGANISM: Homo sapiens
<220> FEATURE:
<221> NAME/KEY: misc_feature
<223> OTHER INFORMATION: Incyte ID No: 2054065CD1

<400> SEQUENCE: 3

```
Met Ala Asp Thr Gln Tyr Ile Leu Pro Asn Asp Ile Gly Val Ser
 1               5                  10                  15

Ser Leu Asp Cys Arg Glu Ala Phe Arg Leu Leu Ser Pro Thr Glu
            20                  25                  30

Arg Leu Tyr Ala Tyr His Leu Ser Arg Ala Ala Trp Tyr Gly Gly
            35                  40                  45

Leu Ala Val Leu Leu Gln Thr Ser Pro Glu Ala Pro Tyr Ile Tyr
            50                  55                  60

Ala Leu Leu Ser Arg Leu Phe Arg Ala Gln Asp Pro Asp Gln Leu
            65                  70                  75

Arg Gln His Ala Leu Ala Glu Gly Leu Thr Glu Glu Glu Tyr Gln
```

```
                  80                  85                  90
Ala Phe Leu Val Tyr Ala Ala Gly Val Tyr Ser Asn Met Gly Asn
                  95                 100                 105
Tyr Lys Ser Phe Gly Asp Thr Lys Phe Val Pro Asn Leu Pro Lys
                 110                 115                 120
Glu Lys Leu Glu Arg Val Ile Leu Gly Ser Glu Ala Ala Gln Gln
                 125                 130                 135
His Pro Glu Glu Val Arg Gly Leu Trp Gln Thr Cys Gly Glu Leu
                 140                 145                 150
Met Phe Ser Leu Glu Pro Arg Leu Arg His Leu Gly Leu Gly Gln
                 155                 160                 165
Glu Gly Ile Thr Thr Tyr Phe Ser Gly Asn Cys Thr Met Glu Asp
                 170                 175                 180
Ala Lys Leu Ala Gln Asp Phe Leu Asp Ser Gln Asn Leu Ser Ala
                 185                 190                 195
Tyr Asn Thr Arg Leu Phe Lys Glu Val Asp Gly Glu Gly Lys Pro
                 200                 205                 210
Tyr Tyr Glu Val Arg Leu Ala Ser Val Leu Gly Ser Glu Pro Ser
                 215                 220                 225
Leu Asp Ser Glu Val Thr Ser Lys Leu Lys Ser Tyr Glu Phe Arg
                 230                 235                 240
Gly Ser Pro Phe Gln Val Thr Arg Gly Asp Tyr Ala Pro Ile Leu
                 245                 250                 255
Gln Lys Val Val Glu Gln Leu Glu Lys Ala Lys Ala Tyr Ala Ala
                 260                 265                 270
Asn Ser His Gln Gly Gln Met Leu Ala Gln Tyr Ile Glu Ser Phe
                 275                 280                 285
Thr Gln Gly Ser Ile Glu Ala His Lys Arg Gly Ser Arg Phe Trp
                 290                 295                 300
Ile Gln Asp Lys Gly Pro Ile Val Glu Ser Tyr Ile Gly Phe Ile
                 305                 310                 315
Glu Ser Tyr Arg Asp Pro Phe Gly Ser Arg Gly Glu Phe Glu Gly
                 320                 325                 330
Phe Val Ala Val Val Asn Lys Ala Met Ser Ala Lys Phe Glu Arg
                 335                 340                 345
Leu Val Ala Ser Ala Glu Gln Leu Leu Lys Glu Leu Pro Trp Pro
                 350                 355                 360
Pro Thr Phe Glu Lys Asp Lys Phe Leu Thr Pro Asp Phe Thr Ser
                 365                 370                 375
Leu Asp Val Leu Thr Phe Ala Gly Ser Gly Ile Pro Ala Gly Ile
                 380                 385                 390
Asn Ile Pro Asn Tyr Asp Asp Leu Arg Gln Thr Glu Gly Phe Lys
                 395                 400                 405
Asn Val Ser Leu Gly Asn Val Leu Ala Val Ala Tyr Ala Thr Gln
                 410                 415                 420
Arg Glu Lys Leu Thr Phe Leu Glu Glu Asp Asp Lys Asp Leu Tyr
                 425                 430                 435
Ile Leu Trp Lys Gly Pro Ser Phe Asp Val Gln Val Gly Leu His
                 440                 445                 450
Glu Leu Leu Gly His Gly Ser Gly Lys Leu Phe Val Gln Asp Glu
                 455                 460                 465
Lys Gly Ala Phe Asn Phe Asp Gln Glu Thr Val Ile Asn Pro Glu
                 470                 475                 480
```

-continued

```
Thr Gly Glu Gln Ile Gln Ser Trp Tyr Arg Ser Gly Glu Thr Trp
                485                 490                 495

Asp Ser Lys Phe Ser Thr Ile Ala Ser Ser Tyr Glu Glu Cys Arg
            500                 505                 510

Ala Glu Ser Val Gly Leu Tyr Leu Cys Leu His Pro Gln Val Leu
            515                 520                 525

Glu Ile Phe Gly Phe Glu Gly Ala Asp Ala Glu Asp Val Ile Tyr
            530                 535                 540

Val Asn Trp Leu Asn Met Val Arg Ala Gly Leu Leu Ala Leu Glu
            545                 550                 555

Phe Tyr Thr Pro Glu Ala Phe Asn Trp Arg Gln Ala His Met Gln
            560                 565                 570

Ala Arg Phe Val Ile Leu Arg Val Leu Leu Glu Ala Gly Glu Gly
            575                 580                 585

Leu Val Thr Ile Thr Pro Thr Thr Gly Ser Asp Gly Arg Pro Asp
            590                 595                 600

Ala Arg Val Arg Leu Asp Arg Ser Lys Ile Arg Ser Val Gly Lys
            605                 610                 615

Pro Ala Leu Glu Arg Phe Leu Arg Arg Leu Gln Val Leu Lys Ser
            620                 625                 630

Thr Gly Asp Val Ala Gly Gly Arg Ala Leu Tyr Glu Gly Tyr Ala
            635                 640                 645

Thr Val Thr Asp Ala Pro Pro Glu Cys Phe Leu Thr Leu Arg Asp
            650                 655                 660

Thr Val Leu Leu Arg Lys Glu Ser Arg Lys Leu Ile Val Gln Pro
            665                 670                 675

Asn Thr Arg Leu Glu Gly Ser Asp Val Gln Leu Leu Glu Tyr Glu
            680                 685                 690

Ala Ser Ala Ala Gly Leu Ile Arg Ser Phe Ser Glu Arg Phe Pro
            695                 700                 705

Glu Asp Gly Pro Glu Leu Glu Glu Ile Leu Thr Gln Leu Ala Thr
            710                 715                 720

Ala Asp Ala Arg Phe Trp Lys Gly Pro Ser Glu Ala Pro Ser Gly
            725                 730                 735

Gln Ala
```

<210> SEQ ID NO 4
<211> LENGTH: 108
<212> TYPE: PRT
<213> ORGANISM: Homo sapiens
<220> FEATURE:
<221> NAME/KEY: misc_feature
<223> OTHER INFORMATION: Incyte ID No: 2183367CD1

<400> SEQUENCE: 4

```
Met Thr Arg Arg Trp Gly Pro Ser Ser Gln Leu Gln His Gln Ser
 1               5                  10                  15

Leu Pro Pro Arg Ser His Ala Trp Ser Pro Arg Ala Gln Pro Ala
                20                  25                  30

Arg Arg Glu Gly Glu Arg Arg Arg Pro Asn Arg Pro Ala Trp
                35                  40                  45

Gly Pro Ser Arg Arg Pro Leu Pro Glu Arg Gly Leu Asp Pro
                50                  55                  60

Asn Gly Glu Gln Val Val Trp Gln Ala Ser Gly Trp Ala Ala Arg
                65                  70                  75
```

```
Ile Ile Gln His Glu Met Asp His Leu Gln Gly Cys Leu Phe Ile
             80                  85                  90

Asp Lys Met Asp Ser Arg Thr Phe Thr Asn Val Tyr Trp Met Lys
             95                 100                 105

Val Asn Asp

<210> SEQ ID NO 5
<211> LENGTH: 510
<212> TYPE: PRT
<213> ORGANISM: Homo sapiens
<220> FEATURE:
<221> NAME/KEY: misc_feature
<223> OTHER INFORMATION: Incyte ID No: 2458536CD1

<400> SEQUENCE: 5

Met Ala Ala Asp Ser Asp Gly Ala Val Ser Ala Pro Ala Ala
  1              5                  10                  15

Ser Asp Gly Gly Val Ser Lys Ser Thr Thr Ser Gly Glu Glu Leu
             20                  25                  30

Val Val Gln Val Pro Val Val Asp Val Gln Ser Asn Asn Phe Lys
             35                  40                  45

Glu Met Trp Pro Ser Leu Leu Leu Ala Ile Lys Thr Ala Asn Phe
             50                  55                  60

Val Ala Val Asp Thr Glu Leu Ser Gly Leu Gly Asp Arg Lys Ser
             65                  70                  75

Leu Leu Asn Gln Cys Ile Glu Glu Arg Tyr Lys Ala Val Cys His
             80                  85                  90

Ala Ala Arg Thr Arg Ser Ile Leu Ser Leu Gly Leu Ala Cys Phe
             95                 100                 105

Lys Arg Gln Pro Asp Lys Gly Glu His Ser Tyr Leu Ala Gln Val
            110                 115                 120

Phe Asn Leu Thr Leu Leu Cys Met Glu Glu Tyr Val Ile Glu Pro
            125                 130                 135

Lys Ser Val Gln Phe Leu Ile Gln His Gly Phe Asn Phe Asn Gln
            140                 145                 150

Gln Tyr Ala Gln Gly Ile Pro Tyr His Lys Gly Asn Asp Lys Gly
            155                 160                 165

Asp Glu Ser Gln Ser Gln Ser Val Arg Thr Leu Phe Leu Glu Leu
            170                 175                 180

Ile Arg Ala Arg Arg Pro Leu Val Leu His Asn Gly Leu Ile Asp
            185                 190                 195

Leu Val Phe Leu Tyr Gln Asn Phe Tyr Ala His Leu Pro Glu Ser
            200                 205                 210

Leu Gly Thr Phe Thr Ala Asp Leu Cys Glu Met Phe Pro Ala Gly
            215                 220                 225

Ile Tyr Asp Thr Lys Tyr Ala Ala Glu Phe His Ala Arg Phe Val
            230                 235                 240

Ala Ser Tyr Leu Glu Tyr Ala Phe Arg Lys Cys Glu Arg Glu Asn
            245                 250                 255

Gly Lys Gln Arg Ala Ala Gly Ser Pro His Leu Thr Leu Glu Phe
            260                 265                 270

Cys Asn Tyr Pro Ser Ser Met Arg Asp His Ile Asp Tyr Arg Cys
            275                 280                 285

Cys Leu Pro Pro Ala Thr His Arg Pro His Pro Thr Ser Ile Cys
            290                 295                 300
```

```
Asp Asn Phe Ser Ala Tyr Gly Trp Cys Pro Leu Gly Pro Gln Cys
            305                 310                 315

Pro Gln Ser His Asp Ile Asp Leu Ile Ile Asp Thr Asp Glu Ala
            320                 325                 330

Ala Ala Glu Asp Lys Arg Arg Arg Arg Arg Arg Glu Lys Arg
            335                 340                 345

Lys Arg Ala Leu Leu Asn Leu Pro Gly Thr Gln Thr Ser Gly Glu
            350                 355                 360

Ala Lys Asp Gly Pro Pro Lys Lys Gln Val Cys Gly Asp Ser Ile
            365                 370                 375

Lys Pro Glu Glu Thr Glu Gln Glu Val Ala Ala Asp Glu Thr Arg
            380                 385                 390

Asn Leu Pro His Ser Lys Gln Gly Asn Lys Asn Asp Leu Glu Met
            395                 400                 405

Gly Ile Lys Ala Ala Arg Pro Glu Ile Ala Asp Arg Ala Thr Ser
            410                 415                 420

Glu Val Pro Gly Ser Gln Ala Ser Pro Asn Pro Val Pro Gly Asp
            425                 430                 435

Gly Leu His Arg Ala Gly Phe Asp Ala Phe Met Thr Gly Tyr Val
            440                 445                 450

Met Ala Tyr Val Glu Val Ser Gln Gly Pro Gln Pro Cys Ser Ser
            455                 460                 465

Gly Pro Trp Leu Pro Glu Cys His Asn Lys Val Tyr Leu Ser Gly
            470                 475                 480

Lys Ala Val Pro Leu Thr Val Ala Lys Ser Gln Phe Ser Arg Ser
            485                 490                 495

Ser Lys Ala His Asn Gln Lys Met Lys Leu Thr Trp Gly Ser Ser
            500                 505                 510

<210> SEQ ID NO 6
<211> LENGTH: 732
<212> TYPE: PRT
<213> ORGANISM: Homo sapiens
<220> FEATURE:
<221> NAME/KEY: misc_feature
<223> OTHER INFORMATION: Incyte ID No: 2472979CD1

<400> SEQUENCE: 6

Met Gln Gln Ala Leu Glu Leu Ala Leu Asp Arg Ala Glu Tyr Val
 1               5                  10                  15

Ile Glu Ser Ala Arg Gln Arg Pro Pro Lys Arg Lys Tyr Leu Ser
                20                  25                  30

Ser Gly Arg Lys Ser Val Phe Gln Lys Leu Tyr Asp Leu Tyr Ile
                35                  40                  45

Glu Glu Cys Glu Lys Glu Pro Glu Val Lys Lys Leu Arg Arg Asn
                50                  55                  60

Val Asn Leu Leu Glu Lys Leu Val Met Gln Glu Thr Leu Ser Cys
                65                  70                  75

Leu Val Val Asn Leu Tyr Pro Gly Asn Glu Gly Tyr Ser Leu Met
                80                  85                  90

Leu Arg Gly Lys Asn Gly Ser Asp Ser Glu Thr Ile Arg Leu Pro
                95                  100                 105

Tyr Glu Glu Gly Glu Leu Leu Glu Tyr Leu Asp Ala Glu Glu Leu
                110                 115                 120

Pro Pro Ile Leu Val Asp Leu Leu Glu Lys Ser Gln Val Asn Ile
```

-continued

```
                125                 130                 135
Phe His Cys Gly Cys Val Ile Ala Glu Ile Arg Asp Tyr Arg Gln
            140                 145                 150
Ser Ser Asn Met Lys Ser Pro Gly Tyr Gln Ser Arg His Ile Leu
            155                 160                 165
Leu Arg Pro Thr Met Gln Thr Leu Ile Cys Asp Val His Ser Ile
            170                 175                 180
Thr Ser Asp Asn His Lys Trp Thr Gln Glu Asp Lys Leu Leu Leu
            185                 190                 195
Glu Ser Gln Leu Ile Leu Ala Thr Ala Glu Pro Leu Cys Leu Asp
            200                 205                 210
Pro Ser Ile Ala Val Thr Cys Thr Ala Asn Arg Leu Leu Tyr Asn
            215                 220                 225
Lys Gln Lys Met Asn Thr Arg Pro Met Lys Arg Cys Phe Lys Arg
            230                 235                 240
Tyr Ser Arg Ser Ser Leu Asn Arg Gln Gln Asp Leu Ser His Cys
            245                 250                 255
Pro Pro Pro Pro Gln Leu Arg Leu Leu Asp Phe Leu Gln Lys Arg
            260                 265                 270
Lys Glu Arg Lys Ala Gly Gln His Tyr Asp Leu Lys Ile Ser Lys
            275                 280                 285
Ala Gly Asn Cys Val Asp Met Trp Lys Arg Ser Pro Cys Asn Leu
            290                 295                 300
Ala Ile Pro Ser Glu Val Asp Val Glu Lys Tyr Ala Lys Val Glu
            305                 310                 315
Lys Ser Ile Lys Ser Asp Asp Ser Gln Pro Thr Val Trp Pro Ala
            320                 325                 330
His Asp Val Lys Asp Asp Tyr Val Phe Glu Cys Glu Ala Gly Thr
            335                 340                 345
Gln Tyr Gln Lys Thr Lys Leu Thr Ile Leu Gln Ser Leu Gly Asp
            350                 355                 360
Pro Leu Tyr Tyr Gly Lys Ile Gln Pro Cys Lys Ala Asp Glu Glu
            365                 370                 375
Ser Asp Ser Gln Met Ser Pro Ser His Ser Ser Thr Asp Asp His
            380                 385                 390
Ser Asn Trp Phe Ile Ile Gly Ser Lys Thr Asp Ala Glu Arg Val
            395                 400                 405
Val Asn Gln Tyr Gln Glu Leu Val Gln Asn Glu Ala Lys Cys Pro
            410                 415                 420
Val Lys Met Ser His Ser Ser Gly Ser Ala Ser Leu Ser Gln
            425                 430                 435
Val Ser Pro Gly Lys Glu Thr Asp Gln Thr Glu Thr Val Ser Val
            440                 445                 450
Gln Ser Ser Val Leu Gly Lys Gly Val Lys His Arg Pro Pro Pro
            455                 460                 465
Ile Lys Leu Pro Ser Ser Ser Gly Asn Ser Ser Gly Asn Tyr
            470                 475                 480
Phe Thr Pro Gln Gln Thr Ser Ser Phe Leu Lys Ser Pro Thr Pro
            485                 490                 495
Pro Pro Ser Ser Lys Pro Ser Ser Ile Pro Arg Lys Ser Ser Val
            500                 505                 510
Asp Leu Asn Gln Val Ser Met Leu Ser Pro Ala Ala Leu Ser Pro
            515                 520                 525
```

-continued

```
Ala Ser Ser Ser Gln Arg Thr Thr Ala Thr Gln Val Met Ala Asn
                530                 535                 540

Ser Ala Gly Leu Asn Phe Ile Asn Val Val Gly Ser Val Cys Gly
                545                 550                 555

Ala Gln Ala Leu Met Ser Gly Ser Asn Pro Met Leu Gly Cys Asn
                560                 565                 570

Thr Gly Ala Ile Thr Pro Ala Gly Ile Asn Leu Ser Gly Leu Leu
                575                 580                 585

Pro Ser Gly Gly Leu Leu Pro Asn Ala Leu Pro Ser Ala Met Gln
                590                 595                 600

Ala Ala Ser Gln Ala Gly Val Pro Phe Gly Leu Lys Asn Thr Ser
                605                 610                 615

Ser Leu Arg Pro Leu Asn Leu Leu Gln Leu Pro Gly Gly Ser Leu
                620                 625                 630

Ile Phe Asn Thr Leu Gln Gln Gln Gln Gln Leu Ser Gln Phe
                635                 640                 645

Thr Pro Gln Gln Pro Gln Gln Pro Thr Thr Cys Ser Pro Gln Gln
                650                 655                 660

Pro Gly Glu Gln Gly Ser Glu Gln Gly Ser Thr Ser Gln Glu Gln
                665                 670                 675

Ala Leu Ser Ala Gln Ala Ala Val Ile Asn Leu Thr Gly Val
                680                 685                 690

Gly Ser Phe Met Gln Ser Gln Ala Ala Ala Val Ala Ile Leu Ala
                695                 700                 705

Ala Ser Asn Gly Tyr Gly Ser Ser Ser Thr Asn Ser Ser Ala
                710                 715                 720

Thr Ser Ser Ser Ala Tyr Arg Gln Pro Val Lys Lys
                725                 730

<210> SEQ ID NO 7
<211> LENGTH: 343
<212> TYPE: PRT
<213> ORGANISM: Homo sapiens
<220> FEATURE:
<221> NAME/KEY: misc_feature
<223> OTHER INFORMATION: Incyte ID No: 2612754CD1

<400> SEQUENCE: 7

Met Ala Gly Gly Arg Pro His Leu Lys Arg Ser Phe Ser Ile Ile
 1               5                  10                  15

Pro Cys Phe Val Phe Val Glu Ser Val Leu Leu Gly Ile Val Ile
                20                  25                  30

Leu Leu Ala Tyr Arg Leu Glu Phe Thr Asp Thr Phe Pro Val His
                35                  40                  45

Thr Gln Gly Phe Phe Cys Tyr Asp Ser Thr Tyr Ala Lys Pro Tyr
                50                  55                  60

Pro Gly Pro Glu Ala Ala Ser Arg Val Pro Ala Leu Val Tyr
                65                  70                  75

Ala Leu Val Thr Ala Gly Pro Thr Leu Thr Ile Leu Leu Gly Glu
                80                  85                  90

Leu Ala Arg Pro Phe Phe Pro Ala Pro Ser Ala Val Pro Val
                95                  100                 105

Ile Gly Glu Ser Thr Ile Val Ser Gly Ala Cys Cys Arg Phe Ser
                110                 115                 120

Pro Pro Val Arg Arg Leu Val Arg Phe Leu Gly Val Tyr Ser Phe
```

```
                    125                 130                 135
Gly Leu Phe Thr Thr Thr Ile Phe Ala Asn Ala Gly Gln Val Val
                140                 145                 150

Thr Gly Asn Pro Thr Pro His Phe Leu Ser Val Cys Arg Pro Asn
                155                 160                 165

Tyr Thr Ala Leu Gly Cys Leu Pro Pro Ser Pro Asp Arg Pro Gly
                170                 175                 180

Pro Asp Arg Phe Val Thr Asp Gln Gly Ala Cys Ala Gly Ser Pro
                185                 190                 195

Ser Leu Val Ala Ala Arg Arg Ala Phe Pro Cys Lys Asp Ala
                200                 205                 210

Ala Leu Cys Ala Tyr Ala Val Thr Tyr Thr Ala Met Tyr Val Thr
                215                 220                 225

Leu Val Phe Arg Val Lys Gly Ser Arg Leu Val Lys Pro Ser Leu
                230                 235                 240

Cys Leu Ala Leu Leu Cys Pro Ala Phe Leu Val Gly Val Val Arg
                245                 250                 255

Val Ala Glu Tyr Arg Asn His Trp Ser Asp Val Leu Ala Gly Phe
                260                 265                 270

Leu Thr Gly Ala Ala Ile Ala Thr Phe Leu Val Thr Cys Val Val
                275                 280                 285

His Asn Phe Gln Ser Arg Pro Pro Ser Gly Arg Ser Val Ser Pro
                290                 295                 300

Trp Glu Asp Leu Gly Gln Ala Pro Thr Met Asp Ser Pro Leu Glu
                305                 310                 315

Lys Asn Pro Arg Ser Ala Gly Arg Ile Arg His Arg His Gly Ser
                320                 325                 330

Pro His Pro Ser Arg Arg Thr Ala Pro Ala Val Ala Thr
                335                 340

<210> SEQ ID NO 8
<211> LENGTH: 717
<212> TYPE: PRT
<213> ORGANISM: Homo sapiens
<220> FEATURE:
<221> NAME/KEY: misc_feature
<223> OTHER INFORMATION: Incyte ID No: 2616646CD1

<400> SEQUENCE: 8

Met Arg Arg Ser Pro Pro Ser Leu Arg Leu Arg Leu Ser Ala Asp
  1               5                  10                  15

Asn Leu Val Ala Ala Ser Gly Gly Cys Trp Phe Val Leu Gly Glu
                 20                  25                  30

Arg Arg Ala Gly Ser Leu Leu Ser Ala Ser Tyr Gly Thr Phe Ala
                 35                  40                  45

Met Pro Gly Met Val Leu Phe Gly Arg Arg Trp Ala Ile Ala Ser
                 50                  55                  60

Asp Asp Leu Val Phe Pro Gly Phe Phe Glu Leu Val Val Arg Val
                 65                  70                  75

Leu Trp Trp Ile Gly Ile Leu Thr Leu Tyr Leu Met His Arg Gly
                 80                  85                  90

Lys Leu Asp Cys Ala Gly Gly Ala Leu Leu Ser Ser Tyr Leu Ile
                 95                 100                 105

Val Leu Met Ile Leu Leu Ala Val Val Ile Cys Thr Val Ser Ala
                110                 115                 120
```

```
Ile Met Cys Val Ser Met Arg Gly Thr Ile Cys Asn Pro Gly Pro
            125                 130                 135

Arg Lys Ser Met Ser Lys Leu Leu Tyr Ile Arg Leu Ala Leu Phe
            140                 145                 150

Phe Pro Glu Met Val Trp Ala Ser Leu Gly Ala Ala Trp Val Ala
            155                 160                 165

Asp Gly Val Gln Cys Asp Arg Thr Val Asn Gly Ile Ile Ala
            170                 175                 180

Thr Val Val Ser Trp Ile Ile Ala Ala Thr Val Val Ser
            185                 190                 195

Ile Ile Ile Val Phe Asp Pro Leu Gly Gly Lys Met Ala Pro Tyr
            200                 205                 210

Ser Ser Ala Gly Pro Ser His Leu Asp Ser His Asp Ser Gln
            215                 220                 225

Leu Leu Asn Gly Leu Lys Thr Ala Ala Thr Ser Val Trp Glu Thr
            230                 235                 240

Arg Ile Lys Leu Leu Cys Cys Cys Ile Gly Lys Asp Asp His Thr
            245                 250                 255

Arg Val Ala Phe Ser Ser Thr Ala Glu Leu Phe Ser Thr Tyr Phe
            260                 265                 270

Ser Asp Thr Asp Leu Val Pro Ser Asp Ile Ala Ala Gly Leu Ala
            275                 280                 285

Leu Leu His Gln Gln Gln Asp Asn Ile Arg Asn Asn Gln Glu Pro
            290                 295                 300

Ala Gln Val Val Cys His Ala Pro Gly Ser Ser Gln Glu Ala Asp
            305                 310                 315

Leu Asp Ala Glu Leu Glu Asn Cys His His Tyr Met Gln Phe Ala
            320                 325                 330

Ala Ala Ala Tyr Gly Trp Pro Leu Tyr Ile Tyr Arg Asn Pro Leu
            335                 340                 345

Thr Gly Leu Cys Arg Ile Gly Gly Asp Cys Cys Arg Ser Arg Thr
            350                 355                 360

Thr Asp Tyr Asp Leu Val Gly Gly Asp Gln Leu Asn Cys His Phe
            365                 370                 375

Gly Ser Ile Leu His Thr Thr Gly Leu Gln Tyr Arg Asp Phe Ile
            380                 385                 390

His Val Ser Phe His Asp Lys Val Tyr Glu Leu Pro Phe Leu Val
            395                 400                 405

Ala Leu Asp His Arg Lys Glu Ser Val Val Ala Val Arg Gly
            410                 415                 420

Thr Met Ser Leu Gln Asp Val Leu Thr Asp Leu Ser Ala Glu Ser
            425                 430                 435

Glu Val Leu Asp Val Glu Cys Glu Val Gln Asp Arg Leu Ala His
            440                 445                 450

Lys Gly Ile Ser Gln Ala Ala Arg Tyr Val Tyr Gln Arg Leu Ile
            455                 460                 465

Asn Asp Gly Ile Leu Ser Gln Ala Phe Ser Ile Ala Pro Glu Tyr
            470                 475                 480

Arg Leu Val Ile Val Gly His Ser Leu Gly Gly Ala Ala Ala
            485                 490                 495

Leu Leu Ala Thr Met Leu Arg Ala Ala Tyr Pro Gln Val Arg Cys
            500                 505                 510

Tyr Ala Phe Ser Pro Pro Arg Gly Leu Trp Ser Lys Ala Leu Gln
```

-continued

```
                515                 520                 525
Glu Tyr Ser Gln Ser Phe Ile Val Ser Leu Val Leu Gly Lys Asp
                530                 535                 540
Val Ile Pro Arg Leu Ser Val Thr Asn Leu Glu Asp Leu Lys Arg
                545                 550                 555
Arg Ile Leu Arg Val Val Ala His Cys Asn Lys Pro Lys Tyr Lys
                560                 565                 570
Ile Leu Leu His Gly Leu Trp Tyr Glu Leu Phe Gly Gly Asn Pro
                575                 580                 585
Asn Asn Leu Pro Thr Glu Leu Asp Gly Gly Asp Gln Glu Val Leu
                590                 595                 600
Thr Gln Pro Leu Leu Gly Glu Gln Ser Leu Leu Thr Arg Trp Ser
                605                 610                 615
Pro Ala Tyr Ser Phe Ser Ser Asp Ser Pro Leu Asp Ser Ser Pro
                620                 625                 630
Lys Tyr Pro Pro Leu Tyr Pro Pro Gly Arg Ile Ile His Leu Gln
                635                 640                 645
Glu Glu Gly Ala Ser Gly Arg Phe Gly Cys Cys Ser Ala Ala His
                650                 655                 660
Tyr Ser Ala Lys Trp Ser His Glu Ala Glu Phe Ser Lys Ile Leu
                665                 670                 675
Ile Gly Pro Lys Met Leu Thr Asp His Met Pro Asp Ile Leu Met
                680                 685                 690
Arg Ala Leu Asp Ser Val Val Ser Asp Arg Ala Ala Cys Val Ser
                695                 700                 705
Cys Pro Ala Gln Gly Val Ser Ser Val Asp Val Ala
                710                 715

<210> SEQ ID NO 9
<211> LENGTH: 236
<212> TYPE: PRT
<213> ORGANISM: Homo sapiens
<220> FEATURE:
<221> NAME/KEY: misc_feature
<223> OTHER INFORMATION: Incyte ID No: 2625111CD1

<400> SEQUENCE: 9

Met Leu Pro Asp Cys Leu Ser Ala Glu Gly Glu Leu Arg Cys Arg
  1               5                  10                  15
Arg Leu Leu Ala Gly Ala Thr Ala Arg Leu Arg Ala Arg Pro Ala
                 20                  25                  30
Ser Ala Ala Val Leu Val Pro Leu Cys Ser Val Arg Gly Val Pro
                 35                  40                  45
Ala Leu Leu Tyr Thr Leu Arg Ser Ser Arg Leu Thr Gly Arg His
                 50                  55                  60
Lys Gly Asp Val Ser Phe Pro Gly Gly Lys Cys Asp Pro Ala Asp
                 65                  70                  75
Gln Asp Val Val His Thr Ala Leu Arg Glu Thr Arg Glu Glu Leu
                 80                  85                  90
Gly Leu Ala Val Pro Glu Glu His Val Trp Gly Leu Leu Arg Pro
                 95                 100                 105
Val Tyr Asp Pro Gln Lys Ala Thr Val Val Pro Val Leu Ala Gly
                110                 115                 120
Val Gly Pro Leu Asp Pro Gln Ser Leu Arg Pro Asn Ser Glu Glu
                125                 130                 135
```

```
Val Asp Glu Val Phe Ala Leu Pro Leu Ala His Leu Leu Gln Thr
            140                 145                 150

Gln Asn Gln Gly Tyr Thr His Phe Cys Arg Gly Gly His Phe Arg
            155                 160                 165

Tyr Thr Leu Pro Val Phe Leu His Gly Pro His Arg Val Trp Gly
            170                 175                 180

Leu Thr Ala Val Ile Thr Glu Phe Ala Leu Gln Leu Leu Ala Pro
            185                 190                 195

Gly Thr Tyr Gln Pro Arg Leu Ala Gly Leu Thr Cys Ser Gly Ala
            200                 205                 210

Glu Gly Leu Ala Arg Pro Lys Gln Pro Leu Ala Ser Pro Cys Gln
            215                 220                 225

Ala Ser Ser Thr Pro Gly Leu Asn Lys Gly Leu
            230                 235
```

<210> SEQ ID NO 10
<211> LENGTH: 386
<212> TYPE: PRT
<213> ORGANISM: Homo sapiens
<220> FEATURE:
<221> NAME/KEY: misc_feature
<223> OTHER INFORMATION: Incyte ID No: 2724525CD1

<400> SEQUENCE: 10

```
Met Ser Ala Leu Glu Lys Ser Met His Leu Gly Arg Leu Pro Ser
 1               5                  10                  15

Arg Pro Pro Leu Pro Gly Ser Gly Gly Ser Gln Ser Gly Ala Lys
                20                  25                  30

Met Arg Met Gly Pro Gly Arg Lys Arg Asp Phe Ser Pro Val Pro
                35                  40                  45

Trp Ser Gln Tyr Phe Glu Ser Met Glu Asp Val Glu Val Glu Asn
                50                  55                  60

Glu Thr Gly Lys Asp Thr Phe Arg Val Tyr Lys Ser Gly Ser Glu
                65                  70                  75

Gly Pro Val Leu Leu Leu His Gly Gly His Ser Ala Leu
                80                  85                  90

Ser Trp Ala Val Phe Thr Ala Ala Ile Ile Ser Arg Val Gln Cys
                95                 100                 105

Arg Ile Val Ala Leu Asp Leu Arg Ser His Gly Glu Thr Lys Val
               110                 115                 120

Lys Asn Pro Glu Asp Leu Ser Ala Glu Thr Met Ala Lys Asp Val
               125                 130                 135

Gly Asn Val Val Glu Ala Met Tyr Gly Asp Leu Pro Pro Ile
               140                 145                 150

Met Leu Ile Gly His Ser Met Gly Gly Ala Ile Ala Val His Thr
               155                 160                 165

Ala Ser Ser Asn Leu Val Pro Ser Leu Leu Gly Leu Cys Met Ile
               170                 175                 180

Asp Val Val Glu Gly Thr Ala Met Asp Ala Leu Asn Ser Met Gln
               185                 190                 195

Asn Phe Leu Arg Gly Arg Pro Lys Thr Phe Lys Ser Leu Glu Asn
               200                 205                 210

Ala Ile Glu Trp Ser Val Lys Ser Gly Gln Ile Arg Asn Leu Glu
               215                 220                 225

Ser Ala Arg Val Ser Met Val Gly Gln Val Lys Gln Cys Glu Gly
               230                 235                 240
```

-continued

Ile Thr Ser Pro Glu Gly Ser Lys Ser Ile Val Glu Gly Ile Ile
            245                 250                 255

Glu Glu Glu Glu Glu Asp Glu Glu Gly Ser Glu Ser Ile Ser Lys
            260                 265                 270

Arg Lys Lys Glu Asp Asp Met Glu Thr Lys Lys Asp His Pro Tyr
            275                 280                 285

Thr Trp Arg Ile Glu Leu Ala Lys Thr Glu Lys Tyr Trp Asp Gly
            290                 295                 300

Trp Phe Arg Gly Leu Ser Asn Leu Phe Leu Ser Cys Pro Ile Pro
            305                 310                 315

Lys Leu Leu Leu Ala Gly Val Asp Arg Leu Asp Lys Asp Leu
            320                 325                 330

Thr Ile Gly Gln Met Gln Gly Lys Phe Gln Met Gln Val Leu Pro
            335                 340                 345

Gln Cys Gly His Ala Val His Glu Asp Ala Pro Asp Lys Val Ala
            350                 355                 360

Glu Ala Val Ala Thr Phe Leu Ile Arg His Arg Phe Ala Glu Pro
            365                 370                 375

Ile Gly Gly Phe Gln Cys Val Phe Pro Gly Cys
            380                 385

<210> SEQ ID NO 11
<211> LENGTH: 522
<212> TYPE: PRT
<213> ORGANISM: Homo sapiens
<220> FEATURE:
<221> NAME/KEY: misc_feature
<223> OTHER INFORMATION: Incyte ID No: 2824691CD1

<400> SEQUENCE: 11

Met Val Arg Ser Gly Lys Asn Gly Asp Leu His Leu Lys Gln Ile
 1               5                  10                  15

Ala Tyr Tyr Lys Arg Thr Gly Glu Tyr His Ser Thr Thr Leu Pro
                20                  25                  30

Ser Glu Arg Ser Gly Ile Arg Arg Ala Ala Lys Lys Phe Val Phe
                35                  40                  45

Lys Glu Lys Lys Leu Phe Tyr Val Gly Lys Asp Arg Lys Gln Asn
                50                  55                  60

Arg Leu Val Ile Val Ser Glu Glu Lys Lys Val Leu Arg
65                  70                  75

Glu Cys His Glu Asn Asp Ser Gly Ala His His Gly Ile Ser Arg
                80                  85                  90

Thr Leu Thr Leu Val Glu Ser Asn Tyr Tyr Trp Thr Ser Val Thr
                95                  100                 105

Asn Asp Val Lys Gln Trp Val Tyr Ala Cys Gln His Cys Gln Val
                110                 115                 120

Ala Lys Asn Thr Val Ile Val Ala Pro Lys Gln His Leu Leu Lys
                125                 130                 135

Val Glu Asn Pro Trp Ser Leu Val Thr Val Asp Leu Met Gly Pro
                140                 145                 150

Phe His Thr Ser Asn Arg Ser His Val Tyr Ala Ile Ile Met Thr
                155                 160                 165

Asp Leu Phe Thr Lys Trp Ile Val Ile Leu Pro Leu Cys Asp Val
                170                 175                 180

Ser Ala Ser Glu Val Ser Lys Ala Ile Ile Asn Ile Phe Phe Leu

```
                    185                 190                 195
Tyr Gly Pro Pro Gln Lys Ile Ile Met Asp Gln Arg Asp Glu Phe
                200                 205                 210
Ile Gln Gln Ile Asn Ile Glu Leu Tyr Arg Leu Phe Gly Ile Lys
                215                 220                 225
Gln Ile Val Ile Ser His Thr Ser Gly Thr Val Asn Pro Met Glu
                230                 235                 240
Ser Thr Pro Asn Thr Ile Lys Ala Phe Leu Ser Lys His Cys Ala
                245                 250                 255
Asp His Pro Asn Asn Trp Asp Asp His Leu Ser Ala Val Ser Phe
                260                 265                 270
Ala Phe Asn Val Thr His Leu Glu Pro Thr Lys Asn Thr Pro Tyr
                275                 280                 285
Phe Gln Met Phe Ser Arg Asn Pro Tyr Met Pro Glu Thr Ser Asp
                290                 295                 300
Ser Leu His Glu Val Asp Gly Asp Asn Thr Ser Met Phe Ala Lys
                305                 310                 315
Ile Leu Asp Ala Ile Lys Glu Ala Asp Lys Ile Met Glu Asn Lys
                320                 325                 330
Thr Thr Ser Leu Gly Gln Met Glu Asn Asn Leu Asp Glu Leu
                335                 340                 345
Asn Lys Ser Lys Ile Ile Val Lys Lys Pro Lys Gln Leu Asn
                350                 355                 360
Pro Phe His Leu Lys Val Gly His Glu Val Leu Arg Gln Arg Lys
                365                 370                 375
Asn Trp Trp Lys Asp Gly Arg Phe Gln Ser Glu Trp Val Gly Pro
                380                 385                 390
Cys Val Ile Asp Tyr Ile Thr Glu Ser Gly Cys Ala Val Leu Arg
                395                 400                 405
Asp Asn Thr Gly Val Arg Leu Lys Arg Pro Ile Lys Met Ser His
                410                 415                 420
Leu Lys Pro Tyr Ile Arg Glu Ser Ser Glu Gln Glu Ser Leu Tyr
                425                 430                 435
Leu Leu Gln Gly Ser Val Val Ala Asp His Asp Tyr Ile Gly Leu
                440                 445                 450
Pro Glu Ile Pro Ile Gly Ala Tyr Gln Ala Asn Ile Leu Val Glu
                455                 460                 465
Asp Ala Thr Ile Gly Ile Val Asp Asn Glu Leu Leu Thr Ser Ser
                470                 475                 480
Lys Asp Arg Glu Leu Leu Glu Tyr Arg Asn Thr Lys Ile Ser Pro
                485                 490                 495
Leu Ile Asp Asp His Ser Ser Leu Glu Lys Gln Thr Phe Ser Leu
                500                 505                 510
Leu Asp Ser Ser Asn Gln Val Leu Glu Tyr Leu Ser
                515                 520

<210> SEQ ID NO 12
<211> LENGTH: 420
<212> TYPE: PRT
<213> ORGANISM: Homo sapiens
<220> FEATURE:
<221> NAME/KEY: misc_feature
<223> OTHER INFORMATION: Incyte ID No: 4722794CD1

<400> SEQUENCE: 12
```

-continued

```
Met Thr Met Glu Lys Gly Met Ser Ser Gly Glu Gly Leu Pro Ser
 1               5                  10                 15

Arg Ser Ser Gln Val Ser Ala Gly Lys Ile Thr Ala Lys Glu Leu
             20                  25                  30

Glu Thr Lys Gln Ser Tyr Lys Glu Lys Arg Gly Gly Phe Val Leu
             35                  40                  45

Val His Ala Gly Ala Gly Tyr His Ser Glu Ser Lys Ala Lys Glu
             50                  55                  60

Tyr Lys His Val Cys Lys Arg Ala Cys Gln Lys Ala Ile Glu Lys
             65                  70                  75

Leu Gln Ala Gly Ala Leu Ala Thr Asp Ala Val Thr Ala Ala Leu
             80                  85                  90

Val Glu Leu Glu Asp Ser Pro Phe Thr Asn Ala Gly Met Gly Ser
             95                 100                 105

Asn Leu Asn Leu Leu Gly Glu Ile Glu Cys Asp Ala Ser Ile Met
            110                 115                 120

Asp Gly Lys Ser Leu Asn Phe Gly Ala Val Gly Ala Leu Ser Gly
            125                 130                 135

Ile Lys Asn Pro Val Ser Val Ala Asn Arg Leu Leu Cys Glu Gly
            140                 145                 150

Gln Lys Gly Lys Leu Ser Ala Gly Arg Ile Pro Pro Cys Phe Leu
            155                 160                 165

Val Gly Glu Gly Ala Tyr Arg Trp Ala Val Asp His Gly Ile Pro
            170                 175                 180

Ser Cys Pro Pro Asn Ile Met Thr Thr Arg Phe Ser Leu Ala Ala
            185                 190                 195

Phe Lys Arg Asn Lys Arg Lys Leu Glu Leu Ala Glu Arg Val Asp
            200                 205                 210

Thr Asp Phe Met Gln Leu Lys Lys Arg Gln Ser Ser Glu Lys
            215                 220                 225

Glu Asn Asp Ser Gly Thr Leu Asp Thr Val Gly Ala Val Val
            230                 235                 240

Asp His Glu Gly Asn Val Ala Ala Ala Val Ser Ser Gly Gly Leu
            245                 250                 255

Ala Leu Lys His Pro Gly Arg Val Gly Gln Ala Ala Leu Tyr Gly
            260                 265                 270

Cys Gly Cys Trp Ala Glu Asn Thr Gly Ala His Asn Pro Tyr Ser
            275                 280                 285

Thr Ala Val Ser Thr Ser Gly Cys Gly Glu His Leu Val Arg Thr
            290                 295                 300

Ile Leu Ala Arg Glu Cys Ser His Ala Leu Gln Ala Glu Asp Ala
            305                 310                 315

His Gln Ala Leu Leu Glu Thr Met Gln Asn Lys Phe Ile Ser Ser
            320                 325                 330

Pro Phe Leu Ala Ser Glu Asp Gly Val Leu Gly Gly Val Ile Val
            335                 340                 345

Leu Arg Ser Cys Arg Cys Ser Ala Glu Pro Asp Ser Ser Gln Asn
            350                 355                 360

Lys Gln Thr Leu Leu Val Glu Phe Leu Trp Ser His Thr Thr Glu
            365                 370                 375

Ser Met Cys Val Gly Tyr Met Ser Ala Gln Asp Gly Lys Ala Lys
            380                 385                 390

Thr His Ile Ser Arg Leu Pro Pro Gly Ala Val Ala Gly Gln Ser
```

```
                        395                 400                 405
Val Ala Ile Glu Gly Gly Val Cys Arg Leu Glu Ser Pro Val Asn
                410                 415                 420

<210> SEQ ID NO 13
<211> LENGTH: 186
<212> TYPE: PRT
<213> ORGANISM: Homo sapiens
<220> FEATURE:
<221> NAME/KEY: misc_feature
<223> OTHER INFORMATION: Incyte ID No: 5328267CD1

<400> SEQUENCE: 13

Met Lys Ala Leu Leu Val Leu Gly Phe Leu Leu Ser Ala Ser
  1               5                  10                  15

Val Gln Ala Lys Thr Tyr Glu Arg Cys Glu Phe Ala Arg Thr Leu
                 20                  25                  30

Lys Arg Asn Gly Met Ser Gly Tyr Tyr Gly Val Ser Leu Ala Asp
                 35                  40                  45

Trp Val Cys Leu Ala Gln His Glu Ser Asn Tyr Asn Thr Gln Ala
                 50                  55                  60

Arg Asn Tyr Asn Pro Gly Asp Gln Ser Thr Asp Tyr Gly Ile Phe
                 65                  70                  75

Gln Ile Asn Ser Arg Tyr Trp Cys Asn Asp Gly Lys Thr Pro Arg
                 80                  85                  90

Ala Lys Asn Ala Cys Gly Ile Pro Cys Ser Ala Leu Leu Gln Asp
                 95                 100                 105

Asp Ile Thr Ala Ala Ile Gln Cys Ala Lys Arg Val Val Arg Asp
                110                 115                 120

Pro Gln Gly Ile Arg Ala Trp Val Ala Trp Gln Arg His Cys Lys
                125                 130                 135

Asn Arg Asp Leu Ser Gly Tyr Ile Arg Asn Cys Gly Val Trp Thr
                140                 145                 150

Gln Cys Thr Ser Thr Gln Leu Thr Leu Ser Leu Ser His Cys Gly
                155                 160                 165

Ser Ser Tyr Gly Glu Gly Pro Thr Ser Leu Leu Ser Pro Gln Asn
                170                 175                 180

Asn Arg Ala Phe Thr Ser
                185

<210> SEQ ID NO 14
<211> LENGTH: 248
<212> TYPE: PRT
<213> ORGANISM: Homo sapiens
<220> FEATURE:
<221> NAME/KEY: misc_feature
<223> OTHER INFORMATION: Incyte ID No: 5382277CD1

<400> SEQUENCE: 14

Met Ala Leu Cys Glu Ala Ala Gly Cys Gly Ser Ala Leu Leu Trp
  1               5                  10                  15

Pro Arg Leu Leu Leu Phe Gly Asp Ser Ile Thr Gln Phe Ser Phe
                 20                  25                  30

Gln Gln Gly Gly Trp Gly Ala Ser Leu Ala Asp Arg Leu Val Arg
                 35                  40                  45

Lys Cys Asp Val Leu Asn Arg Gly Phe Ser Gly Tyr Asn Thr Arg
                 50                  55                  60

Trp Ala Lys Ile Ile Leu Pro Arg Leu Ile Arg Lys Gly Asn Ser
```

-continued

```
                65                  70                  75
Leu Asp Ile Pro Val Ala Val Thr Ile Phe Phe Gly Ala Asn Asp
                    80                  85                  90
Ser Ala Leu Lys Asp Glu Asn Pro Lys Gln His Ile Pro Leu Glu
                    95                 100                 105
Glu Tyr Ala Ala Asn Leu Lys Ser Met Val Gln Tyr Leu Lys Ser
                   110                 115                 120
Val Asp Ile Pro Glu Asn Arg Val Ile Leu Ile Thr Pro Thr Pro
                   125                 130                 135
Leu Cys Glu Thr Ala Trp Glu Glu Gln Cys Ile Ile Gln Gly Cys
                   140                 145                 150
Lys Leu Asn Arg Leu Asn Ser Val Val Gly Glu Tyr Ala Asn Ala
                   155                 160                 165
Cys Leu Gln Val Ala Gln Asp Cys Gly Thr Asp Val Leu Asp Leu
                   170                 175                 180
Trp Thr Leu Met Gln Asp Ser Gln Asp Phe Ser Ser Tyr Leu Ser
                   185                 190                 195
Asp Gly Leu His Leu Ser Pro Lys Gly Asn Glu Phe Leu Phe Ser
                   200                 205                 210
His Leu Trp Pro Leu Ile Glu Lys Lys Val Ser Ser Leu Pro Leu
                   215                 220                 225
Leu Leu Pro Tyr Trp Arg Asp Val Ala Glu Ala Lys Pro Glu Leu
                   230                 235                 240
Ser Leu Leu Gly Asp Gly Asp His
                   245

<210> SEQ ID NO 15
<211> LENGTH: 1231
<212> TYPE: DNA
<213> ORGANISM: Homo sapiens
<220> FEATURE:
<221> NAME/KEY: misc_feature
<223> OTHER INFORMATION: Incyte ID No: 1659002CB1

<400> SEQUENCE: 15
ctggagtatc cagataggcg acacgccggc gggcggctga ggcgggaatg gctgctgtac      60
tgcagcgcgt cgagcggctg tccaatcgag tcgtgcgtgt gttgggctgt aacccgggtc     120
ccatgaccct ccaaggcacc aacacctacc tagtggggac cggccccagg agaatcctca     180
ttgacactgg agaaccagca attccagaat acatcagctg tttaaagcag gctctaactg     240
aatttaacac agcaatccag gaaattgtag tgactcactg gcaccgagat cattctggag     300
gcataggaga tatttgtaaa agcatcaata atgacactac ctattgcatt aaaaaactcc     360
cacggaatcc tcagagagaa gaaattatag gaaatggaga gcaacaatat gtttatctga     420
agatggagat gtgattaag actgagggag ccactctaag agttctatat accctggcc       480 acactgatga tcacatggct ctactcttag aagaggaaaa tgctatcttt tctggagatt     540
gcatcctagg ggaaggaaca acggtatttg aagacctcta tgattatatg aactcttttaa    600 aagagttatt gaaaatcaaa gctgatatta tatccagg acatggccca gtaattcata       660
atgctgaagc taaattcaa caatacattt ctcacagaaa tattcgagag cagcaaattc      720
ttacattatt tcgtgagaac tttgagaaat catttacagt aatggagctt gtaaaaatta    780
tttacaagaa tactcctgag aatttacatg aaatggctaa acataatctc ttacttcatt    840
tgaaaaaact agaaaagaa ggaaaatat ttagcaacac agatcctgac aagaaatgga      900
```

-continued

| | |
|---|---|
| aagctcatct ttagtttcag attaaagaaa gctttgtttt attttgcttt gagagaatgg | 960 |
| tatgttttct taactatagg ttattttata gagaatataa aagtataaaa cattaaaaat | 1020 |
| aaccctagat atactttaaa ataatgttat atttatgcta aaatatgtaa attacactat | 1080 |
| acaaccatat gataggttat ttctctaacc ttgtcttcta acgttttacc aaaaattcat | 1140 |
| aatctaatag tttatcagtt ttcaatagat taaataaaat gattactttt aaaataataa | 1200 |
| aatttatcta atttaaagtt gaaaaaaaaa a | 1231 |

<210> SEQ ID NO 16
<211> LENGTH: 2636
<212> TYPE: DNA
<213> ORGANISM: Homo sapiens
<220> FEATURE:
<221> NAME/KEY: misc_feature
<223> OTHER INFORMATION: Incyte ID No: 1881009CB1

<400> SEQUENCE: 16

| | |
|---|---|
| tgggcgtgga ggtgtcgaga gtgactgtgc tggggctgct ccatcgttgt ctgagcctcc | 60 |
| cggtgctgcc gctgtggccg tttctttgat gaggctctca gaggccgagt cattcactgc | 120 |
| cggcctgaag ctgcccatgc gcatattcgg gctggagcct ctgaggccac acaaacgccg | 180 |
| gctggggagg cgaagtgtgg ggctgagcac cagaactcca ggagcgtctg ggctggagac | 240 |
| agaactgggt gggcaggtgg ggagggcctg cagatctgag tgggcagccg aggaggaacc | 300 |
| cagaagacgc cagcgatgga gctctgccgg ggcggaatgt ggccaggagg ggcgggagca | 360 |
| gtgacggcct gtccggcgct agaacgaggg accgtgctct caggacctct ggatgttccc | 420 |
| gagtatcctg atgttccacc cagaagccgc cagggccatc ctggagtacc gcatccgcac | 480 |
| gctggacggg gccctggaga acgcccagaa cctgggctac cagggagcca gtttgcctg | 540 |
| ggagagtgca gactccggcc tagaggtttg ccctgaggac atttacggag tccaggaggt | 600 |
| ccacgtcaac ggggccgtgg tgttggcctt cgagctgtac taccatacca cccaggacct | 660 |
| gcagctattt cgagaggctg gtggctggga cgtggtcagg gctgtggccg agttttggtg | 720 |
| cagtcgtgtt gagtggagcc ccaggggagg aaaagtaccac ctgaggggag tcatgtcccc | 780 |
| cgacgagtac cactcagggg tcaacaactc tgtgtacacc aacgtcctgg tccagaacag | 840 |
| cctgcgcttt gctgctgccc tggcccagga cctgggtctt cccatcccca gccagtggct | 900 |
| ggcggtggct gacaagatca aggtacccct tgacgtggag cagaacttcc acccggagtt | 960 |
| cgatgggtat gagcctggag aggtggtgaa gcaggcagac gtcgtgctcc tgggataccc | 1020 |
| agtccccttc tccctgagtc ctgatgttcg caggaaaaat ctggagattt acgaggctgt | 1080 |
| gacgtccccc cagggccccg ccatgacctg gagcatgttt gctgtgggct ggatggagct | 1140 |
| gaaggacgca gtgcgggccc ggggcctcct ggacaggagc tttgccaaca tggctgaacc | 1200 |
| cttcaaggtg tggacggaga atgcagacgt gtcaggcgct gtgaacttcc tgacaggcat | 1260 |
| gggggggcttc ctgcaggcgg tggtcttcgg gtgcacgggg ttcagggtca cccgagcggg | 1320 |
| tgtgaccttt gaccctgtgt gtctgtcggg gatctccaga gtgagcgtct ccggcatctt | 1380 |
| ctaccagggg aacaagctca acttctcttt tcccgaggac tccgtgaccg tggaggtcac | 1440 |
| agctcgagca gggccctggg ctcctcacct ggaggctgag ctgtggccat cccagtcccg | 1500 |
| gctctccctg ttgccaggac acaaggtctc ctttcccccgc tcggctggcc ggatacaaat | 1560 |
| gtcacccccg aagctgcctg gaagttccag ctccgagttc cctggaggga cttttttcaga | 1620 |
| tgttagggac ccgctccaga gccccctctg ggtcacccctg ggttcctcca gccccaccga | 1680 |

-continued

```
gtcactcact gtggaccctg cctctgaata atcaggaacg gtggcttcag agacgtctct    1740
tgggccttcc ctctggccac gtctgcaccc acccctcctg ggcaccctcc tagcctgcca    1800
tccctcacct gcagccaggc tctcagggaa ggtccatgct gcttggcctg agttcaaggc    1860
tttctgcctg tagcctggac tcccgtggac ccccgtgggc aggtggcttc cccgtggcat    1920
ctccacaccg cctctgcctg cccctgtgga ctgatgctat cgcgcacggt cccacgaccc    1980
caccccgagc tcctgaagcc ggggtctgag cctgcatcac ctctggcctc tcatccccca    2040
ctctcctgag agcagtggtc acagcggccg gccgctctgc tgagaaggca gagaggcagg    2100
ctcaggcctc agcgtggaca gcagggataa ggggcacgaa ggacggggac tcggccccctt   2160 cagaattcct caggactctc aggtgcagct ttgccaaaaa ggaacttttc atgtcatgca    2220
gttgagggga cttagtctca atcccaggct cctcttgact ctgggcagct ttaatcaggt    2280
tgggcagcct ctgctacagc gtggagtggg atggctctct cccctcagcc acgccgcttg    2340
tgaggacaga ggtgggggag tgggaagtgg gaagtcacca gagaacagga gagggatttg    2400
agggcgcgac cccagcgctc tccacggacc agccagaggg actggagcca ggtgtgcatg    2460
ggttcaaggc cctggccctg cccagcctct gtcttgggag ctcagcccca gggttcggtc    2520
gtcagcagtt tcccaagaac aagatgtgat ggcatctgct gctgaaaccc tgatgaggac    2580
caggccccct gcaccgctgt cagcctgagg aattaaagct ttggtgctgg gaagac        2636
```

<210> SEQ ID NO 17
<211> LENGTH: 2684
<212> TYPE: DNA
<213> ORGANISM: Homo sapiens
<220> FEATURE:
<221> NAME/KEY: misc_feature
<223> OTHER INFORMATION: Incyte ID No: 2054065CB1

<400> SEQUENCE: 17

```
gccggaagca ggaagtgagt ttgcgaacgg agcagctgct gctgcagcag ggcccatggc      60
ggacacccag tacatcctgc ccaatgacat cggcgtgtct agcctggact gccgtgaggc     120
cttccgcctg ctgtcaccca cagagcgcct ctatgcctac cacctgtccc gtgccgcctg     180
gtacggaggc ctggctgtgc tgcttcagac ctcccctgag gccccctaca tctatgctct     240
gctcagccgc ctcttccgcg cccaggaccc cgaccagctg cgccaacatg ccctggctga     300
aggccttacc gaggaggagt atcaggcgtt cctggtctat gccgcgggtg tttactccaa     360
catgggcaac tacaagtcct ttggtgacac caagtttgtt cccaacttgc caaggaaaa      420 gctggaacgg gtgatcctag ggagtgaggc tgctcagcag cacccagaag aagtcagggg     480
cctctggcag acctgcgggg agcttatgtt ctctctggag ccaaggcttc gacacctcgg     540
actggggcag gagggaatca ccacctatt  ctctgggaat tgtaccatgg aagatgccaa     600
attggcccag gactttctgg actcacagaa cctcagtgcc tacaacaccc ggctcttcaa     660
agaggtcgat ggagaaggga gccctactac gaggtgcgg ctggcttctg tgcttggctc      720
agagccttcc ctggactctg aggtgacttc caagctgaag agctatgaat tccggggaag     780
ccctttccag gtgacccggg gggactacgc gcccatcctc cagaaggtgg tggagcagct     840
ggagaaagcc aaggcctatg cagccaacag ccaccagggg cagatgctgg cccagtatat     900
agagagcttc acccagggct ccatcgaggc ccacaagagg ggctcccgct tctggatcca     960
ggacaaaggc cccatcgtgg agagttacat cgggttcatc gagagctacc gcgacccctt    1020
tggttcccga ggagaatttg aaggtttcgt agctgtggtg aacaaggcca tgagtgccaa    1080
```

-continued

| | |
|---|---|
| gtttgagcgg ctggtggcga gcgcagagca gctgctgaag gagctgccct ggcccccaac | 1140 |
| ctttgagaag gacaagttcc tcacccctga cttcacctcc ctggatgttc tcaccttcgc | 1200 |
| tggctccggc atccctgccg gcatcaacat ccccaactac gatgatctga ggcagacgga | 1260 |
| aggctttaag aacgtgtcgc tggggaatgt gctggctgtg gcctacgcca cgcagcggga | 1320 |
| gaagcttacc tttctggagg aggatgacaa ggacctgtac atcctctgga agggccctc | 1380 |
| cttcgatgtg caggtgggcc tgcacagct gctgggccat ggcagtggca agctcttcgt | 1440 |
| acaggacgaa aaaggagcat caactttga ccaggaaaca gtgatcaacc cagagacggg | 1500 |
| cgagcagatt cagagctggt atcggagcgg ggagacctgg gatagcaagt tcagcaccat | 1560 |
| cgcctccagc tacgaagagt gccgggctga gagcgtgggt ctctacctct gtctccaccc | 1620 |
| gcaagtgctg gagatctttg gctttgaggg ggctgatgcg gaggacgtga tctacgtgaa | 1680 |
| ctggctcaac atggttcggg ccgggctgct cgctctggag ttctacacac ctgaggcctt | 1740 |
| caactggcga caggcccata tgcaggcccg gtttgtgatc ctgagagtct tgctggaggc | 1800 |
| tggcgaggga ctcgttacca tcactcccac acaggctcc gatgggcgcc cagatgcccg | 1860 |
| ggtccgcctc gaccgcagca agatccggtc tgtgggcaag cctgctctag agcgcttcct | 1920 |
| gcggagactt caggtgctga agtccacagg ggatgtggcc ggagggcggg ccctgtacga | 1980 |
| ggggtatgca acggtcactg atgcgccccc cgagtgcttc ctcaccctca gggacacggt | 2040 |
| gctgctgcgt aaggaatctc ggaagctcat tgttcagccc aacactcgcc ttgaaggctc | 2100 |
| agacgtgcag cttctggaat acgaggcgtc agctgctggc ctcatccgat ccttctctga | 2160 |
| gcgtttccca gaggatggac ccgagttgga ggagatcctc acacagctgg ccacagccga | 2220 |
| tgcccgattc tggaagggcc ccagtgaggc cccatctggc caagcttgag gaagatgtgt | 2280 |
| ggccttgccc ccaattccat cagaccaagg ctgcaagtgg ccctccattc gtgtgtgtat | 2340 |
| ttaggggctg gggaggggga ggggcaggag cttggacctt ggtactacct cagctgaggg | 2400 |
| tggtgacaca accccttcca tttgtcagca cttttccagcc tgccaattgc ttcccctctg | 2460 |
| tgatctcatt tcatctgcac tgccatacgt ggagtgagca agacagggct taccatcctg | 2520 |
| tctaccagat gaggaaatgg cagttctgag aagtcactgg tctagatccc gcaggtggca | 2580 |
| cgtgacagct agggttcaaa acgttctcac caaatccaat gctcctcaca tattaatttt | 2640 |
| ataaccagac aaataaatat tagagacaac cacaaaaaaa aaaa | 2684 |

<210> SEQ ID NO 18
<211> LENGTH: 946
<212> TYPE: DNA
<213> ORGANISM: Homo sapiens
<220> FEATURE:
<221> NAME/KEY: misc_feature
<223> OTHER INFORMATION: Incyte ID No: 2183367CB1

<400> SEQUENCE: 18

| | |
|---|---|
| atcctgccaa agagagagac gcttttcacc ctggatgacc aggcgctggg gcccgagctc | 60 |
| acagctccag caccagagcc tcccgccgag gagccacgcc tggagcccgc gggcccagcc | 120 |
| tgcccggagg gagggcgagc ggagacgcag gccgaaccgc ccagcgtggg gccctagccg | 180 |
| gcgtcccctg cctccagaac gcgggctgga ccccaatgga gaacaggtgg tgtggcaggc | 240 |
| gagcggttgg gcagcccgca tcatccagca cgagatggac cacctgcagg gctgcctgtt | 300 |
| tattgacaaa atggacagca ggacgttcac aaacgtctat tggatgaagg tgaatgacta | 360 |
| aagctttgct actgggctg aggattccgg ataccaagac gcaaacactt tcactttgag | 420 |

-continued

| | |
|---|---|
| ctgggcaaat cttacttggc atcaacttgg atggctcgca tatgacagga aactggattg | 480 |
| ccaaggcatg gcagactgag ctggaggaag atgtcagaaa tgtttgccct gaaatcagtt | 540 |
| acggacaaaa tgttggctac aacttgagga gaaaaatcac ccccaaagga gtggacattt | 600 |
| cctaacaatt ctgtatggag gaaggtgggg taattgcatt cgtctgcagt agacacgagt | 660 |
| tcctcggacc tgtataatct cccaaagcca aggtttggta ataatgtagt ccccaaatac | 720 |
| ctgaaagctg tctttaaaaa tgcaggtaag catgtgactg gccatttgtg ccgagttctt | 780 |
| attttttacgg agggcttgtg gccttagacg ccagtttgct tatggaaatg aaagagaata | 840 |
| gtccctgttc aaggatgtgt ttcatgacag cacgagtgta aatgagtgcc cacacatttt | 900 |
| aacagccttg ggcaggattt tgctgctgag aaaataaaaa aaaaaa | 946 |

<210> SEQ ID NO 19
<211> LENGTH: 2092
<212> TYPE: DNA
<213> ORGANISM: Homo sapiens
<220> FEATURE:
<221> NAME/KEY: misc_feature
<223> OTHER INFORMATION: Incyte ID No: 2458536CB1

<400> SEQUENCE: 19

| | |
|---|---|
| ggcaattagc gcgcgccagg ctgccttccc cgcgccggac ccgggacgtc tgaacggaag | 60 |
| ttcgacccat cggcgacccg acggcgagac cccgccccat ccccgactgc ctgaaccgcg | 120 |
| ccaggagacg gaccgcaagt ccagcgtacc cacagacgac tcaggcggga gacgagcggt | 180 |
| gtcatggccg ccgacagtga cgatggcgca gtttcagctc ccgcagcttc cgacggtggt | 240 |
| gtcagcaaaa gcacaacatc tggggaggag ctagtagtcc aggttcccgt agtggatgtg | 300 |
| caaagcaaca acttcaagga gatgtggcca tccctcctgc tagccataaa gacagctaat | 360 |
| ttcgtggctg tggacacgga gctgagtggg cttggggaca ggaagagttt gctgaaccag | 420 |
| tgcattgagg aacgttacaa ggccgtgtgt catgctgcca ggacccgttc tatcctttcc | 480 |
| ctgggcctcg cctgcttcaa gcggcagcca gacaagggtg aacattccta tctggctcaa | 540 |
| gtgttcaatc tcactctgct gtgcatggag gagtatgtca tagaaccaaa gtctgtgcag | 600 |
| ttcctgatac agcatggctt caacttcaac cagcagtatg cccaaggcat ccctaccat | 660 |
| aagggcaatg acaagggtga tgagagccag agccagtcag tacggaccct attcctggag | 720 |
| ctaatccgag cccgccggcc cctggtgcta cacaatggcc ttatagactt ggtgttcctg | 780 |
| taccagaact tctatgcaca cctccctgag agtctgggaa ccttcaccgc tgacctgtgt | 840 |
| gagatgttcc cagcaggcat ttatgacacc aaatatgctg ctgagtttca tgcccgtttc | 900 |
| gtggcctcct acttagaata tgccttccgg aaatgtgaac gggaaaatgg gaagcagcgg | 960 |
| gcagctggca gcccacacct taccctggag ttctgcaact atccttccag catgagggac | 1020 |
| catattgatt accgctgctg cctgccccca gcaacccacc gtcctcatcc caccagcatc | 1080 |
| tgtgacaact tctcggctta tggctggtgc ccctgggac cacagtgtcc tcagtctcac | 1140 |
| gatattgacc ttatcattga cactgatgag gctgcggcag aggacaagcg gcgacggcga | 1200 |
| cgacgtaggg aaaaacggaa gagggcttta ttgaacctac cggggacaca gacctctggg | 1260 |
| gaagctaagg atggtcctcc caagaagcag gtctgtgggg atagcatcaa gcctgaagaa | 1320 |
| accgagcagg aggtggctgc cgatgaaact aggaacctgc ctcactccaa gcaaggcaac | 1380 |
| aaaaatgact tagagatggg gattaaggca gcaaggcctg aaatagctga tagagctacc | 1440 |
| tcagaagtgc cagggagcca agccagtcct aacccagtgc ctggggatgg attgcaccgg | 1500 |

-continued

```
gctggttttg atgcctttat gacaggttat gtgatggcct atgtggaagt gagccaggga    1560
ccgcagccct gcagctctgg accctggctc cctgaatgcc acaataaggt atatttgagt    1620
ggcaaagctg taccoctcac agtggccaag agccagttct ctcgttcctc caaagcccac    1680
aatcagaaga tgaagctcac ttggggcagt agctgatgca acttccacct tgctctcagg    1740
tggaacagag gtattttggg tctctctagc ctgaaatgtc atcctcaact gctactgagt    1800
ttaggggagg gggaatgtct tgacagacat cactgcattg ccctggaccg cctcctttat    1860
cccagtgttt gaggtacaag taagaaggct gaccagcacc tgtaacactg actttatttt    1920
taagtctgaa aatgtcttgg gaaagttta caaaaaaaa aatcaacaga agcaagttat    1980
gaaaatattt gaccagcttc atctttggtt atttcttatt gcagctctgt aaggacagac    2040
tgttcccaaa gctccagcca tggcaggaag ggaagcaaat acagtctcca tt    2092
```

<210> SEQ ID NO 20
<211> LENGTH: 2625
<212> TYPE: DNA
<213> ORGANISM: Homo sapiens
<220> FEATURE:
<221> NAME/KEY: misc_feature
<223> OTHER INFORMATION: Incyte ID No: 2472979CB1

<400> SEQUENCE: 20

```
agctgttggt gggggtgcag cactgagccg ccgacggggc gggtgggctt tgctgccgag     60
caggcggcgc cgtcttgggg cctagcggcg aggcgacccg cacagtactg taagattgat    120
gttaaaggca tggtgttcac cccacttcat cagcgtacaa agttatctc ttcttttgga    180 cccttatttt atgccataat gcaacaagct ttagaactag ctttggatcg tgcagagtat    240
gtcattgaaa gtgcccgaca gagacctcct aaaaggaaat acctatcaag tggaagaaaa    300
tctgtatttc aaaaacttta tgacttgtat attgaagaat gtgaaaaaga acctgaagtt    360
aagaaattaa gaagaaatgt gaacttgtta gagaagcttg ttatgcaaga gactttgtca    420
tgtttagtgg tcaatctata cccaggaaat gagggatatt ctctgatgct caggggaaaa    480
aacggatcag attccgagac cattcgactg ccctatgaag aaggagagtt gcttgaatat    540
ttggatgcag aagaattacc tcctatttg gttgatctcc tagaaaaatc tcaggttaat    600 attttttcatt gcggatgtgt catagcagaa atacgtgact acaggcagtc cagtaacatg    660
aaatctcctg gttaccaaag tcggcacatt ctcttacgtc caacaatgca gactttaatt    720
tgtgatgtac attcaataac aagtgataac cacaaatgga cccaggaaga caaacttttg    780
cttgagagcc agctcatcct agctacagct gaaccactct gtcttgatcc ttctatagca    840
gtcacctgca ctgcaaacag actgctctat aacaagcaaa agatgaacac tcgcccaatg    900
aaacggtgtt tcaagaggta ttccagatcc tctctgaatc ggcagcaaga tctatctcat    960
tgtccacctc ctcctcagct gaggttactt gatttcttac aaaaaagaaa ggaaagaaaa   1020
gcaggtcagc attatgacct caaaatttct aaggcaggaa attgtgtaga tatgtggaaa   1080
cggagtccct gtaatttggc cataccttct gaagtagatg tggagaaata tgctaaagtg   1140
gaaaagtcta tcaaatctga tgactcacag ccaacagtct ggccagccca tgatgtaaaa   1200
gatgattatg tatttgaatg tgaagctggt actcagtatc agaaaacaaa gctgaccatc   1260
ttgcagtcgc ttggagatcc actttactat ggtaaaatac agccatgtaa agcagatgaa   1320
gaaagtgaca gccagatgtc tccatcacac tcgtccacag atgatcattc aaattggttc   1380
attattggat caaagaccga tgctgagagg gtagtcaatc agtaccaaga attagtccag   1440
```

```
aatgaagcca aatgtccggt caagatgtca cacagctcca gtggctcagc cagtctgagt   1500
caggtttctc cagggaaaga aacagatcaa actgaaaccg tgtcagttca gtcttcggta   1560
ttggggaagg gtgtaaaaca tcgaccccca ccaatcaaac ttccctcaag ctcaggaaat   1620
agttcctcag gtaactattt tacaccacaa cagacaagca gctttctcaa atctccaact   1680
cctcctcctt cttctaagcc atcaagtatt cctcggaaat catctgtgga tctcaatcaa   1740
gttagcatgc tttctccagc tgccctatca cctgccagct catcacaaag aaccacggcc   1800
acccaggtca tggcaaactc tgctggactt aacttcatca atgtagtggg ctctgtttgt   1860
ggggcccagg ctttgatgag tggttcaaac cccatgctgg gctgtaacac tggtgccata   1920
actcctgcag gaataaacct gagcggcctt ctaccctcag gaggtctgct accaaatgca   1980
ctgcccagtg caatgcaggc agcttctcaa gcaggtgttc catttggttt aaaaaatact   2040
tcaagtctca ggcccttaaa tctactccag cttccaggtg gttcacttat ttttaacact   2100
ctgcagcagc agcaacagca gctctcccag tttacaccac aacaacctca gcagcccaca   2160
acttgtagtc ctcaacagcc aggggagcag ggttctgagc aaggttcaac cagtcaagaa   2220
caggccttat ctgctcagca agctgctgtt attaacctta ctggagtagg aagttttatg   2280
cagtcacagg cagctgcagt tgcgattctt gcagcatcaa atggctatgg cagcagcagc   2340
agcacaaaca gctcagctac atcatcatcg gcatacaggc agccagtcaa aaagtaaaat   2400
gaagagaggc acgccaacca ctccaaaatt ttgagtcttg cattactttt tgttcctttt   2460
ttaaaaacac aagagcactg aatcaaaaga attgagtttc tacttttttgt ttttttttaat   2520 gtgtcagtat tttacattgc tagatgtaca aactttatac agaagcacaa ccttatcatt   2580
tttaaataaa aacagggaaa tggtttaaca aaaaaaaaaa aaaaa   2625
```

<210> SEQ ID NO 21
<211> LENGTH: 2687
<212> TYPE: DNA
<213> ORGANISM: Homo sapiens
<220> FEATURE:
<221> NAME/KEY: misc_feature
<223> OTHER INFORMATION: Incyte ID No: 2612754CB1

<400> SEQUENCE: 21

```
cgcggcgcgg ccaggcccgg ccgaccgcgt ctcggtcttc gcgtctgcca gcctggctgg   60
cagtccgtct gtccatcccg ccgcgccggg gcagtctagg cggagggggg ctcaggcggc   120
ggcggcctcg acgcgagtga gtgtcgtggt tggggtgctg gacccagagt gcctaccctc   180
gcctgcctgg gcctcagttt ccacatctgc acaatggggg tgaccatccc tgccctgctg   240
gctgccagga gcggctgtga gtcttcaggc gtggatgcag cctgggggaa gccatagggc   300
gctttcacag gcctggcctt caccatggcg ggagggagac cgcatctgaa gaggagtttc   360
tccatcatcc cctgctttgt cttcgtggag tcggtgctgc tgggcattgt gatcctgctt   420
gcttaccgcc tggagttcac ggacaccttc cctgtgcaca cccagggatt cttctgctat   480
gacagtacct acgccaagcc ctacccaggg cctgaggctg ccagccgagt gcctcctgct   540
cttgtctacg cactggtcac tgccgggccc accctcacga tcctgctggg agagctggcg   600
cgtccctttt tccctgcacc accttcagcc gtcccagtca tcggggagag caccatcgtg   660
tctggggcct gctgccgctt cagcccccca gtgcggaggc tggtccgctt cctgggggtc   720
tactccttcg gcctcttcac cacgaccatc ttcgccaacg cggggcaggt ggtgaccggc   780
aatcccacgc cacacttcct gtccgtgtgc cgccccaact acacggccct gggctgcctg   840
```

-continued

```
ccaccttctc cggatcggcc aggtcccgac cgctttgtca ctgaccaggg tgcctgcgct      900
ggcagtccca gcctcgtggc cgccgcgcgc cgcgccttcc cctgcaagga tgcggccctc      960
tgcgcctacg cggtcaccta cacagcgatg tacgtgactc tcgtgttccg cgtgaagggc     1020
tcccgcctgg tcaaaccctc gctctgcctg gccttgctgt gccggccctt cctggtgggc     1080
gtggtccgcg tggccgagta ccgaaaccac tggtcggacg tgctggctgg cttcctgaca     1140
ggggcggcca tcgccacctt tttggtcacc tgcgttgtgc ataactttca gagccggcca     1200
ccctctggcc gaagcgtctc tccctgggag gacctgggcc aagccccac catggatagc       1260
cccctcgaaa agaacccgag gtctgcaggc cgcattcgac accggcacgg ctcacccat       1320
ccaagtcgca gaactgcgcc cgccgtggcc acctgatccc cagctgtgtc tcctccaggg     1380
ccccagccat gtgttcgtcg ccccgtgtgc ccgtcctcg attgaggtct gagccgacgc       1440
ccttgcccct gccctaccc ctgccagcgc ccaccccag ccagggcccc tcgccttcct        1500
cccctggacc tggggggcca ggcggggtg gtggacgtgg ccggaagctg ctgctgccca      1560
cgcccctgct gcgggacctg tacaccctga gtggactcta tccctccccc ttccaccggg     1620
acaacttcag cccttacctg tttgccagcc gtgaccacct gctgtgaggc ccgaccaccc     1680
acccagaatc tgcccagtcc ccacttcttc cctgccacgc gtgtgtgtgc gtgtgccacg     1740
tgagtgccaa agtcccctgc cccccaagcc agccagaccc agacattaga agatggctag    1800
aaggacattt aggagacatc tgcctctctg gccctctgag atatcccgat gggcacaaat     1860
ggaaggtgcg cacttgcccc tactattgcc cttttaaggg ccaaagcttg acccattgg      1920
ccattgcctg gctaatgaga acccctggtt ctcagaattt taaccaaaag gagttggctc     1980
caaccaatgg gagccttccc ctcacttctt agaatcctcc tgcaagaggg caactccagc    2040
cagtgttcag cgactgaaca gccaatagga gcccttggtt tccagaattt ctagagtggg    2100
tgggcatgat tccagtcaat ggggggaccgc ccgtgtctaa gcatgtgcaa aggagaggag   2160
ggagatgagg tcattgtttg tcattgagtc ttctctcaga atcagcgagc ccagctgtag   2220
ggtgggggc aggctccccc atggcagggt ccttgggta ccccttttcc tctcagcccc       2280
tccctgtgtg cggcctctcc acctctcacc cactctctcc taatccccta cttaagtagg    2340
gcttgcccca cttcagaggt tttgggggttc agggtgctgt gtctcccctt gcctgtgccc    2400
aggtcatccc aaaccctctc gttatttatt agggctgtgg aagggtttt tcttctttt       2460
cttgaacct gccctgttc ttcacactgc cccccatgcc tcagcctcat acagatgtgc       2520
catcatgggg ggcatgggtg gagcagaggg gctccctcac cccgggcagg caaaggcagt    2580
gggtagagga ggcactgccc cccttttcctg cccctcctc atctttaata aagacctggc    2640
ttctcatctt taataaagac ctgtttgtaa cagaaaaaa aaaaaa                      2687
```

<210> SEQ ID NO 22
<211> LENGTH: 2894
<212> TYPE: DNA
<213> ORGANISM: Homo sapiens
<220> FEATURE:
<221> NAME/KEY: misc_feature
<223> OTHER INFORMATION: Incyte ID No: 2616646CB1

<400> SEQUENCE: 22

```
ccgatctcgg cctcagcgtg agcatgcgca ggtccccgcc ctcgctgcgt ttgcgcttga       60
gcgccgataa tttggtggcg gcgtccggag ggtgctggtt tgttctcggt gaacggcgcg      120
cggggtctct cctgagtgcg agctacggga ccttcgccat gccggggatg gtactcttcg     180
```

```
gccggcgctg ggccatcgcc agcgacgact tggtcttccc agggttcttc gagctggtcg    240
tgcgagtgct gtggtggatt ggcattctga cgttgtatct catgcacaga ggaaagctgg    300
actgtgctgg tggagccttg ctcagcagtt acttgatcgt cctcatgatt ctcctggcag    360
ttgtcatatg tactgtgtca gccatcatgt gtgtcagcat gagaggaacg atttgtaacc    420
ctggaccgcg gaagtctatg tctaagctgc tttacatccg cctggcgctg ttttttccag    480
agatggtctg ggcctctctg ggggctgcct gggtggcaga tggtgttcag tgcgacagga    540
cagttgtaaa cggcatcatc gcaaccgtcg tggtcagttg gatcatcatc gctgccacag    600
tggtttccat tatcattgtc tttgaccctc ttgggggaa aatggctcca tattcctctg    660
ccggccccag ccacctggat agtcatgatt caagccagtt acttaatggc ctcaagacag    720
cagctacaag cgtgtgggaa accagaatca agctcttgtg ctgttgcatt gggaaagacg    780
accatactcg ggttgctttt tcgagtacgg cagagctttt ctcaacctac ttttcagaca    840
cagatctggt gcccagcgac attgcggcgg gcctcgccct gcttcatcag caacaggaca    900
atatcaggaa caaccaagag cctgcccagg tggtctgcca tgccccaggg agctcccagg    960
aagctgatct ggatgcagaa ttagaaaact gccatcatta catgcagttt gcagcagcgg   1020
cctatgggtg gcccctctac atctacagaa accccctcac ggggctgtgc aggattggtg   1080
gtgactgctg cagaagcaga accacagact atgacttggt cggaggcgat cagctcaact   1140
gtcacttcgg ctccatcctg cacaccacag ggctgcagta cagggacttc atccacgtca   1200
gcttccatga caaggtttac gagctgccgt ttttagtggc tctggatcac aggaaagagt   1260
ctgttgtggt cgctgtgagg gggaccatgt ctctgcagga tgtccttacg gacctgtcag   1320
cggagagtga ggtgctggac gtggagtgtg aggtgcagga ccgcctggca cacaagggta   1380
tttctcaagc tgccagatac gtttaccaac gactcatcaa cgacgggatt ttgagccaag   1440
ccttcagcat tgctcctgag taccggctgg tcatagtggg ccacagcctc ggggagggg    1500 cggccgccct gctggccacc atgctcagag ccgcctaccc gcaggtcagg tgctacgcct   1560
tctccccacc ccgggggctg tggagcaaag ctctgcagga atattctcag agcttcatcg   1620
tgtcactcgt cctggggaag gatgtgattc ccaggctcag tgtgaccaac ttggaagatc   1680
tgaagagaag aatcttgcga gtggtcgcgc actgcaataa acccaagtac aagatcttgc   1740
tgcacggttt gtggtacgaa ctgtttggag gaaaccccaa caacttgccc acggagctgg   1800 acggggcga ccaggaagtc ctgacacagc ctcttctggg ggagcagagc ctactgacgc   1860
gctggtcccc ggcctacagc ttctccagcg actccccact ggactcttct cccaagtacc   1920
cccctctcta ccctcccggc aggatcatcc acctgcagga ggagggcgcc tcggggcggt   1980
ttggctgctg ctctgctgct cactatagcg ccaagtggtc acacgaagcg gaattcagca   2040
aaatactcat aggtccgaag atgctcaccg accacatgcc agacatcctg atgcgggcct   2100
tggacagcgt ggtctccgac agagcggcct gcgtctcctg tccagcacaa ggggtctcca   2160
gtgtggacgt ggcctgacca gggccactgg aaactgtccc aggaacgatg gactcacgct   2220
tttgtcctta aactgactta ccatccgagg agttcccatg acgccaaaac agcgaatgtc   2280
catcaacagg aatcggatgg gaacagaatt ccatggtctc aatgacttaa gtttatggga   2340
agtcattgtg gccataatgg tagcagaagt agtgagcacg ctcaggtgat aggacgactc   2400
ctgagaccca gcgaccgtgg agacagcctc gggaagccct ggcccgtgga tggatccctt   2460
ggctgtctga ggactgctcc agaagtgcgg gaatccaggg cccacccaga agaccgtgaa   2520
cagttcctta gcctcccacc ccccaaggca gctctttca tccaactcag tttacaggcg    2580
```

```
tggtttgttt tcaaactgg gcttcctgga tgtacaaatg gaactgtggt gagggtgcgg    2640
gctggggttt tctcctgggc gtcaccaagg gcagccctgg gctctggctg gggatgaaga    2700
cgaaacccga tcgggaaagt aagtggagcc cccggccccg ccgagccaca gcccccaac     2760 tgcctattcc cactgcccag ttgtttgtcc acatcaggag ttgctgattg aattcttgct    2820
actcttctgg ctctggggtc ggccagtgga ttcaggagtt gaaacaataa agcgcgcgtc    2880
acgataaaaa aaaa                                                      2894

<210> SEQ ID NO 23
<211> LENGTH: 752
<212> TYPE: DNA
<213> ORGANISM: Homo sapiens
<220> FEATURE:
<221> NAME/KEY: misc_feature
<223> OTHER INFORMATION: Incyte ID No: 2625111CB1

<400> SEQUENCE: 23
cccggccgcg caggacttga catgctgccc gactgcctgt cggccgaggg cgagctgcgc     60
tgccgccggc tgctggcagg ggccacggcc cggctccgcg cgcggcccgc gtcggccgcg    120
gtgctcgtgc cgctctgctc agtgcgtggg gtcccggcgc tgctgtacac gctgcggtcc    180
agccgcctga ccgggaggca caagggcgac gtcagtttcc caggcggcaa gtgcgacccg    240
gctgaccaag atgtggtgca cacggccctg cgggaaaccc gggaggagct gggcctggca    300
gtgcccgagg agcacgtgtg gggcctgctg cggcctgtgt atgatccgca aaaggccacc    360
gtggtgccag tgcttgctgg tgtaggccca ctggatcccc agagcctcag gcccaactcg    420
gaggaggtag atgaggtgtt tgcactgccg ctggcccacc tgctgcagac gcagaatcag    480
ggctataccc acttctgccg gggtggccac ttccgctaca cactacccgt cttcctgcat    540
ggaccacacc gggtctgggg cctcacagct gtcatcactg agtttgccct gcagctgctg    600
gcacctggta cctaccagcc ccgcctggcc ggcctgacct gctcaggggc tgagggtctg    660
gcccgcccta gcagcccct ggcttcaccc tgtcaggcca gctccactcc aggactgaat    720
aaaggtcttt gacagctcta aaaaaaaaaa aa                                  752

<210> SEQ ID NO 24
<211> LENGTH: 1840
<212> TYPE: DNA
<213> ORGANISM: Homo sapiens
<220> FEATURE:
<221> NAME/KEY: misc_feature
<223> OTHER INFORMATION: Incyte ID No: 2724525CB1

<400> SEQUENCE: 24
gccggtgggc ggtaggcggt gctacgggta gctgggtgct gtccaaaggc gacagggcgt     60
cgttagggga gcgagtcgtg accggttggg ccacactcaa cgtgggacga agcttcgcct    120
actgtttgac tacgtgcgtg cagcctcccc tcgatgtcgg ccctcgaaaa gagcatgcac    180
ctcggccgcc ttccctctcg cccacctcta cccggcagcg ggggcagtca gagcggagcc    240
aagatgcgaa tgggccctgg aagaaagcgg acttttccc ctgttccttg gagtcagtat    300
tttgagtcca tggaagatgt agaagtagag aatgaaactg gcaaggatac ttttcgagtc    360
tacaagagtg gttcagaggg tccagtcctg ctccttctgc atggaggagg tcattctgcc    420
ctttcttggg ctgtgttcac ggcagcgatt attagtagag ttcagtgtag gattgtagct    480
ttggatctgc gaagtcatgg tgaaacaaag gtcaagaatc ctgaagatct gtctgcagaa    540
```

```
acaatggcaa aagacgttgg caatgtggtt gaagccatgt atggggacct tcctcctcca       600
attatgctga ttggacatag catgggtggt gctattgcag tccacacagc atcatccaac       660
ctggtaccaa gcctcttggg tctgtgcatg attgatgttg tagaaggtac agctatggat       720
gcacttaata gcatgcagaa tttcttacgg ggtcgtccta aaaccttcaa gtctctggag       780
aatgctattg aatggagtgt gaagagtggc cagattcgaa atctggagtc tgcccgtgtc       840
tcaatggttg gccaagtcaa acagtgtgaa ggaattacaa gtccagaagg ctcaaaatct       900
atagtggaag gaatcataga ggaagaagaa aagatgagg aaggaagtga gtctataagc       960
aagaggaaaa aggaagatga catggagacc aagaaagacc atcctacac ctggagaatt      1020
gaactggcaa aaacagaaaa atactgggac ggctggttcc gaggcttatc caatctcttt      1080
cttagttgtc ccattcctaa attgctgctc ttggctggtg ttgatagatt ggataaagat      1140
ctgaccattg gccagatgca agggaagttc cagatgcagg tcctaccca gtgtggccat      1200
gcagtccatg aggatgcccc tgacaagta gctgaagctg ttgccacttt cctgatccgg      1260
cacaggtttg cagaacccat cggtggattc cagtgtgtgt ttcctggctg ttagtgacct      1320
gctgtccacc cctcctcaac atcgagctct gttgtaaata cgtcgcacca gaggccactg      1380
tgatgccact gtctcctctc catcccgccc agccatgtga cactggctcc cggtagacgg      1440
gcaccccgag atgtaccaac cttttcatgt attctgccaa aagcattgtt ttccagggcc      1500
cttgaccaac atcggcttcc ccagtccagg gctcccctgc tcctttccct tcctgtact      1560
ggggtagctc ctgcctgctc tccctgcgtt gcctaggta aagcctccag atttgccata      1620
ctgagcccct cttcctagca tcaggcgata catctgagtt caaatgtctt cccaggctca      1680
gggacctcca ttccttgaga ttgtcttggc atggcccagc cctgcctcat gggatggaca      1740
atgcatgggg tggtctttat ttttcccttt caaataaaac actagtcaag taccgtttta      1800
tcccagtcgt actctttcca ggttggaaga cccagagatg                             1840

<210> SEQ ID NO 25
<211> LENGTH: 1703
<212> TYPE: DNA
<213> ORGANISM: Homo sapiens
<220> FEATURE:
<221> NAME/KEY: misc_feature
<223> OTHER INFORMATION: Incyte ID No: 2824691CB1

<400> SEQUENCE: 25
ggcagcgcga gataaatcac gagaggaagc ttaaatctgt cgtttgaatt taggaccacc        60
tcggttcaca atggtccgta gtggaaaaaa tggtgacctt catcttaaac agattgcata       120
ttacaaacga actggtgaat atcattcaac tacactgcca agtgagagaa gtggcataag       180
aagagcagca aaaaatttg tcttcaaaga aaaaagctg ttttatgttg gaaaagacag        240
aaaacaaaat cgtttggtaa ttgtttcaga agaggaaaaa aagaaagtct taagagaatg       300
ccatgaaaat gacagtggag ctcatcatgg tatatccagg accctcactc tggtagaatc       360
caattattat tggacatctg tgaccaatga tgtcaaacag tgggtatatg cttgtcagca       420
ttgccaagtg gcaaaaaata cagttattgt agcaccgaaa cagcaccttc tcaaggtgga       480
aaatccatgg agtttagtta ctgttgatct gatggggcct tttcatacaa gcaacagaag       540
tcatgtatat gctataatca tgacagattt gttcaccaaa tggattgtga ttttgcctct       600
atgtgatgtt tcagcatcag aagtttctaa agctattatc aatatatttt tcttatatgg       660
acctcctcag aaaataataa tggaccaaag agatgaattc attcaacaga tcaatattga       720
```

-continued

| | |
|---|---|
| actgtacaga ttgtttggca taaagcaaat tgtaatttct cacacctctg gaactgttaa | 780 |
| cccaatggaa agtacaccta acacaatcaa agcatttctc tccaaacact gtgctgacca | 840 |
| cccaaacaat tgggatgatc acctatcagc tgtttcattt gccttcaatg taactcactt | 900 |
| ggaacctact aaaaatacac catattttca aatgtttagt cgaaatcctt atatgcctga | 960 |
| gacttcagat agtcttcatg aagtggatgg tgataataca agtatgtttg ccaaaattct | 1020 |
| agatgcaatt aaagaagctg ataaaataat ggagaataag acaacttcac tgggccagat | 1080 |
| ggagaacaac aatttggatg aactaaataa aagcaagatc attgttaaaa agaaacccaa | 1140 |
| acaattaaat ccatttcatt taaaagtggg tcatgaagtt ttaagacaaa ggaaaaattg | 1200 |
| gtggaaggat ggtcgttttc agtctgaatg ggttggtcct tgtgtcatag actatattac | 1260 |
| agaaagtgga tgtgctgtcc tgagagacaa cactgggggtt agactgaaaa gacctatcaa | 1320 |
| aatgtcccac cttaagccct acataagaga atccagtgaa caagaaagtc tttatctctt | 1380 |
| gcaaggttca gtagtggcag atcatgacta cattggattg cctgaaattc cgattggagc | 1440 |
| atatcaagca aatattctgg tggaagatgc aactattggt atagtcgata atgaattact | 1500 |
| gacatcaagc aaggatcgtg aactattaga atatagaaat acgaaaatct ctccattgat | 1560 |
| agacgatcat agttctcttg aaaagcagac tttcagtctg ttggactctt caaaccaggt | 1620 |
| tcttgaatac ttaagttagt aaataccaaa atttatttaa agtgcttgtt tagaatataa | 1680 |
| attcttaatg atatcttatt cat | 1703 |

<210> SEQ ID NO 26
<211> LENGTH: 2326
<212> TYPE: DNA
<213> ORGANISM: Homo sapiens
<220> FEATURE:
<221> NAME/KEY: misc_feature
<223> OTHER INFORMATION: Incyte ID No: 4722794CB1

<400> SEQUENCE: 26

| | |
|---|---|
| ggctgaagcg gggtaattcc tctcctgcaa ttacttttgg atggaagtat gccccttct | 60 |
| cagtagaaga tggtaatctt ggagaatgac catggagaag gggatgagtt ctggagaagg | 120 |
| gctgccttcc agatcatctc aggtttcggc tggtaaaata acagccaaag agttggaaac | 180 |
| aaaagcagtcc tataaagaga acgaggagg ctttgtgttg gtgcatgcag gtgcaggtta | 240 |
| tcattctgaa tccaaagcca aggagtataa acatgtatgc aaacgagctt gtcagaaggc | 300 |
| aattgaaaag ctgcaggccg gtgctcttgc aactgacgca gtcactgcag cactggtgga | 360 |
| acttgaggat tctccttta caaatgcagg aatgggatct aatctaaatc tgttaggtga | 420 |
| aattgagtgt gatgccagca taatggatgg aaaatcctta aattttggag cagttggagc | 480 |
| actgagtgga atcaagaacc cagtctcggt tgccaacaga ctcttatgtg aagggcagaa | 540 |
| gggcaagctc tcggctggca gaattcctcc ctgctttta gttggagaag gagcctacag | 600 |
| atgggcagta gatcatggaa taccctcttg ccctcctaac atcatgacca caagattcag | 660 |
| tttagctgca tttaaaagaa acaagaggaa actagagctg gcagaaaggg tggacacaga | 720 |
| ttttatgcaa ctaaagaaaa gaagacaatc aagtgagaag gaaaatgact caggcacttt | 780 |
| ggacacggta ggcgctgtgg ttgtggacca cgaagggaat gttgctgctg ctgtctccag | 840 |
| tggaggcttg gccttgaaac atccggggag agttgggcag gctgctcttt atggatgtgg | 900 |
| ctgctgggct gaaatactg gagctcataa ccccctactcc acagctgtga gtacctcagg | 960 |
| atgtggagag catcttgtgc gcaccatact ggctagagaa tgttcacatg ctttacaagc | 1020 |

-continued

```
tgaggatgct caccaagccc tgttggagac tatgcaaaac aagtttatca gttcacctt     1080 ccttgccagt gaagatggcg tgcttggcgg agtgattgtc ctccgttcat gcagatgttc    1140
tgccgagcct gactcctccc aaaataagca gacacttcta gtggaatttc tgtggagcca    1200
cacgacggag agcatgtgtg tcggatatat gtcagcccag gatgggaaag ccaagactca    1260
catttcaaga cttcctcctg gtgcggtggc aggacagtct gtggcaatcg aaggtggggt    1320
gtgccgcctg gagagcccag tgaactgacc cttcaggctg agtgtgaagc gtctcagagg    1380
catttcagaa cctgagcttt tggggtttt taactgaagt tggttgtttt atctttcttg     1440
ttttataatt cctattgcaa cctcgtgcac tgctcgagac acaagtgctg ctgtagttag    1500
cgcttagtga cacgcgggcc tttggtgggt gagcgggact gtgtgtgagt gtgtgcgcgt    1560
atgtgcgcac atatgtgtat gtgtggagta tgtgtgtttg cttctccgtg gatgaaatag    1620
aaactcctca ttgtgtgacc aggaatggtt aaatcatctt tacaaaatgt gtgctttaac    1680
tgtttacaag taaaacctaa agttgcagga acattttttt atttcgtaaa gaggtaccaa    1740
ctgtcgctga tgtgatatgt cagaactgaa gagtaaatct acttgtttaa atgacttgac    1800
agtggtagtg ctccatttaa taacagtaat aagtaataaa gtgttttttat ttgttaacca    1860 gtttaagtgg atcctgtggt aacttaaact gttgttctca tcccttatat ggggcatttt    1920
tctttaacaa agaatggttt cagtgaaaca atctagcaga gaattaatgt cagaacctt     1980 ttaaataata gtctgattga tacagtttgt acttatttca tcaagctttt ctaagcttaa    2040
atattgcata gcttcgagct gtatggacta tattatgaaa gaatatgtaa agagaacata    2100
cagtaatgca cagtccttaa tttgtgtata atggaaagtt atttacaata taacactgta    2160
aataagaaag caaagtttat gggaaaattc aatattatct ttgttttttgt ttaaatatat   2220 ttttaagata aaggcacaaa aataaaagaa gcgtattact gggtatagta tgtgactcct    2280
cttctcagac taataaatta tcttttgaaa agctcgataa aaaagg                   2326
```

<210> SEQ ID NO 27
<211> LENGTH: 614
<212> TYPE: DNA
<213> ORGANISM: Homo sapiens
<220> FEATURE:
<221> NAME/KEY: misc_feature
<223> OTHER INFORMATION: Incyte ID No: 5328267CB1

<400> SEQUENCE: 27

```
agcttccagt caccatgaag gctctcctag ttctggggtt cctcctgctc tctgcctctg      60
tccaggccaa gacctatgaa cgctgtgagt tcgccagaac tctgaaaagg aatgggatgt     120
ctggctacta tggagtcagc ctggcagact gggtgtgttt agctcagcat gagagcaatt     180
ataacacaca agccagaaac tacaaccctg agaccaaag caccgactat gggatatttc      240
agatcaatag ccgatactgg tgtaatgacg gcaaaacccc aagagcaaag aacgcctgtg     300
ggataccctg cagcgctctg ctgcaggatg acatcactgc agccatacaa tgtgcgaaga     360
gagttgtgag ggatccccaa ggcattcgag catgggtggc atggcaaaga cactgtaaaa     420
accgagatct atccgggtat attcggaact gtggagtctg gacgcagtgc acttctactc     480
agctcactct gtctctttct cactgtggga gtagctatgg ggaaggtccc acttccttgc     540
tttcccctca aaacaacagg gctttcactt cttagtttcc aacgcacttc acaatgctcc     600
cagaatccgg acat                                                       614
```

<210> SEQ ID NO 28

-continued

```
<211> LENGTH: 1174
<212> TYPE: DNA
<213> ORGANISM: Homo sapiens
<220> FEATURE:
<221> NAME/KEY: misc_feature
<223> OTHER INFORMATION: Incyte ID No: 5382277CB1

<400> SEQUENCE: 28
cgccccgccc cgcccggctg ctccatggcg ctgtgcgagg ccgcgggctg cgggagtgcc      60
ctgctctggc ctcgcttgtt gctcttcggg gactccatca cccagttttc cttccagcag     120
ggtggatggg gagcatcgct ggctgacagg ctggtcagaa aatgtgatgt tctgaatcgt     180
ggattttcag gttacaatac caggtgggcc aaaattatcc ttccaagatt aatcaggaaa     240
ggaaacagtt tggacatccc agtagcagtt acaattttct ttggggccaa tgacagtgca     300
ctaaaagatg agaatcccaa gcagcacatt ccctggagg agtacgctgc gaacctaaag     360
agcatggtgc agtacctgaa gtccgtggac atccctgaga atcgagtcat tctcatcacg     420
ccgaccccac tttgtgaaac agcctgggaa gaacagtgca tcatacaagg ttgcaaacta     480
aatcgcctga actctgttgt tggtgaatat gccaatgcgt gtttacaagt ggcccaagac     540
tgtgggactg acgtacttga cctgtggacc ctgatgcagg acagccagga cttctcatct     600
tatttatcag atggactaca tttgtctcca aaggggaatg aattttttgtt ctcgcatctc     660 tggcctttga tagagaaaaa ggtctcttct ctacctttgc tgcttcctta ctggcgggat     720
gtagcagaag caaaacctga attaagtctg ctgggagatg gagaccatta gccaatcaca     780
ggagacccaa atctgcttgt tatctacaga actcaaagtt gtcaatacgt agaggtacgc     840
ttttttcctc aggcttaaac ctttgccact gatattaata ataaaagtat tagatgattt     900
ttcagggaag ttttatactt aggtccattg tgtttcgaca gtatttatta atgcagatat     960
cagtgctaca gctataaaat ataccctgag cagcttgtta attctataaa tgacaaagac    1020
tatgttttta aaaagtcaca attttataaa aatggttttt cttacattct tttgagaact    1080
gtttcactca tacatacacc cacacacccc actcaaccctt gtatcaaatt ccaaaagtgt    1140
aactaaagta taagaatatc atgactagtt aaaa                                1174
```